US009499822B2

(12) United States Patent
Kuroda et al.

(10) Patent No.: US 9,499,822 B2
(45) Date of Patent: Nov. 22, 2016

(54) METHOD FOR SELECTIVELY CULTURING MICROORGANISM USING PHOSPHITE DEHYDROGENASE GENE AS MARKER

(71) Applicant: Hiroshima University, Hiroshima (JP)

(72) Inventors: Akio Kuroda, Hiroshima (JP); Ryuichi Hirota, Hiroshima (JP); Takenori Ishida, Hiroshima (JP)

(73) Assignee: HIROSHIMA UNIVERSITY, Hiroshima (JP)

( * ) Notice: Subject to any disclaimer, the term of this patent is extended or adjusted under 35 U.S.C. 154(b) by 0 days.

(21) Appl. No.: 14/413,035

(22) PCT Filed: Aug. 8, 2013

(86) PCT No.: PCT/JP2013/071569
§ 371 (c)(1),
(2) Date: Jan. 6, 2015

(87) PCT Pub. No.: WO2014/024998
PCT Pub. Date: Feb. 13, 2014

(65) Prior Publication Data
US 2015/0125934 A1    May 7, 2015

(30) Foreign Application Priority Data

Aug. 9, 2012   (JP) ................................ 2012-177605
Feb. 20, 2013  (JP) ................................ 2013-031540

(51) Int. Cl.
| | |
|---|---|
| *C12N 15/52* | (2006.01) |
| *C12N 9/02* | (2006.01) |
| *C07K 14/195* | (2006.01) |
| *C12N 1/14* | (2006.01) |
| *C12N 1/16* | (2006.01) |
| *C12N 1/20* | (2006.01) |

(52) U.S. Cl.
CPC ............. *C12N 15/52* (2013.01); *C07K 14/195* (2013.01); *C12N 1/14* (2013.01); *C12N 1/16* (2013.01); *C12N 1/20* (2013.01); *C12N 9/0004* (2013.01); *C12Y 120/01001* (2013.01)

(58) Field of Classification Search
None
See application file for complete search history.

(56) References Cited

U.S. PATENT DOCUMENTS

| | | | | |
|---|---|---|---|---|
| 3,494,832 A | * | 2/1970 | Florent .................... | C12N 1/38 435/139 |
| 6,277,596 B1 | * | 8/2001 | Watanabe ............ | C12N 9/2437 435/252.3 |
| 2010/0216190 A1 | * | 8/2010 | Martin ................... | C12N 15/70 435/69.6 |
| 2010/0317073 A1 | * | 12/2010 | Sayre ...................... | C10G 1/00 435/136 |

FOREIGN PATENT DOCUMENTS

| | | |
|---|---|---|
| WO | 2006/074194 | 7/2006 |
| WO | 2010/058298 | 5/2010 |
| WO | 2012/076984 | 6/2012 |

OTHER PUBLICATIONS

Lobato et al., J. Plant Dis. Prot. 117:102-109, 2010.*
Hellwig et al., Nat. Biotechnol. 22:1415-1422, 2004.*
Sodoyer, R., Antibiotic-Free Selection for Bio-Production: Moving Towards a New "Gold Standard", Antibiotic Resistant Bacteria—A Continuous Challenge in the New Millennium, Dr. Marina Pana (Ed.), 2012, InTech, 19 pages.*
European Search Report, EP Patent Application No. 13827447.7, mailed Oct. 22, 2015.
Kanda et al. "Application of a phosphite dehydrogenase gene as a novel dominant selection marker for yeasts." Journal of Biotechnology, vol. 182-183, Apr. 28, 2014, pp. 68-73.
International Search Report of PCT/JP2013/071569, dated Oct. 1, 2013.
Lopez-Arredondo, D.L. and Herrera-Estrella, L., "A Novel dominant selectable system for the . . . " Plant Biotnolology Journal, May 2013, vol. 11, pp. 516-525.
Ono, Satoshi, et al., "Application of the phosphite dehydrogenase gene as a selectable marker for mass cultivation of microorganisms," Proceedings of the Annual Meeting 2013 Sendai of Japan Society for Bioscience, Biotechnology and Agrochemistry, published online, Mar. 5, 2013 (English translation provided).
Woodyer, R., et al., "Relaxing the Nicotinamide Cofactor . . . ", Biochemistry, 2003, vol. 42, pp. 11604-11614.
Hirota, R., et al., "Isolation and characterization of . . . ", Journal of Bioscience & Bioengineering, Apr. 2012, vol. 113, No. 4, pp. 445-450.
Metcalf, W.W. and Wolfe, R.S., Journal of Bacteriology, vol. 180, No. 21, 1998, pp. 5547-5558.
Nikkei Baio Saishin Yogo Jiten (Nikkei Dictionary of Up-to-date Biotechnical Terms), 5th ed., Nikkei Business Publications, Inc., Sep. 17, 2002, p. 846 (English translation provided).
English translation of the International Preliminary Report on Patentability, International Patent Application No. PCT/JP2013/071569, mailed Feb. 12, 2015.

* cited by examiner

*Primary Examiner* — David J Steadman
(74) *Attorney, Agent, or Firm* — Casimir Jones, SC

(57) ABSTRACT

A simple and inexpensive method for selectively culturing a microorganism which method makes it possible to selectively culture a microorganism of interest even without using a sterilization operation or an antibiotic substance is provided. The method according to the present invention selectively culturing a microorganism includes the step of culturing, in a culture medium containing phosphorous acid as a sole phosphorous source, a recombinant microorganism into which a phosphite dehydrogenase gene has been introduced.

15 Claims, 15 Drawing Sheets

SEQUENCE LISTING

<160> NUMBER OF SEQ ID NOS: 33

<210> SEQ ID NO 1
<211> LENGTH: 336
<212> TYPE: PRT
<213> ORGANISM: Ralstonia sp. 4506

<400> SEQUENCE: 1

```
Met Lys Pro Lys Val Val Leu Thr His Trp Val His Pro Glu Ile Ile
1               5                   10                  15

Glu Leu Leu Ser Ala Ser Ala Asp Val Ile Pro Asn Thr Thr Arg Glu
            20                  25                  30

Thr Leu Pro Arg Ser Glu Val Ile Ala Arg Ala Lys Asp Ala Asp Ala
        35                  40                  45

Leu Met Ala Phe Met Pro Asp Ser Ile Asp Ser Ala Phe Leu Glu Glu
    50                  55                  60

Cys Pro Lys Leu Arg Val Ile Gly Ala Ala Leu Lys Gly Tyr Asp Asn
65                  70                  75                  80

Phe Asp Val Asn Ala Cys Thr Arg His Gly Val Trp Leu Thr Ile Val
                85                  90                  95

Pro Asp Leu Leu Thr Ile Pro Thr Ala Glu Leu Thr Ile Gly Leu Leu
            100                 105                 110

Leu Gly Leu Thr Arg His Met Leu Glu Gly Asp Arg Gln Ile Arg Ser
        115                 120                 125

Gly His Phe Gln Gly Trp Arg Pro Thr Leu Tyr Gly Ser Gly Leu Thr
    130                 135                 140

Gly Lys Thr Leu Gly Ile Ile Gly Met Gly Ala Val Gly Arg Ala Ile
145                 150                 155                 160

Ala Gln Arg Leu Ala Gly Phe Glu Met Asn Leu Leu Tyr Cys Asp Pro
                165                 170                 175

Ile Pro Leu Asn Ala Glu Gln Glu Lys Ala Trp His Val Gln Arg Val
            180                 185                 190

Thr Leu Asp Glu Leu Leu Glu Lys Cys Asp Tyr Val Val Pro Met Val
        195                 200                 205

Pro Met Ala Ala Glu Thr Leu His Leu Ile Asp Ala Thr Ala Leu Ala
    210                 215                 220
```

```
Lys Met Lys Thr Gly Ser Tyr Leu Ile Asn Ala Cys Arg Gly Ser Val
225                 230                 235                 240

Val Asp Glu Asn Ala Val Ile Ala Ala Leu Ala Ser Gly Lys Leu Ala
                245                 250                 255

Gly Tyr Ala Ala Asp Val Phe Glu Met Glu Glu Trp Ile Arg Ala Asp
            260                 265                 270

Arg Pro Gln Ala Ile Pro Lys Ala Leu Leu Asp Asn Thr Ala Gln Thr
        275                 280                 285

Phe Phe Thr Pro His Leu Gly Ser Ala Val Lys Glu Val Arg Leu Glu
    290                 295                 300

Ile Glu Arg Gln Ala Ala Met Asn Ile Ile Gln Ala Leu Ala Gly Glu
305                 310                 315                 320

Lys Pro Met Gly Ala Ile Asn Gln Pro Tyr Pro Gly Val Lys Ala Ala
                325                 330                 335

<210> SEQ ID NO 2
<211> LENGTH: 1011
<212> TYPE: DNA
<213> ORGANISM: Ralstonia sp. 4506

<400> SEQUENCE: 2
atgaagccca aagtcgtcct cacccactgg gtgcacccgg aaatcatcga attgttgtcc      60
gctagcgccg atgttatccc caacaccaca cgggaaacct tgccgcgttc tgaggtaatt     120
gcgcgagcca agatgcgga tgcactcatg gctttcatgc cggacagcat cgacagcgcg     180
tttctcgagg aatgtccaaa gctgcgtgtc atcggcgccg cgcttaaagg ctatgataac     240
ttcgatgtca acgcctgcac acgccacggt gtatggctta cgattgtgcc ggatttgctt     300
acgatcccga ccgctgaact gactatcggc cttcttctcg gtttgacaag gcatatgctg     360
gaaggcgata ggcaaatccg tagcggacac ttccaaggct ggcggccgac actatatggc     420
tctggtttga caggaaaaac gcttggcatc attggtatgg gggcggtcgg ccgtgcaatc     480
gcccagcgct tggctggctt tgaaatgaat ctcttgtatt gcgatccgat tccgctcaat     540
gccgaacaag aaaaggcttg gcacgtacag cgcgtcacgc tcgatgaact gctcgaaaaa     600
tgtgattatg tcgtgccgat ggttccgatg ccgcagaga cactgcatct gatcgatgcc     660
accgcgttgg ccaagatgaa accggtagc tacctgatca atgcatgtcg cggctcggtc      720
gtggatgaga atgcggtgat agcagcactg gcgtctggaa aactagctgg atatgcagcc     780
gatgtcttcg agatggaaga atggatacgc gctgatcgcc cgcaggctat ccccaaggcg     840
ctgctcgaca atacggcaca aacgtttttt acgccgcatt tgggatcggc ggtcaaggaa     900
gttcggcttg aaatcgagcg gcaggcagcg atgaacatca tccaggcact cgctggtgaa     960
aaaccgatgg gcgcgattaa tcagccgtat ccgggagtaa aggcggcgtg a             1011

<210> SEQ ID NO 3
<211> LENGTH: 272
<212> TYPE: PRT
<213> ORGANISM: Ralstonia sp. 4506

<400> SEQUENCE: 3

Met Ile Glu Leu Gln Asn Val Ser Val Ser Tyr Gly Asp Ala Ile Ala
1               5                   10                  15

Leu Tyr Pro Thr Thr Leu Lys Leu His Gln Gly Gln Phe Thr Val Leu
            20                  25                  30

Leu Gly Ser Ser Gly Ala Gly Lys Ser Thr Leu Leu Arg Cys Ile Asn
        35                  40                  45
```

```
Ser Leu His Ala Ser Gln Arg Gly Thr Thr Ile Val Ala Gly Leu Gly
    50                  55                  60

Asn Leu Ala Asn Ser Arg Ala Leu Arg Met His Arg Arg Gln Thr Gly
 65                  70                  75                  80

Met Val Phe Gln Gln His Gln Leu Ile Gly Arg Leu Thr Ala Leu Gln
                 85                  90                  95

Asn Val Ser Met Gly Arg Met Gly Tyr His Thr Ala Leu Arg Ser Leu
            100                 105                 110

Phe Pro Leu Pro Ala Lys Asp Gln Ser Ile Cys Leu Gln Ser Leu Asp
        115                 120                 125

Arg Val Gly Leu Leu His Lys Ala Leu Ser Arg Val Asp Ala Leu Ser
    130                 135                 140

Gly Gly Gln Gln Gln Arg Ile Gly Ile Ala Arg Ala Leu Ala Gln Gln
145                 150                 155                 160

Pro Lys Leu Val Leu Ala Asp Glu Pro Val Ala Ser Leu Asp Pro Ala
                165                 170                 175

Thr Ala Glu Arg Val Leu Ser Leu Leu His Arg Ile Cys Lys Glu Asp
            180                 185                 190

Gly Ile Ser Ala Val Ser Leu His Gln Val Asp Leu Ala Gln Arg
    195                 200                 205

Tyr Ala Asp Arg Ile Ile Gly Leu Ser His Gly Arg Val Ile Phe Asp
    210                 215                 220

Ala Ala Pro Gln Thr Leu Asp Gln Ala Ser Tyr Asp Thr Leu Tyr Glu
225                 230                 235                 240

Gln Val Pro Arg Ser Ser Leu Ser Val Pro Gln Asp Ala Arg Glu Glu
                245                 250                 255

Arg Leu Ile Asp Thr Ser Phe Pro Met Gln Leu Ala Thr Val Lys Asp
            260                 265                 270

<210> SEQ ID NO 4
<211> LENGTH: 286
<212> TYPE: PRT
<213> ORGANISM: Ralstonia sp. 4506

<400> SEQUENCE: 4

Met Lys Lys Leu Ala Ser Ala Leu Leu Ser Val Leu Leu Ala Ala Val
1               5                   10                  15

Cys Ser Ile Gly His Ala Ser Ser Asn Pro Asp Pro Glu Thr Leu Lys
                20                  25                  30

Val Ala Leu Leu Pro Asp Glu Asn Ala Ser Thr Val Ile Lys Asn Asn
            35                  40                  45

Lys Pro Leu Glu Ile Tyr Leu Glu Lys Glu Leu Gly Lys Lys Ile Glu
    50                  55                  60

Leu Val Val Thr Thr Asp Tyr Ser Ser Met Ile Glu Ala Met Arg His
 65                 70                  75                  80

Gly Arg Ile Asp Met Ala Tyr Phe Gly Pro Leu Ser Tyr Val Leu Ala
                85                  90                  95

Lys Gln Lys Ser Asp Ile Glu Pro Phe Ala Ala Met Lys Gln Lys Gly
            100                 105                 110

Ser Thr Thr Tyr Gln Ser Val Leu Ile Ala Asn Thr Gly Ala Gly Ile
        115                 120                 125

Ala Lys Ile Ser Asp Ile Val Asn Lys Asn Val Ala Tyr Gly Asp Lys
    130                 135                 140

Ala Ser Thr Ser Ser His Leu Ile Pro Lys Ser Ile Leu Ala Glu Asn
```

```
                145                 150                 155                 160
Gly Leu Lys Ala Gly Glu Asn Tyr Arg Glu His Phe Val Gly Ala His
                    165                 170                 175

Asp Ala Val Ala Met Ala Val Gln Asn Gly His Ala Gln Ala Gly Gly
                180                 185                 190

Leu Ser Lys Pro Ile Phe Glu Ser Leu Val Gln Arg Gly Leu Val Asp
                195                 200                 205

Pro Asn Lys Val Lys Val Leu Ala Glu Ser Lys Pro Tyr Pro Gln Tyr
            210                 215                 220

Pro Trp Thr Met Arg Ser Asn Leu Lys Pro Glu Leu Lys Lys Ile
225                 230                 235                 240

Arg Ala Ala Phe Leu Asn Leu Lys Asp Pro Glu Val Leu Lys Pro Phe
                    245                 250                 255

Lys Ala Asp Gly Phe Gly Pro Ile Ser Asp Lys Asp Tyr Asp Val Val
                260                 265                 270

Arg Ser Leu Gly Thr Leu Leu Lys Leu Asp Leu Ser Lys Phe
                275                 280                 285

<210> SEQ ID NO 5
<211> LENGTH: 269
<212> TYPE: PRT
<213> ORGANISM: Ralstonia sp. 4506

<400> SEQUENCE: 5

Val Ser Asp Ser Met Gln Ala Asp Phe Gly Leu Ile Leu Ala Glu Arg
1               5                   10                  15

Gln Arg Val Trp Asn Arg Thr Ile Leu Gln Phe Ala Val Val Leu Ala
                20                  25                  30

Ile Val Ile Gly Cys Trp Tyr Tyr Val Gly Leu Phe Asp Ala Glu Arg
            35                  40                  45

Leu Lys Asp Gly Met Pro Ser Leu Val Lys Ile Ala Gly Glu Met Phe
50                  55                  60

Pro Pro Asn Phe Ser Gln Ala Gly Thr Trp Val Lys Pro Val Leu Asp
65                  70                  75                  80

Thr Leu Ala Met Ser Ile Ala Gly Thr Ala Ile Ala Val Leu Leu Ser
                85                  90                  95

Ile Pro Leu Gly Val Leu Ala Ala Arg Asn Thr Ser Pro His Pro Leu
            100                 105                 110

Val Tyr Gln Ala Thr Arg Gly Leu Leu Asn Ala Leu Arg Ser Ile Pro
        115                 120                 125

Glu Leu Ile Met Gly Ile Leu Phe Val Ala Ala Val Gly Phe Gly Ala
    130                 135                 140

Leu Pro Gly Val Leu Ala Leu Gly Leu His Ser Val Gly Met Ile Ala
145                 150                 155                 160

Lys Phe Phe Ser Glu Ser Ile Glu His Ala Asp Pro Ala Pro Val Glu
                165                 170                 175

Ala Ala His Ala Ala Gly Cys Thr Pro Leu Gln Val Ile Phe His Gly
                180                 185                 190

Ile Phe Pro Gln Val Leu Pro Gln Met Ala Asp Thr Ala Ile Tyr Arg
            195                 200                 205

Trp Glu Tyr Asn Phe Arg Ala Ser Thr Val Met Gly Met Val Gly Ala
        210                 215                 220

Gly Gly Ile Gly Phe Glu Leu Met Gly Ser Leu Arg Ile Met Gln Tyr
225                 230                 235                 240
```

Gln Asp Val Ser Ala Ile Leu Leu Val Ile Leu Gly Met Val Thr Leu
         245                 250                 255

Val Asp Ala Phe Ser Ser Phe Leu Arg Arg Lys Phe Lys
         260                 265

<210> SEQ ID NO 6
<211> LENGTH: 861
<212> TYPE: DNA
<213> ORGANISM: Ralstonia sp. 4506

<400> SEQUENCE: 6

| | | | | | |
|---|---|---|---|---|---|
| atgaaaaaac | tcgcatccgc | attattgtct | gtcttgcttg | ccgccgtctg | cagcattggc | 60 |
| catgcatcat | ccaatcccga | tccagaaacg | ctcaaagttg | cgctgctgcc | ggacgaaaac | 120 |
| gcatcgaccg | taattaaaaa | caacaagccc | tcgaaatct | atctggaaaa | agagctggga | 180 |
| aagaaaattg | agctggtggt | taccactgat | tactcgtcaa | tgatcgaagc | catgcgtcac | 240 |
| ggccgtatcg | acatggcata | ttttggcccc | ttgtcgtatg | tgctggctaa | gcaaaagagc | 300 |
| gacatcgagc | cattcgcagc | gatgaagcaa | aagggtagca | ctacctacca | gtccgtattg | 360 |
| atcgccaata | ctggcgccgg | catcgccaaa | atcagtgata | tcgtcaacaa | gaatgtcgct | 420 |
| tacggtgata | aggcatccac | ctccagccat | ttgattccga | agtcgatatt | ggcggaaaac | 480 |
| ggtttgaaag | ccggcgaaaa | ctatcgcgaa | cactttgtcg | gtgcgcatga | cgcggtggcc | 540 |
| atggccgtgc | aaaacggtca | cgcgcaggct | ggcggcttga | gtaagccgat | ttttgaatcc | 600 |
| ctggttcagc | gcggactggt | cgatcccaac | aaagtaaaag | ttcttgccga | atcgaagcca | 660 |
| tatccgcaat | acccgtggac | catgcgcagc | aatctgaagc | cggaactgaa | ggaaaagatc | 720 |
| cgtgcagcct | tcttgaatct | caaagatccg | gaagtcctga | aacctttcaa | agccgatggt | 780 |
| ttcggcccga | tcagcgacaa | agactatgac | gtggtgcgca | gccttggcac | actgctcaag | 840 |
| ctcgatctgt | cgaagttcta | a | | | | 861 |

<210> SEQ ID NO 7
<211> LENGTH: 861
<212> TYPE: DNA
<213> ORGANISM: Ralstonia sp. 4506

<400> SEQUENCE: 7

| | | | | | |
|---|---|---|---|---|---|
| atgaaaaaac | tcgcatccgc | attattgtct | gtcttgcttg | ccgccgtctg | cagcattggc | 60 |
| catgcatcat | ccaatcccga | tccagaaacg | ctcaaagttg | cgctgctgcc | ggacgaaaac | 120 |
| gcatcgaccg | taattaaaaa | caacaagccc | tcgaaatct | atctggaaaa | agagctggga | 180 |
| aagaaaattg | agctggtggt | taccactgat | tactcgtcaa | tgatcgaagc | catgcgtcac | 240 |
| ggccgtatcg | acatggcata | ttttggcccc | ttgtcgtatg | tgctggctaa | gcaaaagagc | 300 |
| gacatcgagc | cattcgcagc | gatgaagcaa | aagggtagca | ctacctacca | gtccgtattg | 360 |
| atcgccaata | ctggcgccgg | catcgccaaa | atcagtgata | tcgtcaacaa | gaatgtcgct | 420 |
| tacggtgata | aggcatccac | ctccagccat | ttgattccga | agtcgatatt | ggcggaaaac | 480 |
| ggtttgaaag | ccggcgaaaa | ctatcgcgaa | cactttgtcg | gtgcgcatga | cgcggtggcc | 540 |
| atggccgtgc | aaaacggtca | cgcgcaggct | ggcggcttga | gtaagccgat | ttttgaatcc | 600 |
| ctggttcagc | gcggactggt | cgatcccaac | aaagtaaaag | ttcttgccga | atcgaagcca | 660 |
| tatccgcaat | acccgtggac | catgcgcagc | aatctgaagc | cggaactgaa | ggaaaagatc | 720 |
| cgtgcagcct | tcttgaatct | caaagatccg | gaagtcctga | aacctttcaa | agccgatggt | 780 |
| ttcggcccga | tcagcgacaa | agactatgac | gtggtgcgca | gccttggcac | actgctcaag | 840 |

```
ctcgatctgt cgaagttcta a                                              861
```

<210> SEQ ID NO 8
<211> LENGTH: 807
<212> TYPE: DNA
<213> ORGANISM: Ralstonia sp. 4506

<400> SEQUENCE: 8

```
gtgagcgaca gcatgcaagc tgattttggt ttgattctgg ccgagcgcca gcgcgtatgg      60
aaccgcacga tactgcagtt tgccgttgtg ctggcgattg tgatcggttg ctggtattac     120
gtcggcctat ttgatgccga gcgattgaag gatggcatgc aagcctggt aaaaattgcc     180
ggcgagatgt tcccaccgaa cttctcgcag gctggcacct gggtcaaacc ggtactggat     240
accttggcca tgagtatcgc cggcacggca atcgcggtat tgctatccat tcccttagga     300
gtgctcgccg cgcggaatac tagccctcat ccactcgtgt atcaagccac acgcggcctg     360
ttaaacgctt tgcgatcgat acccgaactg atcatgggca tcctgttcgt ggcagccgtt     420
ggcttcggcg cattgccggg tgttttagcc ctaggcttac attcggttgg catgatcgcc     480
aaatttttt cggaatcgat cgaacatgcc gatccggcac cggtagaagc cgcgcatgca     540
gcgggctgca cgccattgca ggtgattttt catgggatct ttccccaagt gcttccgcaa     600
atggccgata ccgcgatcta tcgatgggaa tacaacttcc gtgcttcgac cgtgatgggc     660
atggtcggcg ccggtggaat cgggttcgag ctgatgggct ctctgcgcat catgcaatac     720
caggatgtct cggctatttt gctggttatt ttaggcatgg ttaccctcgt cgacgccttc     780
agctccttcc tgcgtcgcaa gttcaaa                                         807
```

<210> SEQ ID NO 9
<211> LENGTH: 336
<212> TYPE: PRT
<213> ORGANISM: Ralstonia sp. 4506

<400> SEQUENCE: 9

```
Met Lys Pro Lys Val Val Leu Thr His Trp Val His Pro Glu Ile Ile
1               5                   10                  15

Glu Leu Leu Ser Ala Ser Ala Asp Val Ile Pro Asn Thr Thr Arg Glu
            20                  25                  30

Thr Leu Pro Arg Ser Glu Val Ile Ala Arg Ala Lys Asp Ala Asp Ala
        35                  40                  45

Leu Met Ala Phe Met Pro Asp Ser Ile Asp Ser Ala Phe Leu Glu Glu
    50                  55                  60

Cys Pro Lys Leu Arg Val Ile Gly Ala Ala Leu Lys Gly Tyr Asp Asn
65                  70                  75                  80

Phe Asp Val Asn Ala Cys Thr Arg His Gly Val Trp Leu Thr Ile Val
                85                  90                  95

Pro Asp Leu Leu Thr Ile Pro Thr Ala Glu Leu Thr Ile Gly Leu Leu
            100                 105                 110

Leu Gly Leu Thr Arg His Met Leu Glu Gly Asp Arg Gln Ile Arg Ser
        115                 120                 125

Gly His Phe Gln Gly Trp Arg Pro Thr Leu Tyr Gly Ser Gly Leu Thr
    130                 135                 140

Gly Lys Thr Leu Gly Ile Ile Gly Met Gly Ala Val Gly Arg Ala Ile
145                 150                 155                 160

Ala Gln Arg Leu Ala Gly Phe Glu Met Asn Leu Leu Tyr Cys Ala Pro
                165                 170                 175
```

```
Ile Pro Leu Asn Ala Glu Gln Glu Lys Ala Trp His Val Gln Arg Val
                180                 185                 190

Thr Leu Asp Glu Leu Leu Glu Lys Cys Asp Tyr Val Val Pro Met Val
            195                 200                 205

Pro Met Ala Ala Glu Thr Leu His Leu Ile Asp Ala Thr Ala Leu Ala
        210                 215                 220

Lys Met Lys Thr Gly Ser Tyr Leu Ile Asn Ala Cys Arg Gly Ser Val
225                 230                 235                 240

Val Asp Glu Asn Ala Val Ile Ala Ala Leu Ala Ser Gly Lys Leu Ala
                245                 250                 255

Gly Tyr Ala Ala Asp Val Phe Glu Met Glu Gly Trp Ile Arg Ala Asp
            260                 265                 270

Arg Pro Gln Ala Ile Pro Lys Ala Leu Leu Asp Asn Thr Ala Gln Thr
        275                 280                 285

Phe Phe Thr Pro His Leu Gly Ser Ala Val Lys Glu Val Arg Leu Glu
    290                 295                 300

Ile Glu Arg Gln Ala Ala Met Asn Ile Ile Gln Ala Leu Ala Gly Glu
305                 310                 315                 320

Lys Pro Met Gly Ala Ile Asn Gln Pro Tyr Pro Gly Val Lys Ala Ala
                325                 330                 335

<210> SEQ ID NO 10
<211> LENGTH: 336
<212> TYPE: PRT
<213> ORGANISM: Ralstonia sp. 4506

<400> SEQUENCE: 10

Met Lys Pro Lys Val Val Leu Thr His Trp Val His Pro Glu Ile Ile
1               5                   10                  15

Glu Leu Leu Ser Ala Ser Ala Asp Val Ile Pro Asn Thr Thr Arg Glu
                20                  25                  30

Thr Leu Pro Arg Ser Glu Val Ile Ala Arg Ala Lys Asp Ala Asp Ala
            35                  40                  45

Leu Met Ala Phe Met Pro Asp Ser Ile Asp Ser Ala Phe Leu Glu Glu
        50                  55                  60

Cys Pro Lys Leu Arg Val Ile Gly Ala Ala Leu Lys Gly Tyr Asp Asn
65                  70                  75                  80

Phe Asp Val Asn Ala Cys Thr Arg His Gly Val Trp Leu Thr Ile Val
                85                  90                  95

Pro Asp Leu Leu Thr Ile Pro Thr Ala Glu Leu Thr Ile Gly Leu Leu
            100                 105                 110

Leu Gly Leu Thr Arg His Met Leu Glu Gly Asp Arg Gln Ile Arg Ser
        115                 120                 125

Gly His Phe Gln Gly Trp Arg Pro Thr Leu Tyr Gly Ser Gly Leu Thr
    130                 135                 140

Gly Lys Thr Leu Gly Ile Ile Gly Met Gly Ala Val Gly Arg Ala Ile
145                 150                 155                 160

Ala Gln Arg Leu Ala Gly Phe Glu Met Asn Leu Leu Tyr Cys Asp Arg
                165                 170                 175

Ile Pro Leu Asn Ala Glu Gln Glu Lys Ala Trp His Val Gln Arg Val
            180                 185                 190

Thr Leu Asp Glu Leu Leu Glu Lys Cys Asp Tyr Val Val Pro Met Val
        195                 200                 205

Pro Met Ala Ala Glu Thr Leu His Leu Ile Asp Ala Thr Ala Leu Ala
```

```
            210                 215                 220
Lys Met Lys Thr Gly Ser Tyr Leu Ile Asn Ala Cys Arg Gly Ser Val
225                 230                 235                 240

Val Asp Glu Asn Ala Val Ile Ala Ala Leu Ala Ser Gly Lys Leu Ala
                245                 250                 255

Gly Tyr Ala Ala Asp Val Phe Glu Met Glu Trp Ile Arg Ala Asp
                260                 265                 270

Arg Pro Gln Ala Ile Pro Lys Ala Leu Leu Asp Asn Thr Ala Gln Thr
                275                 280                 285

Phe Phe Thr Pro His Leu Gly Ser Ala Val Lys Glu Val Arg Leu Glu
                290                 295                 300

Ile Glu Arg Gln Ala Ala Met Asn Ile Ile Gln Ala Leu Ala Gly Glu
305                 310                 315                 320

Lys Pro Met Gly Ala Ile Asn Gln Pro Tyr Pro Gly Val Lys Ala Ala
                325                 330                 335

<210> SEQ ID NO 11
<211> LENGTH: 336
<212> TYPE: PRT
<213> ORGANISM: Ralstonia sp. 4506

<400> SEQUENCE: 11

Met Lys Pro Lys Val Val Leu Thr His Trp Val His Pro Glu Ile Ile
1               5                   10                  15

Glu Leu Leu Ser Ala Ser Ala Asp Val Ile Pro Asn Thr Thr Arg Glu
                20                  25                  30

Thr Leu Pro Arg Ser Glu Val Ile Ala Arg Ala Lys Asp Ala Asp Ala
                35                  40                  45

Leu Met Ala Phe Met Pro Asp Ser Ile Asp Ser Ala Phe Leu Glu Glu
            50                  55                  60

Cys Pro Lys Leu Arg Val Ile Gly Ala Ala Leu Lys Gly Tyr Asp Asn
65                  70                  75                  80

Phe Asp Val Asn Ala Cys Thr Arg His Gly Val Trp Leu Thr Ile Val
                85                  90                  95

Pro Asp Leu Leu Thr Ile Pro Thr Ala Glu Leu Thr Ile Gly Leu Leu
                100                 105                 110

Leu Gly Leu Thr Arg His Met Leu Glu Gly Asp Arg Gln Ile Arg Ser
                115                 120                 125

Gly His Phe Gln Gly Trp Arg Pro Thr Leu Tyr Gly Ser Gly Leu Thr
                130                 135                 140

Gly Lys Thr Leu Gly Ile Ile Gly Met Gly Ala Val Gly Arg Ala Ile
145                 150                 155                 160

Ala Gln Arg Leu Ala Gly Phe Glu Met Asn Leu Leu Tyr Cys Ala Arg
                165                 170                 175

Ile Pro Leu Asn Ala Glu Gln Glu Lys Ala Trp His Val Gln Arg Val
                180                 185                 190

Thr Leu Asp Glu Leu Leu Glu Lys Cys Asp Tyr Val Val Pro Met Val
                195                 200                 205

Pro Met Ala Ala Glu Thr Leu His Leu Ile Asp Ala Thr Ala Leu Ala
                210                 215                 220

Lys Met Lys Thr Gly Ser Tyr Leu Ile Asn Ala Cys Arg Gly Ser Val
225                 230                 235                 240

Val Asp Glu Asn Ala Val Ile Ala Ala Leu Ala Ser Gly Lys Leu Ala
                245                 250                 255
```

```
Gly Tyr Ala Ala Asp Val Phe Glu Met Glu Glu Trp Ile Arg Ala Asp
            260                 265                 270
Arg Pro Gln Ala Ile Pro Lys Ala Leu Leu Asp Asn Thr Ala Gln Thr
        275                 280                 285
Phe Phe Thr Pro His Leu Gly Ser Ala Val Lys Glu Val Arg Leu Glu
    290                 295                 300
Ile Glu Arg Gln Ala Ala Met Asn Ile Ile Gln Ala Leu Ala Gly Glu
305                 310                 315                 320
Lys Pro Met Gly Ala Ile Asn Gln Pro Tyr Pro Gly Val Lys Ala Ala
                325                 330                 335

<210> SEQ ID NO 12
<211> LENGTH: 1011
<212> TYPE: DNA
<213> ORGANISM: Ralstonia sp. 4506

<400> SEQUENCE: 12
atgaagccca aagtcgtcct cacccactgg gtgcacccgg aaatcatcga attgttgtcc      60
gctagcgccg atgttatccc caacaccaca cgggaaacct tgccgcgttc tgaggtaatt     120
gcgcgagcca aagatgcgga tgcactcatg gctttcatgc cggacagcat cgacagcgcg     180
tttctcgagg aatgtccaaa gctgcgtgtc atcggcgccg cgcttaaagg ctatgataac     240
ttcgatgtca acgcctgcac acgccacggt gtatggctta cgattgtgcc ggatttgctt     300
acgatcccga ccgctgaact gactatcggc cttcttctcg gtttgacaag gcatatgctg     360
gaaggcgata ggcaaatccg tagcggacac ttccaaggct ggcggccgac actatatggc     420
tctggtttga caggaaaaac gcttggcatc attggtatgg gggcggtcgg ccgtgcaatc     480
gcccagcgct tggctggctt tgaaatgaat ctcttgtatt gcgcaccgat tccgctcaat     540
gccgaacaag aaaaggcttg gcacgtacag gcgcgtcacg ctcgatgaact gctcgaaaaa     600 tgtgattatg tcgtgccgat ggttccgatg gccgcagaga cactgcatct gatcgatgcc     660
accgcgttgg ccaagatgaa aaccggtagc tacctgatca atgcatgtcg cggctcggtc     720
gtggatgaga atgcggtgat agcagcactg gcgtctggaa aactagctgg atatgcagcc     780
gatgtcttcg agatggaaga atggatacgc gctgatcgcc cgcaggctat ccccaaggcg     840
ctgctcgaca atacggcaca aacgttttt acgccgcatt gggatcggc ggtcaaggaa       900 gttcggcttg aaatcgagcg gcaggcagcg atgaacatca tccaggcact cgctggtgaa     960
aaaccgatgg gcgcgattaa tcagccgtat ccgggagtaa aggcggcgtg a             1011

<210> SEQ ID NO 13
<211> LENGTH: 1011
<212> TYPE: DNA
<213> ORGANISM: Ralstonia sp. 4506

<400> SEQUENCE: 13
atgaagccca aagtcgtcct cacccactgg gtgcacccgg aaatcatcga attgttgtcc      60
gctagcgccg atgttatccc caacaccaca cgggaaacct tgccgcgttc tgaggtaatt     120
gcgcgagcca aagatgcgga tgcactcatg gctttcatgc cggacagcat cgacagcgcg     180
tttctcgagg aatgtccaaa gctgcgtgtc atcggcgccg cgcttaaagg ctatgataac     240
ttcgatgtca acgcctgcac acgccacggt gtatggctta cgattgtgcc ggatttgctt     300
acgatcccga ccgctgaact gactatcggc cttcttctcg gtttgacaag gcatatgctg     360
gaaggcgata ggcaaatccg tagcggacac ttccaaggct ggcggccgac actatatggc     420
```

| | |
|---|---|
| tctggtttga caggaaaaac gcttggcatc attggtatgg gggcggtcgg ccgtgcaatc | 480 |
| gcccagcgct tggctggctt tgaaatgaat ctcttgtatt gcgatcgtat tccgctcaat | 540 |
| gccgaacaag aaaaggcttg gcacgtacag cgcgtcacgc tcgatgaact gctcgaaaaa | 600 |
| tgtgattatg tcgtgccgat ggttccgatg gccgcagaga cactgcatct gatcgatgcc | 660 |
| accgcgttgg ccaagatgaa aaccggtagc tacctgatca atgcatgtcg cggctcggtc | 720 |
| gtggatgaga atgcggtgat agcagcactg gcgtctggaa aactagctgg atatgcagcc | 780 |
| gatgtcttcg agatggaaga atggatacgc gctgatcgcc cgcaggctat ccccaaggcg | 840 |
| ctgctcgaca atacggcaca aacgtttttt acgccgcatt tgggatcggc ggtcaaggaa | 900 |
| gttcggcttg aaatcgagcg gcaggcagcg atgaacatca tccaggcact cgctggtgaa | 960 |
| aaaccgatgg gcgcgattaa tcagccgtat ccgggagtaa aggcggcgtg a | 1011 |

<210> SEQ ID NO 14
<211> LENGTH: 1011
<212> TYPE: DNA
<213> ORGANISM: Ralstonia sp. 4506

<400> SEQUENCE: 14

| | |
|---|---|
| atgaagccca aagtcgtcct cacccactgg gtgcacccgg aaatcatcga attgttgtcc | 60 |
| gctagcgccg atgttatccc caacaccaca cgggaaacct tgccgcgttc tgaggtaatt | 120 |
| gcgcgagcca aagatgcgga tgcactcatg ctttcatgc cggacagcat cgacagcgcg | 180 |
| tttctcgagg aatgtccaaa gctgcgtgtc atcggcgccg cgcttaaagg ctatgataac | 240 |
| ttcgatgtca acgcctgcac acgccacggt gtatggctta cgattgtgcc ggatttgctt | 300 |
| acgatcccga ccgctgaact gactatcggc cttcttctcg gtttgacaag gcatatgctg | 360 |
| gaaggcgata ggcaaatccg tagcggacac ttccaaggct ggcggccgac actatatggc | 420 |
| tctggtttga caggaaaaac gcttggcatc attggtatgg gggcggtcgg ccgtgcaatc | 480 |
| gcccagcgct tggctggctt tgaaatgaat ctcttgtatt gcgcacgtat tccgctcaat | 540 |
| gccgaacaag aaaaggcttg gcacgtacag cgcgtcacgc tcgatgaact gctcgaaaaa | 600 |
| tgtgattatg tcgtgccgat ggttccgatg gccgcagaga cactgcatct gatcgatgcc | 660 |
| accgcgttgg ccaagatgaa aaccggtagc tacctgatca atgcatgtcg cggctcggtc | 720 |
| gtggatgaga atgcggtgat agcagcactg gcgtctggaa aactagctgg atatgcagcc | 780 |
| gatgtcttcg agatggaaga atggatacgc gctgatcgcc cgcaggctat ccccaaggcg | 840 |
| ctgctcgaca atacggcaca aacgtttttt acgccgcatt tgggatcggc ggtcaaggaa | 900 |
| gttcggcttg aaatcgagcg gcaggcagcg atgaacatca tccaggcact cgctggtgaa | 960 |
| aaaccgatgg gcgcgattaa tcagccgtat ccgggagtaa aggcggcgtg a | 1011 |

<210> SEQ ID NO 15
<211> LENGTH: 3620
<212> TYPE: DNA
<213> ORGANISM: Ralstonia sp. 4506

<400> SEQUENCE: 15

| | |
|---|---|
| gtgtcatatc acgacattac catcgctgca attcagattc gtaatcaggt catcattttt | 60 |
| gattacgatt tcaaatctgc cggaggtgtc atgatcgaac tacagaatgt ctcagtcagt | 120 |
| tatggtgatg cgattgcact gtatcccacc actctcaaac tccatcaggg acagttcacc | 180 |
| gtattgctcg atcttccgg cgctggaaaa tccacgctac ttcgctgtat taattcgctg | 240 |
| catgcgtcgc agcgcggcac caccattgtc gccggcttag gaaatttggc gaactcgcgt | 300 |

```
gcattgcgca tgcatcgccg acagactggc atggtgtttc aacagcatca attgattggc    360
cgactgacgg ctttgcaaaa cgtttcgatg ggccgaatgg gctaccacac ggcattacgc    420
agtctattcc ccctcccggc gaaggatcaa tccatatgcc tgcaaagtct ggaccgagtc    480
ggcttattgc acaaagcctt aagccgtgtc gacgcattga gcggcggcca gcagcaacgc    540
atcggtattg cccgggctct ggctcagcaa cctaaactgg tgttggctga tgaaccggta    600
gccagcctcg atcctgctac tgcagagcga gtgctaagtc tgctgcaccg catttgtaaa    660
gaggacggga tttcggcggt cgtcagcctg catcaggtag acctcgctca acgttatgcc    720
gaccgtatta ttggcctgtc ccatggccga gtcatttttg atgccgcccc gcagactttg    780
gatcaagcca gttacgacac gctgtatgaa caagtacccc gttcttcttt gagcgttcca    840
caagacgctc gagaggaacg gcttatcgat acttcatttc ccatgcaact tgctaccgta    900
aaggattgat tatgaaaaaa ctcgcatccg cattattgtc tgtcttgctt gccgccgtct    960
gcagcattgg ccatgcatca tccaatcccg atccagaaac gctcaaagtt gcgctgctgc   1020
cggacgaaaa cgcatcgacc gtaattaaaa acaacaagcc gctcgaaatc tatctggaaa   1080
aagagctggg aaagaaaatt gagctggtgg ttaccactga ttactcgtca atgatcgaag   1140
ccatgcgtca cggccgtatc gacatggcat attttggccc cttgtcgtat gtgctggcta   1200
agcaaaagag cgacatcgag ccattcgcag cgatgaagca aaagggtagc actacctacc   1260
agtccgtatt gatcgccaat actggcgccg gcatcgccaa aatcagtgat atcgtcaaca   1320
agaatgtcgc ttacggtgat aaggcatcca cctccagcca tttgattccg aagtcgatat   1380
tggcggaaaa cggttttgaaa gccggcgaaa actatcgcga cactttgtc ggtgcgcatg   1440 acgcggtggc catggccgtg caaaacggtc acgcgcaggc tggcggcttg agtaagccga   1500 ttttgaatc cctggttcag cgcggactgg tcgatcccaa caaagtaaaa gttcttgccg   1560
aatcgaagcc atatccgcaa tacccgtgga ccatgcgcag caatctgaag ccggaactga   1620
aggaaaagat ccgtgcagcc ttcttgaatc tcaaagatcc ggaagtcctg aaaccttca   1680 aagccgatgg tttcggcccg atcagcgaca aagactatga cgtggtgcgc agccttggca   1740
cactgctcaa gctcgatctg tcgaagttct aagtgagcga cagcatgcaa gctgattttg   1800
gtttgattct ggccgagcgc cagcgcgtat ggaaccgcac gatactgcag tttgccgttg   1860
tgctggcgat tgtgatcggt tgctggtatt acgtcggcct atttgatgcc gagcgattga   1920
aggatggcat gccaagcctg gtaaaaattg ccggcgagat gttcccaccg aacttctcgc   1980
aggctggcac ctgggtcaaa ccggtactgg ataccttggc catgagtatc gccggcacgg   2040
caatcgcggt attgctatcc attcccttag gagtgctcgc cgcgcggaat actagccctc   2100
atccactcgt gtatcaagcc acacgcggcc tgttaaacgc tttgcgatcg atacccgaac   2160
tgatcatggg catcctgttc gtggcagccg ttggcttcgg cgcattgccg ggtgttttag   2220
ccctaggctt acattcggtt ggcatgatcg ccaaattttt ttcggaatcg atcgaacatg   2280
ccgatccggc accggtagaa gccgcgcatg cagcgggctg cacgccattg caggtgattt   2340
ttcatgggat ctttccccaa gtgcttccgc aaatggccga taccgcgatc tatcgatggg   2400
aatacaactt ccgtgcttcg accgtgatgg gcatggtcgg cgccggtgga atcgggttcg   2460
agctgatggg ctctctgcgc atcatgcaat accaggatgt ctcggctatt tgctggtta   2520 ttttaggcat ggttaccctc gtcgacgcct tcagctcctt cctgcgtcgc aagttcaaat   2580
aactcccaaa gcttacaaag gttttttatga agcccaaagt cgtcctcacc cactgggtgc   2640
```

```
acccggaaat catcgaattg ttgtccgcta gcgccgatgt tatccccaac accacacggg   2700
aaaccttgcc gcgttctgag gtaattgcgc gagccaaaga tgcggatgca ctcatggctt   2760
tcatgccgga cagcatcgac agcgcgtttc tcgaggaatg tccaaagctg cgtgtcatcg   2820
gcgccgcgct taaaggctat gataacttcg atgtcaacgc ctgcacacgc cacggtgtat   2880
ggcttacgat tgtgccggat ttgcttacga tcccgaccgc tgaactgact atcggccttc   2940
ttctcggttt gacaaggcat atgctggaag gcgataggca aatccgtagc ggacacttcc   3000
aaggctggcg gccgacacta tatggctctg gtttgacagg aaaaacgctt ggcatcattg   3060 gtatggggc ggtcggccgt gcaatcgccc agcgcttggc tggctttgaa atgaatctct   3120
tgtattgcga tccgattccg ctcaatgccg aacaagaaaa ggcttggcac gtacagcgcg   3180
tcacgctcga tgaactgctc gaaaaatgtg attatgtcgt gccgatggtt ccgatggccg   3240
cagagacact gcatctgatc gatgccaccg cgttggccaa gatgaaaacc ggtagctacc   3300
tgatcaatgc atgtcgcggc tcggtcgtgg atgagaatgc ggtgatagca gcactggcgt   3360
ctggaaaact agctggatat gcagccgatg tcttcgagat ggaagaatgg atacgcgctg   3420
atcgcccgca ggctatcccc aaggcgctgc tcgacaatac ggcacaaacg ttttttacgc   3480
cgcatttggg atcggcggtc aaggaagttc ggcttgaaat cgagcggcag gcagcgatga   3540
acatcatcca ggcactcgct ggtgaaaaac cgatgggcgc gattaatcag ccgtatccgg   3600
gagtaaaggc ggcgtgatag                                              3620
```

<210> SEQ ID NO 16
<211> LENGTH: 32
<212> TYPE: DNA
<213> ORGANISM: Artificial Sequence
<220> FEATURE:
<223> OTHER INFORMATION: artificially synthesized primer sequence

<400> SEQUENCE: 16
ggaattctag caggcgtcta tatttggcat ag                                32

<210> SEQ ID NO 17
<211> LENGTH: 33
<212> TYPE: DNA
<213> ORGANISM: Artificial Sequence
<220> FEATURE:
<223> OTHER INFORMATION: artificially synthesized
      primer sequence

<400> SEQUENCE: 17
aaggatccca gatctatcac gccgccttta ctc                               33

<210> SEQ ID NO 18
<211> LENGTH: 30
<212> TYPE: DNA
<213> ORGANISM: Artificial Sequence
<220> FEATURE:
<223> OTHER INFORMATION: artificially synthesized
      primer sequence

<400> SEQUENCE: 18
cgggatccga tgaagcccaa agtcgtcctc                                   30

<210> SEQ ID NO 19
<211> LENGTH: 29
<212> TYPE: DNA
<213> ORGANISM: Artificial Sequence
<220> FEATURE:
<223> OTHER INFORMATION: artificially synthesized primer sequence

<400> SEQUENCE: 19
cggaattcgc cgcctttact cccggatac                                              29

<210> SEQ ID NO 20
<211> LENGTH: 28
<212> TYPE: DNA
<213> ORGANISM: Artificial Sequence
<220> FEATURE:
<223> OTHER INFORMATION: artificially synthesized
      primer sequence

<400> SEQUENCE: 20
ttgcgcacgt attccgctca atgccgaa                                               28

<210> SEQ ID NO 21
<211> LENGTH: 28
<212> TYPE: DNA
<213> ORGANISM: Artificial Sequence
<220> FEATURE:
<223> OTHER INFORMATION: artificially synthesized
      primer sequence

<400> SEQUENCE: 21
ggaatacgtg cgcaatacaa gagattca                                               28

<210> SEQ ID NO 22
<211> LENGTH: 28
<212> TYPE: DNA
<213> ORGANISM: Artificial Sequence
<220> FEATURE:
<223> OTHER INFORMATION: artificially synthesized
      primer sequence

<400> SEQUENCE: 22
ttgcgatcgt attccgctca atgccgaa                                               28

<210> SEQ ID NO 23
<211> LENGTH: 28
<212> TYPE: DNA
<213> ORGANISM: Artificial Sequence
<220> FEATURE:
<223> OTHER INFORMATION: artificially synthesized
      primer sequence

<400> SEQUENCE: 23
ggaatacgat cgcaatacaa gagattca                                               28

<210> SEQ ID NO 24
<211> LENGTH: 28
<212> TYPE: DNA
<213> ORGANISM: Artificial Sequence
<220> FEATURE:
<223> OTHER INFORMATION: artificially synthesized
      primer sequence

<400> SEQUENCE: 24
ttgcgcaccg attccgctca atgccgaa                                               28

<210> SEQ ID NO 25
<211> LENGTH: 28
<212> TYPE: DNA
<213> ORGANISM: Artificial Sequence
<220> FEATURE:
<223> OTHER INFORMATION: artificially synthesized
      primer sequence

<400> SEQUENCE: 25
ggaatcggtg cgcaatacaa gagattca                                              28

<210> SEQ ID NO 26
<211> LENGTH: 35
<212> TYPE: DNA
<213> ORGANISM: Artificial Sequence
<220> FEATURE:
<223> OTHER INFORMATION: artificially synthesized
      primer sequence

<400> SEQUENCE: 26
caccatcatc atatgaagcc caaagtcgtc ctcac                                      35

<210> SEQ ID NO 27
<211> LENGTH: 35
<212> TYPE: DNA
<213> ORGANISM: Artificial Sequence
<220> FEATURE:
<223> OTHER INFORMATION: artificially synthesized
      primer sequence

<400> SEQUENCE: 27
atcatcctta taatctcacg ccgcctttac tcccg                                      35

<210> SEQ ID NO 28
<211> LENGTH: 1011
<212> TYPE: DNA
<213> ORGANISM: Pseudomonas stutzeri

<400> SEQUENCE: 28

| | | | | | |
|---|---|---|---|---|---|
| atgctgccga | aactcgttat | aactcaccga | gtacacgatg | agatcctgca | actgctggcg | 60 |
| ccacattgcg | agctgatgac | caaccagacc | gacagcacgc | tgacgcgcga | ggaaattctg | 120 |
| cgccgctgtc | gcgatgctca | ggcgatgatg | gcgttcatgc | ccgatcgggt | cgatgcagac | 180 |
| tttcttcaag | cctgccctga | gctgcgtgta | gtcggctgcg | cgctcaaggg | cttcgacaat | 240 |
| ttcgatgtgg | acgcctgtac | tgcccgcggg | gtctggctga | ccttcgtgcc | tgatctgttg | 300 |
| acggtcccga | ctgccgagct | ggcgatcgga | ctggcggtgg | ggctggggcg | catctgcgcg | 360 |
| gcagcagatg | cgttcgtccg | ctctggcgag | ttccagggct | ggcaaccaca | gttctacggc | 420 |
| acggggctgg | ataacgctac | ggtcggcatc | cttggcatgg | gcgccatcgg | actggccatg | 480 |
| gctgatcgct | tgcagggatg | gggcgcgacc | ctgcagtacc | acgaggcgaa | ggctctggat | 540 |
| acacaaaccg | agcaacggct | cggcctgcgc | caggtggcgt | gcagcgaact | cttcgccagc | 600 |
| tcggacttca | tcctgctggc | gcttcccttg | aatgccgata | cccagcatct | ggtcaacgcc | 660 |
| gagctgcttg | ccctcgtacg | gccgggcgct | ctgcttgtaa | accccgtgcg | tggttcggta | 720 |
| gtggatgaag | ccgccgtgct | cgcggcgctt | gagcgaggcc | agctcggcgg | gtatgcggcg | 780 |
| gatgtattcg | aaatggaaga | ctgggctcgc | gcggaccggc | cgcggctgat | cgatcctgcg | 840 |
| ctgctcgcgc | atccgaatac | gctgttcact | ccgcacatag | ggtcggcagt | gcgcgcggtg | 900 |
| cgcctggaga | ttgaacgttg | tgcagcgcag | aacatcatcc | aggtattggc | aggtgcgcgc | 960 |
| ccaatcaacg | ctgcgaaccg | tctgcccaag | gccgagcctg | ccgcatgttg | a | 1011 |

<210> SEQ ID NO 29
<211> LENGTH: 336
<212> TYPE: PRT
<213> ORGANISM: Pseudomonas stutzeri

<400> SEQUENCE: 29

```
Met Leu Pro Lys Leu Val Ile Thr His Arg Val His Asp Glu Ile Leu
1               5                   10                  15

Gln Leu Leu Ala Pro His Cys Glu Leu Met Thr Asn Gln Thr Asp Ser
            20                  25                  30

Thr Leu Thr Arg Glu Glu Ile Leu Arg Arg Cys Arg Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Val Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Glu Phe Gln Gly Trp Gln Pro Gln Phe Tyr Gly Thr Gly Leu Asp
    130                 135                 140

Asn Ala Thr Val Gly Ile Leu Gly Met Gly Ala Ile Gly Leu Ala Met
145                 150                 155                 160

Ala Asp Arg Leu Gln Gly Trp Gly Ala Thr Leu Gln Tyr His Glu Ala
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Gln His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Arg Leu Ile Asp Pro Ala Leu Leu Ala His Pro Asn Thr Leu
        275                 280                 285

Phe Thr Pro His Ile Gly Ser Ala Val Arg Ala Val Arg Leu Glu Ile
    290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Glu Pro Ala Ala Cys
                325                 330                 335
```

<210> SEQ ID NO 30
<211> LENGTH: 35
<212> TYPE: DNA
<213> ORGANISM: Artificial Sequence
<220> FEATURE:
<223> OTHER INFORMATION: artificially synthesized
      primer sequence

<400> SEQUENCE: 30
caccatcatc atatgctgcc gaaactcgtt ataac          35

```
<210> SEQ ID NO 31
<211> LENGTH: 36
<212> TYPE: DNA
<213> ORGANISM: Artificial Sequence
<220> FEATURE:
<223> OTHER INFORMATION: artificially synthesized
      primer sequence

<400> SEQUENCE: 31
atcatcctta taatctcaac atgcggcagg ctcggc                               36

<210> SEQ ID NO 32
<211> LENGTH: 26
<212> TYPE: DNA
<213> ORGANISM: Artificial Sequence
<220> FEATURE:
<223> OTHER INFORMATION: artificially synthesized
      primer sequence

<400> SEQUENCE: 32
catatgatga tggtggtgat gcatag                                          26

<210> SEQ ID NO 33
<211> LENGTH: 25
<212> TYPE: DNA
<213> ORGANISM: Artificial Sequence
<220> FEATURE:
<223> OTHER INFORMATION: artificially synthesized
      primer sequence

<400> SEQUENCE: 33
gattataagg atgatgacga taaac                                           25
```

METHOD FOR SELECTIVELY CULTURING MICROORGANISM USING PHOSPHITE DEHYDROGENASE GENE AS MARKER

CROSS-REFERENCE TO RELATED APPLICATIONS:

The present application is a U.S. 371 National Stage Entry of pending International Patent Application No. PCT/JP2013/071569, international filing date Aug. 8, 2013, which claims priority to JP Patent Application No. 2012-177605, filed Aug. 9, 2012, and which claims priority to JP Patent Application No. 2013-031540, filed Feb. 20, 2013, the contents of which are incorporated by reference in their entireties.

TECHNICAL FIELD

The present invention relates to methods for selectively culturing microorganisms using selective markers other than antibiotic-resistance genes. More specifically, the present invention relates to a method for selectively culturing an organism using a phosphite dehydrogenase gene as a selective marker.

BACKGROUND ART

Microorganisms are used for the production of various useful substances such as the production of biofuels. Microbial culture for the production of biofuels and substances is generally premised on the pure culture of a microorganism of interest (hereinafter referred to as "target microorganism"). This requires the sterilization treatment (also referred to as "disinfection treatment". Unless otherwise noted, the words "sterilization" and "disinfection" are treated as synonymous with each other) of culture media and instruments and the use of various drugs such as antibiotic substances for the prevention of contamination with microorganisms other than the target microorganism. In a case where an antibiotic substance is used, pure culture is maintained by introducing an antibiotic-resistance gene into the target microorganism and culturing the target microorganism in a sterilized culture medium containing an antibiotic substance corresponding to the antibiotic-resistance gene. It has long been known that genes resistant to drugs such as ampicillin and tetracycline are used as selective markers (e.g. see Non-patent Literature 1.).

However, a lager culture scale leads to higher costs of input energy for sterilization of culture media and the like and higher costs of equipment for sterilization. Further, a larger culture scale also leads to a problem of higher cost for procuring drugs, such as antibiotic substances, that are added to the culture media. Furthermore, since a waste liquid containing an antibiotic substance fosters the emergence of antibiotic-resistant bacteria, the treatment of a waste liquid containing an antibiotic substance must be strictly performed. This makes it also necessary to take the trouble and cost to treat a waste liquid containing an antibiotic substance.

Further, a conventional culturing method that uses an antibiotic substance may cause a microorganism having an antibiotic-resistance gene to decompose an antibiotic substance contained in a culture medium. It is known that the subculture of such a microorganism having an antibiotic-resistance leads to a decrease in the amount of an antibiotic substance contained in a culture medium and ends up in failure to select the target microorganism.

Meanwhile, as a matter of course, the adoption of an economical culturing method, such as culturing in an open system for simplification of equipment or reducing the number of process steps such as sterilization for cost reduction in a culturing step, makes it impossible to industrially purely culture the target microorganism.

Therefore, the foregoing problem is a major obstacle to the practicability of the production of a substance using a microorganism.

Incidentally, Non-patent Literature 2 discloses isolating a phosphite-oxidation gene or a hypophosphite-oxidation gene from *Pseudomonas stutzeri* by making a cosmid clone of the *P. stutzeri* genome and isolating the gene by using as an index the acquisition by a host cell (*Pseudomonas aeruginosa*) of the capability to utilize phosphorous acid or hypophosphorous acid. However, Non-patent Literature 2, too, does not disclose using a phosphite dehydrogenase gene as a selective marker or selectively culturing the target microorganism while inhibiting the growth of microorganisms other than the target microorganism. It should be noted in Non-patent Literature 2, too, culture is of course performed under sterile conditions. Further, Non-patent Literature 2 makes no mention of a culture medium free of an antibiotic substance, either. Furthermore, Non-patent Literature 2, which discloses a technology for isolating a phosphite dehydrogenase gene, is different in technological thought from the present invention.

CITATION LIST

Non-patent Literature 1

*Nikkei Baio Saishin Yōgo Jiten* (Nikkei Dictionary of Up-to-date Biotechnical Terms), 5th ed., page 846, Nikkei Business Publications, Inc., Sep. 17, 2002.

Non-Patent Literature 2

William W. Metcalf & Ralph S. Wolfe, *Journal of Bacteriology*, Vol. 180, No. 21, 1998, p. 5547-5558.

SUMMARY OF INVENTION

Technical Problem

The present invention has been made in view of the foregoing conventional problems, and it is an object of the present invention to provide a simple and inexpensive method for selectively culturing a microorganism which method makes it possible to selectively culture a target microorganism over a long period of time while inhibiting the growth of microorganisms other than the target microorganism even without using a sterilization operation or an antibiotic substance on a culture system.

Further, it is another object of the present invention to provide a method for selectively culturing a microorganism using a selective marker other than antibiotic-resistance genes (also referred to as "drug resistance genes").

Furthermore, it is still another object of the present invention to provide a method for selectively culturing a microorganism which method is effective in mass culture of the target microorganism.

Solution to Problem

As a result of their diligent study to solve the foregoing problems, the inventors of the present invention found that the foregoing problems can be solved by using a phosphite dehydrogenase gene instead of an antibiotic-resistance gene as a selective marker, thus accomplishing the present invention.

That is, a method for selectively culturing a microorganism according to the present invention includes the step of culturing, in a culture medium containing phosphorous acid as a sole phosphorous source, a microorganism into which a phosphite dehydrogenase gene has been introduced.

Advantageous Effects of Invention

Since only a small minority of microorganisms can utilize phosphorous acid per se, contamination with unintended microorganisms is unlikely even when they are cultured under unsterile conditions. For this reason, the selective culturing method of the present invention makes it possible to reduce the cost of sterilizing a culture system such as a culture medium and a culture apparatus.

Since the method for selectively culturing a microorganism according to the present invention (hereinafter referred to as "selective culturing method of the present invention") does not use an antibiotic-resistance gene as a selective marker, it is not necessary to use an antibiotic substance in culturing the microorganism. This makes it possible to curb the cost of obtaining an antibiotic substance, thus making it possible to curb the cost of raw materials.

Further, since the selective culturing method of the present invention eliminates the need to use an antibiotic substance, there is no problem with the environmental load of a culture waste liquid containing an antibiotic substance (such as the emergence of antibiotic-resistant bacteria). Furthermore, phosphorous acid per se is hardly toxic to organisms. For this reason, the selective culturing method of the present invention makes it possible to reduce the labor and cost of culture waste liquid treatment.

Further, the phosphorous acid that is used for the selective culturing method of the present invention can be easily synthesized by chemical method, and phosphorous acid is contained in high concentrations in waste liquids of surfactant synthesis and metal plating. For this reason, phosphorous acid is easily and inexpensively available. Therefore, the selective culturing method of the present invention makes it possible to curb the cost of raw materials for culture. Further, the selective culturing method of the present invention can be said to be preferable from a point of view of efficient use of waste liquids of surfactant synthesis and metal plating.

It should be noted that the advantageous effects of the selective culturing method of the present invention are more remarkable when the culture scale is larger.

FIG. 2 is a set of photographic diagrams (a) and (b) showing results of verification of the effect of the introduction of ptxABCD into *Escherichia coli* in the Examples, (a) showing a result of culturing, on a morpholinopropane-sulfonic acid plate culture medium (MOPS-Pt (0.5)) containing phosphorous acid (0.5 mM) as a sole phosphorous source, *E. coli* MT2012 into which RsptxABCD/pSTV28 were not introduced, (b) showing a result of culturing, on the same culture medium, *E. coli* MT2012 into which RsptxABCD/pSTV28 has been introduced.

FIG. 3 is a schematic view of the structure of the plasmid vector RsptxABCDmt/pNSHA used in the Examples.

FIG. 4 is a set of photographic diagrams (a) and (b) showing results of verification of the effect of the introduction of ptxABCD into cyanobacteria (*Synechococcus elongates* PCC7942) in the Examples, (a) showing a result of culturing, on a BG-11 culture medium, transformants (controls) obtained by introducing pNSHA into cyanobacteria (*S. elongates* PCC7942), (b) showing a result of culturing, on the same culture medium, transformants obtained by introducing RsptxABCDmt/pNSHA into the same cyanobacteria.

FIG. 5 is a histogram showing results of measurements of phosphite dehydrogenase activity with NAD or NADP as a substrate for both wild-type enzyme and mutant-type enzyme, the legend "WT" representing a result of unmutated wild-type RsPtxD, the legend "D175A/P176R" representing a result for RsPtxD D175A/P176R, the legend "D175A" representing a result for RsPtxD D175A, the legend "P176R" representing a result for RsPtxD P176R.

FIG. 6 is a schematic view of the operon structure of ptxABCD.

FIG. 7 is a graph showing changes over time in $OD_{600}$ of transformants of *E. coli* MG1655 into which RsptxABCDmt/pSTV28 has been introduced and transformants of *E. coli* MG1655 into which only vector pSTV28 has been introduced.

FIG. 8 is a graph showing a change over time in $OD_{600}$ of transformants of *E. coli* MG1655 into which RsptxABCDmt/pSTV28 has been introduced and which are cultured on an unsterilized culture medium and in an open system.

FIG. 9 is a photographic diagram showing a result of agarose gel electrophoresis performed on plasmid DNA prepared from transformants (after primary culture and after second to tenth subcultures) of *E. coli* MG1655 into which RsptxABCDmt/pSTV28 have been introduced.

FIG. 10 is a schematic view of the structure of the plasmid vector RsptxABCDmt/pUC118 used in the Examples.

FIG. 11 is a set of photographic diagrams (a) to (c) showing a result of agarose gel electrophoresis performed on plasmid DNA prepared from transformants (after primary culture and after second to sixth subcultures) of *E. coli* MG1655 into which RsptxABCDmt/pUC118 has been introduced and graphs (a) to (c) showing changes in plasmid content (%) of the transformants due to subculture, (a) showing a result of culturing the transformants on a morpholinopropane-sulfonic acid culture medium (MOPS-Pi, Amp(+)) containing phosphoric acid (0.5 mM) as a sole phosphorous source and further containing ampicillin, (b) showing a result of culturing the transformants on a morpholinopropane-sulfonic acid culture medium (MOPS-Pi, Amp(−)) containing phosphoric acid (0.5 mM) as a sole phosphorous source, (c) showing a result of culturing the transformants on a morpholinopropane-sulfonic acid culture medium (MOPS-Pt) containing phosphorous acid (0.5 mM) as a sole phosphorous source.

FIG. 12 is a graph showing the results in (a), (b), and (c) of FIG. 11 as changes in plasmid content (μg/mL/$OD_{600}$) of the transformants due to subculture.

FIG. 13 is a set of diagrams (a) and (b) showing changes in the percentages of a strain into which ptxD has been introduced with respect to the total bacterial count in the presence of a competitive strain not utilizing phosphorous acid, (a) showing the percentages of the ptxD-introduced strain before culture, (b) showing the percentages of the ptxD-introduced strain after culture.

FIG. 14 is a graph showing results of culturing strains L972 and L975 of fission yeast (*Schizosaccharomyces*

*pombe*) on liquid media for 40 hours, the legend "none" representing a result of culture on a culture medium having no phosphorous source, the legend "Pi" representing a result of culture on a culture medium containing phosphoric acid as a phosphorous source, the legend "Pt" representing a result of culture on a culture medium containing phosphorous acid as a phosphorous source.

Figure 15:
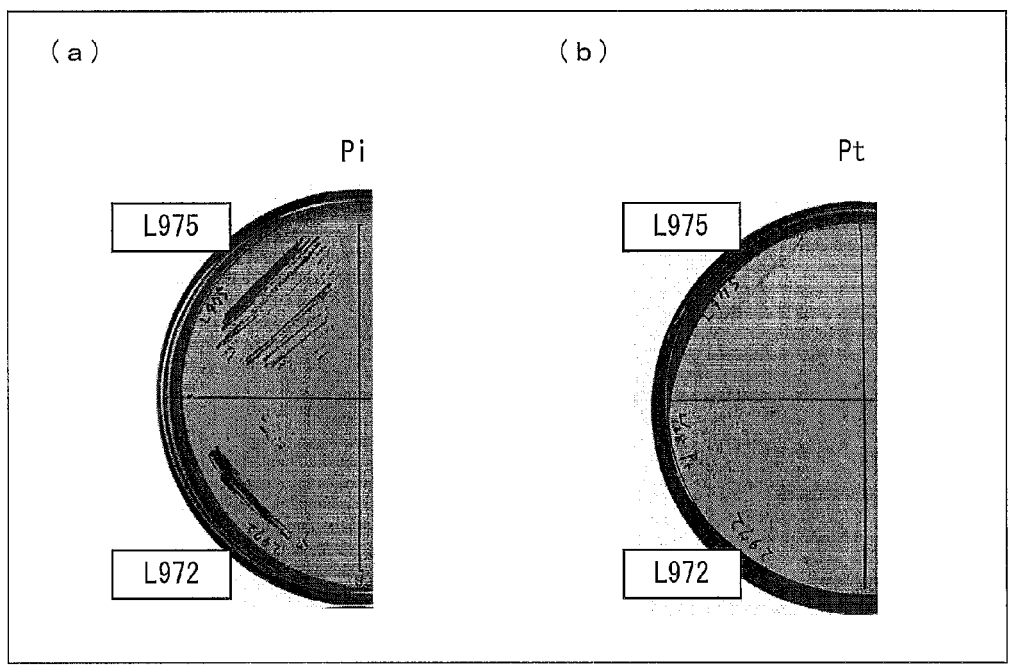

FIG. 15 is a set of photographic diagrams (a) and (b) showing results of culturing strains L972 and L975 of fission yeast on solid media for 4 days, (a) showing a result of culture on a culture medium (Pi) containing phosphoric acid as a phosphorous source, (b) showing a result of culture on a culture medium (Pt) containing phosphorous acid as a phosphorous source.

Figure 16:
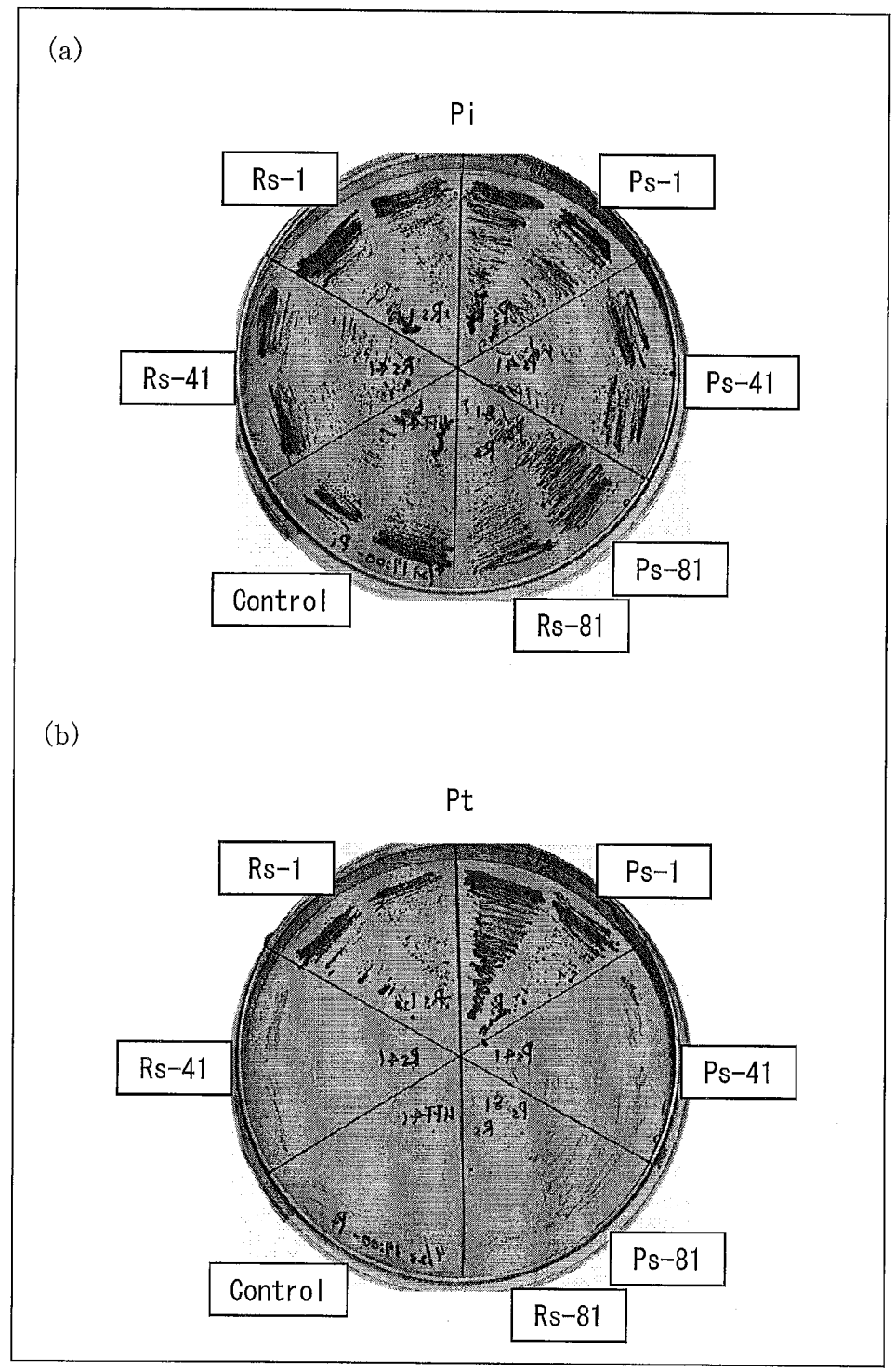

FIG. 16 is a set of photographic diagrams (a) and (b) showing results of culturing transformants of fission yeast on solid media, (a) showing a result of culture on a culture medium (Pi) containing phosphoric acid as a phosphorous source, (b) showing a result of culture on a culture medium (Pt) containing phosphorous acid as a phosphorous source, the legend "Rs-1" representing an RsPtxD/HFF1-introduced strain, the legend "Rs-41" representing an RsPtxD/HFF41-introduced strain, the legend "Rs-81" representing an RsPtxD/HFF81-introduced strain, the legend "Ps-1" representing a PsPtxD/HFF1-introduced strain, the legend "Ps-41" representing a PsPtxD/HFF41-introduced strain, the legend "Ps-81" representing a PsPtxD/HFF81-introduced strain, the legend "Control" representing a pDUAL-HFF41-introduced strain.

Figure 17:
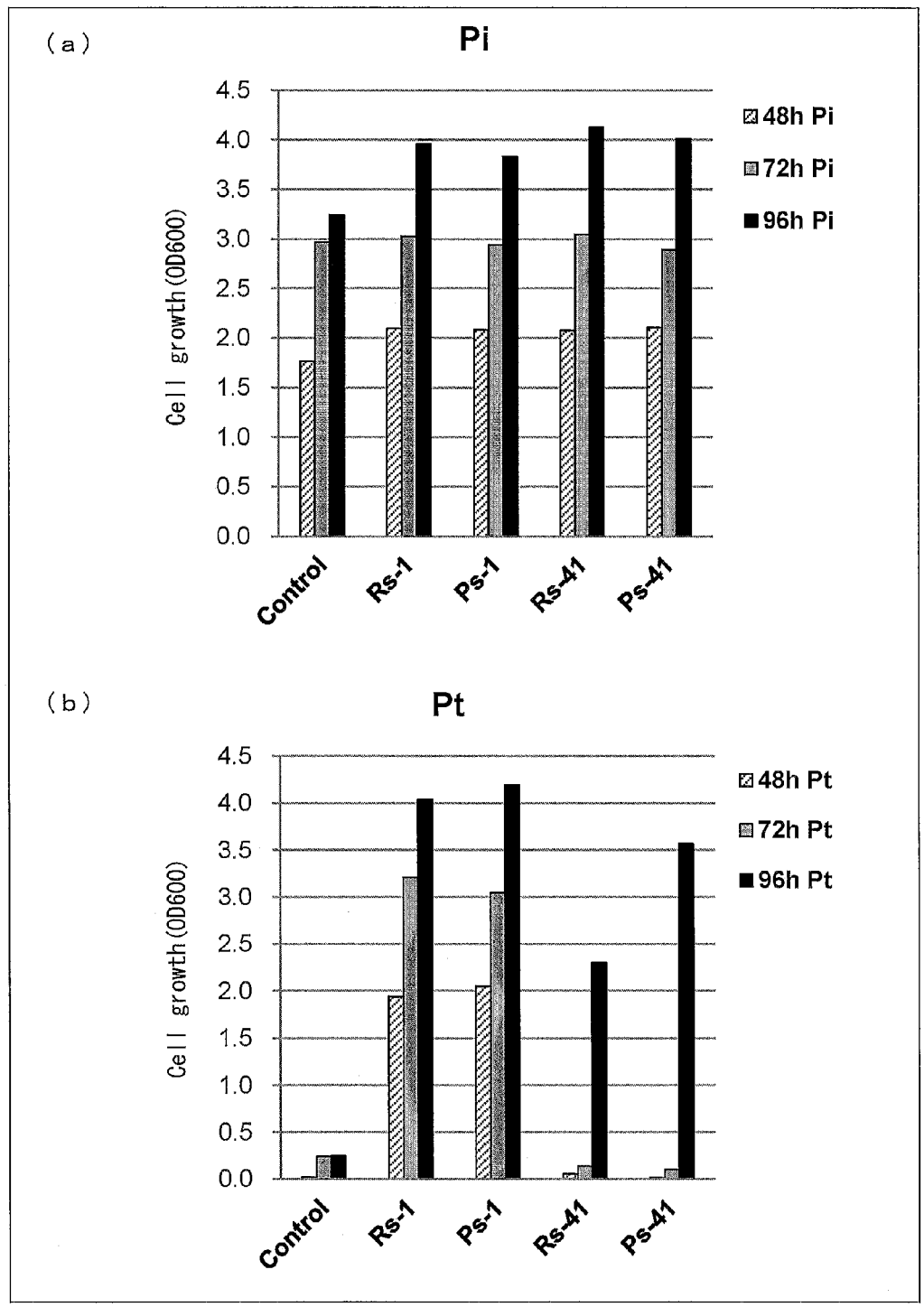

FIG. 17 is a set of graphs (a) and (b) showing results of culturing transformants of fission yeast on liquid media, (a) showing a result of culture on a culture medium (Pi) containing phosphoric acid as a phosphorous source, (b) showing a result of culture on a culture medium (Pt) containing phosphorous acid as a phosphorous source, the legend "Rs-1" representing an RsPtxD/HFF1-introduced strain, the legend "Rs-41" representing an RsPtxD/HFF41-introduced strain, the legend "Ps-1" representing a PsPtxD/HFF1-introduced strain, the legend "Ps-41" representing a PsPtxD/HFF41-introduced strain, the legend "Control" representing a pDUAL-HFF41-introduced strain.

Figure 18:
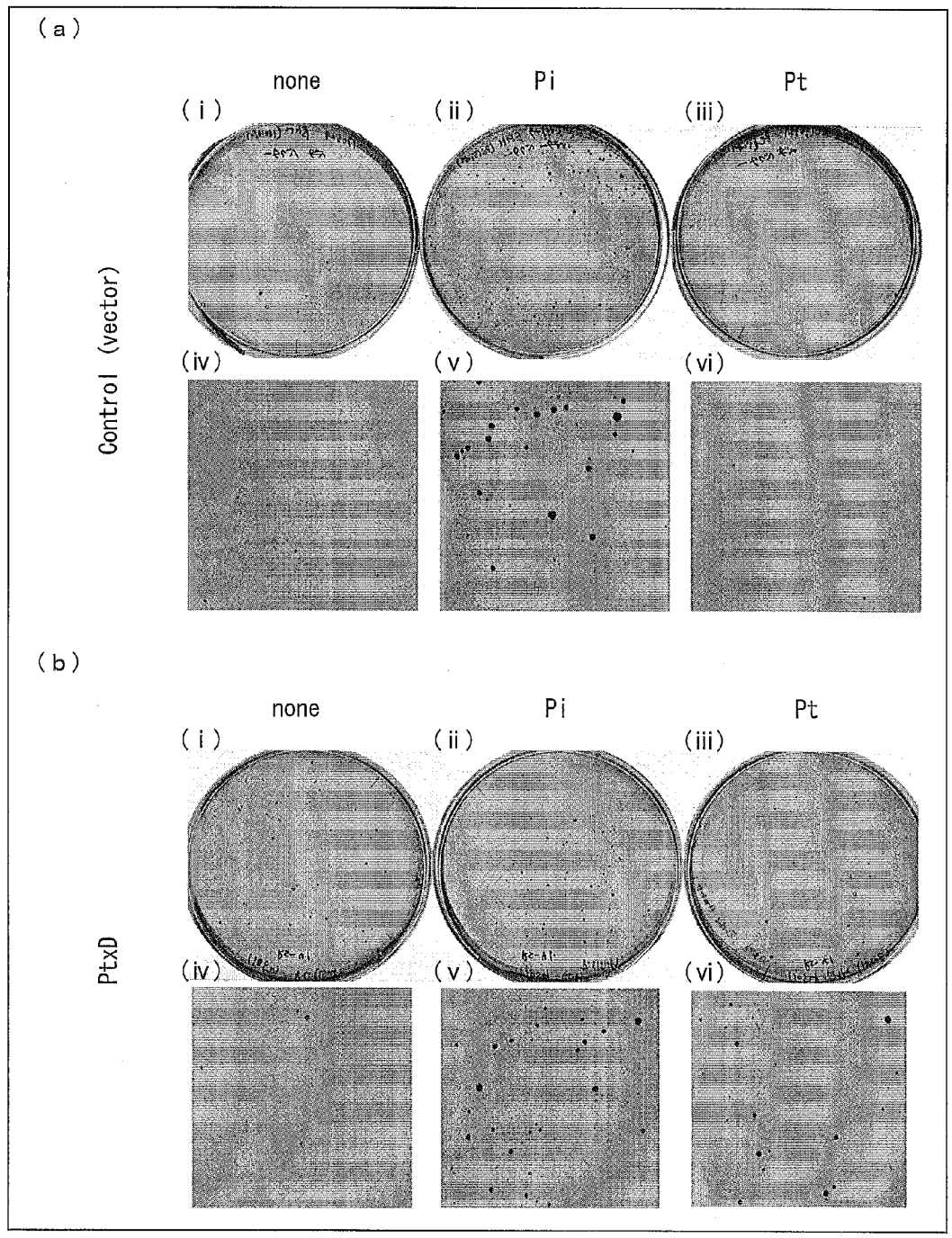

FIG. 18 is a set of photographic diagrams (a) and (b) showing results of culturing transformants of fission yeast on solid media, (a) showing results for transformants into which a control plasmid has been introduced, (b) showing results of transformants into which RsPtxD/HFF1 plasmid has been introduced, in each of the photographic diagrams (a) and (b), (i) showing a result of culture on a culture medium (none) having no phosphorous source, (ii) showing a result of culture on a culture medium (Pi) containing phosphoric acid as a phosphorous source, (iii) showing a result of culture on a culture medium (Pt) containing phosphorous acid as a phosphorous source, (iv), (v), and (vi) showing enlarged views of (i), (ii), and (iii) respectively.

Figure 19:
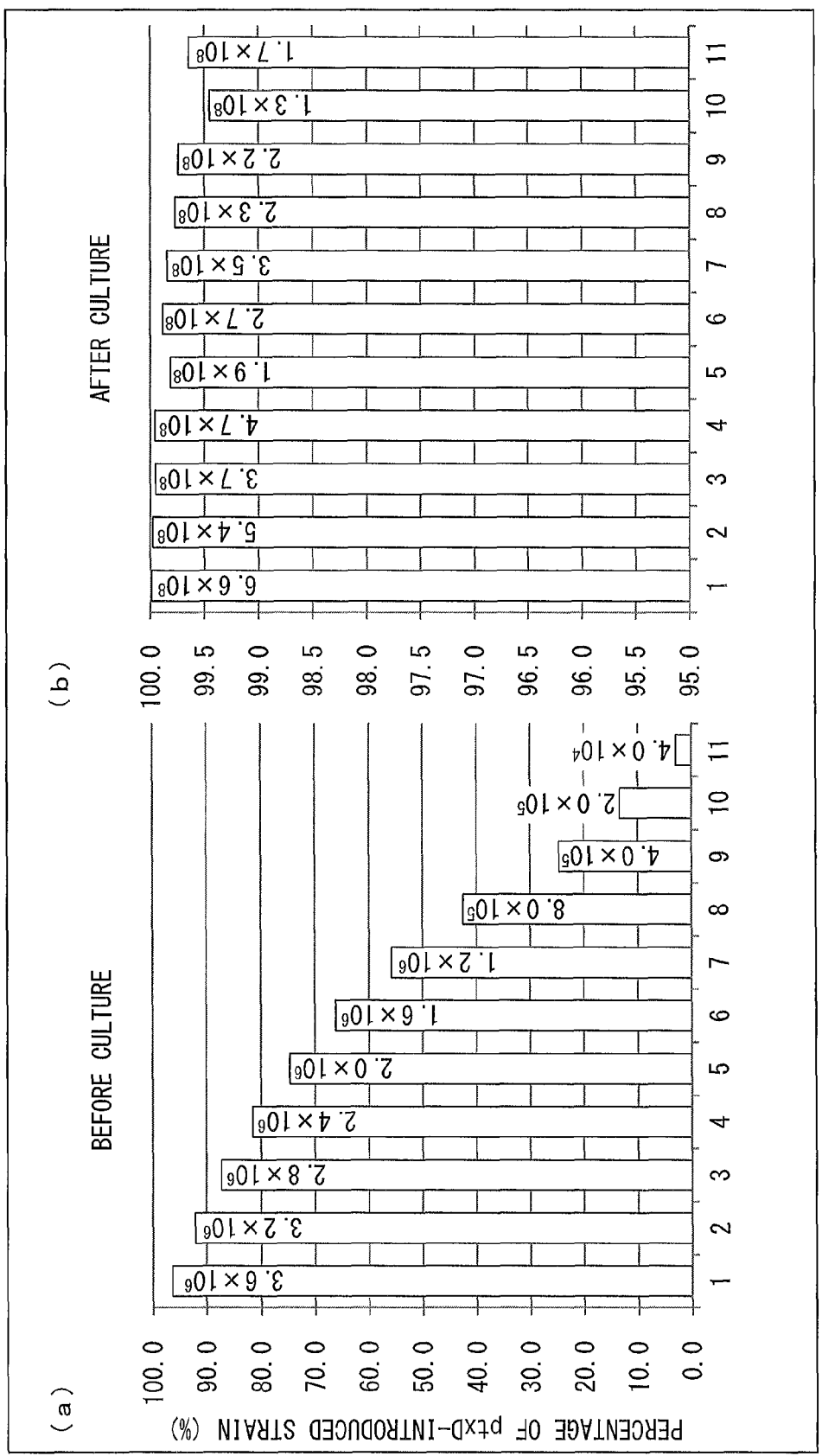

FIG. 19 is a set of diagrams (a) and (b) showing changes in the percentage of a strain into which ptxD has been introduced with respect to the total bacterial count in the presence of a competitive strain not utilizing phosphorous acid, (a) showing the percentages of the ptxD-introduced strain before culture, (b) showing the percentages of the ptxD-introduced strain after culture.

Figure 20:
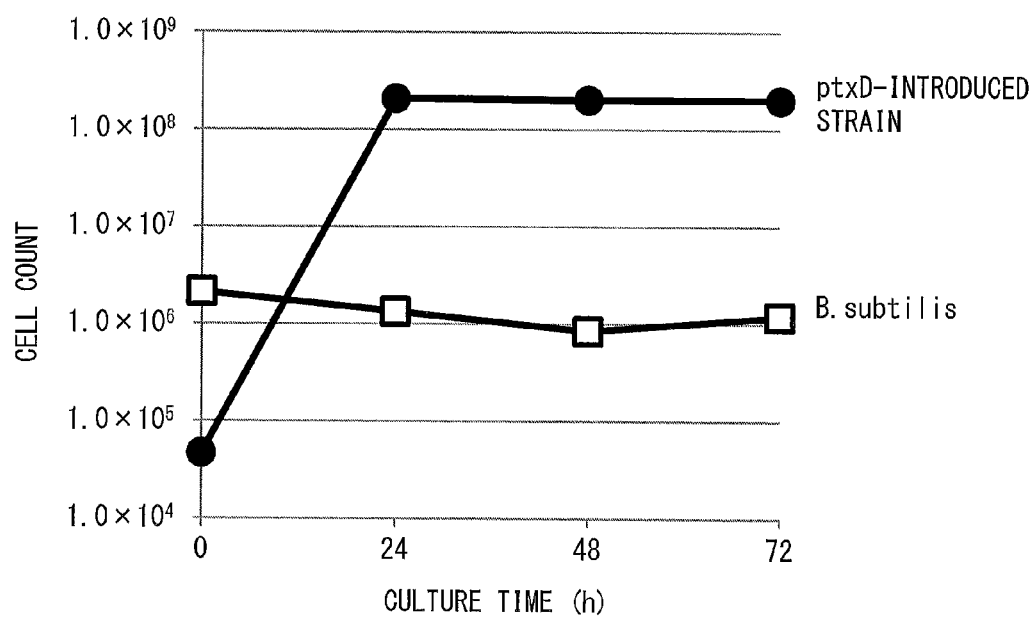

FIG. 20 is a diagram showing changes in the cell count of a competitive strains not utilizing phosphorous acid and a strain into which ptxD has been introduced, the changes occurring in the presence of the competitive strain not utilizing phosphorous acid.

DESCRIPTION OF EMBODIMENTS

An embodiment of the present invention is described below. Note, however, that the present invention is not limited to this embodiment.

[1. Method for Selectively Culturing a Microorganism]

The present invention relates to a method for selectively culturing a microorganism, including the step of culturing, in a culture medium containing phosphorous acid as a sole phosphorous source, a microorganism into which a phosphite dehydrogenase gene has been introduced. The method for selectively culturing a microorganism according to the present invention is herein referred to as needed as "selective culturing method of the present invention".

The "method for selectively culturing a microorganism" here means selectively (preferentially) culturing only the target microorganism while inhibiting the growth of unintended microorganisms, and is further meant to also encompass preferentially culturing the target microorganism. In other words, the selective culturing method of the present invention is preferably configured to culture only the target microorganism. However, this does not imply any limitation. The selective culturing method of the present invention needs only be configured to preferentially culture the target microorganism over microorganisms other than the target microorganism. Further, the target microorganism may be a single microorganism or be composed of plural types of microorganism.

The selective culturing method of the present invention is meant to selectively culture the target microorganism by inoculating inocula of the target microorganism into a culture medium under such conditions that microorganisms other than the target microorganism can exist. While it is being said to be industrially unsterile, it is known that contamination often occurs. The selective culturing method of the present invention includes selectively culturing the target microorganism while intentionally inoculating unintended microorganisms into the culture medium on the supposition that microorganisms other than the target microorganism can exist. However, the selective culturing method of the present invention also includes selectively culture only a strain of the target microorganism into which a phosphite dehydrogenase gene has been introduced.

From a point of view of reducing the cost required for sterilization treatment, it is preferable to selectively culture the target microorganism by inoculating it into a culture medium under unsterile conditions. However, as a matter of course, contamination with microorganisms other that the target microorganisms can be more surely prevented by employing the selective culturing method of the present invention under sterile conditions. For industrially surer safety, it may be preferable to employ the selective culturing method of the present invention under sterile conditions. That is, the selective culturing method of the present invention is a culturing method that makes it possible to selectively culture the microorganism both under sterile conditions and unsterile conditions.

Further, the selective culturing method of the present invention may include an inoculum culturing step ("preculture step) of culturing inocula of the target microorganism.

The selective culturing method of the present invention uses a microorganism into which a phosphite dehydrogenase gene has been introduced. The target microorganism that is used for the selective culturing method of the present invention may be a microorganism having no phosphite dehydrogenase or may be a microorganism having a phosphite dehydrogenase by nature. Further, the selective culturing method of the present invention can be applied to all microorganisms in which phosphite dehydrogenase genes are expressed and can function. Examples of the target microorganism include, but are not particularly limited to, bacteria, yeast (fission yeast or budding yeast), mold, actinomycetes, algae, archaebacteria, etc. It should be noted that the target microorganism may be a microorganism having no phosphite dehydrogenase or may be a microorganism having a phosphite dehydrogenase by nature.

From a point of view of ease of expression of a phosphite dehydrogenase, the present invention needs only select, but is not particularly limited to, a target microorganism according to what a phosphite dehydrogenase is derived from. For example, in a case where the after-mentioned bacteria-derived phosphite dehydrogenase (RsPtxD) is applied to the selective culturing method of the present invention, it is preferable that the target microorganism be bacteria.

A gist of the selective culturing method of the present invention is to use a phosphite dehydrogenase as a selective marker. While phosphorus is an element essential for the growth of living organisms, only a small minority of microorganisms can utilize phosphorous acid per se; therefore, culturing the target microorganism on a culture medium containing phosphorous acid as a sole phosphorous source gives an extremely low possibility of the growth of microorganisms other than the target microorganism even if they are cultured with an unsterilized culture media. For this reason, contamination with microorganisms other than the target microorganism is unlikely. For this reason, the selective culturing method of the present invention can achieve the selective culture of the target microorganism.

It should be noted here that it is preferable that the "unsterile conditions" be conditions under which sterilization treatment such as heat sterilization, filter sterilization, UV irradiation, or ozone irradiation has not been performed at all on a culture system (culture medium, culture apparatus, gas to be supplied (such as oxygen)). The unsterile conditions are meant to encompass open-system culture. It should be noted that in the selective culturing method of the present invention, the culture may be performed under unsterile conditions throughout all of the steps, or the inoculum culturing step (preculture step) may be performed under sterile conditions.

The unsterile conditions may be substantially unsterile conditions. That is, sterilization treatment such as heat sterilization, filter sterilization, UV irradiation, or ozone irradiation may be performed at a lower level of sterilization than normal sterilization treatment aimed at complete sterilization. Examples of sterilization treatment that is performed at a lower level of sterilization than normal sterilization treatment include heat treatment that is performed at a temperature of lower than 100° C., lower than 90° C., or lower than 80° C. for a period of time shorter than 30 minutes, shorter than 20 minutes, or shorter than 10 minutes, etc.

The selective culturing method of the present invention is a culturing method that makes it possible to selectively culture the microorganism over a long period of time both under sterile conditions and unsterile conditions. As used herein, the phrase "makes it possible to selectively culture the microorganism over a long period of time" means selectively culturing the target microorganism while inhibiting the growth of microorganisms other than the target microorganism, for example, over a period of time of 15 hours or longer, 24 hours or longer, 48 hours or longer, or 72 hours or longer.

The term "culture medium containing phosphorous acid as a sole phosphorous source" here means a culture medium substantially not containing a component (e.g. phosphoric acid, hypophosphorous acid, or phosphine, etc.) that supplies a phosphorous source other than phosphorous acid. As used herein, the term "substantially not containing" means a concentration of 100 µM or lower, more preferably 10 µM or lower. The "culture medium" is not particularly limited, provided it contains phosphorous acid as a sole phosphorous source, and needs only be selected as appropriate according to the target microorganism. However, from a point of view of ease of controlling the phosphorous source to phosphorous acid, it is preferable that the "culture medium" be a complete synthetic culture medium. In the Examples below, a morpholinopropane-sulfonic acid culture medium (MOPS culture medium) was used.

Since the selective culturing method of the present invention does not use an antibiotic substance (such as streptomycin, tetracycline, or ampicillin) as a selective marker, the culture medium does not need contain an antibiotic substance. For this reason, an unsterilized culture medium that is applied to the selective culturing method of the present invention can be a culture medium substantially not containing an antibiotic substance.

Further, as mentioned earlier, the advantageous effects of the selective culturing method of the present invention are more remarkable when the culture scale is larger. For this reason, it is preferable that the selective culturing method of the present invention be carried out using 10 L or more (preferably 100 L or more, more preferably 1000 L or more, even more preferably 5000 L or more, most preferably 10000 L or more) of an unsterilized culture medium.

Further, since, as mentioned above, the selective culturing method of the present invention uses a phosphite dehydrogenase as a selective marker, contamination with microorganisms other than the target microorganism is unlikely in the first place. For this reason, the selective culturing method of the present invention may be carried out in an open system whose culture tank is not hermetically closed. The selective culturing method of the present invention can be more easily carried out when carried out in an open system. Further, since the culture apparatus has a comparatively simple structure therefore costs less, it becomes easy to make the culture scale larger.

For the purpose of making contamination more unlikely than in an open system and making it difficult for the target microorganism to be diffused into the natural world, the selective culturing method of the present invention may be carried out in a closed system whose culture tank is hermetically closed.

It should be noted that culturing conditions such as a culture medium, temperature, ventilation conditions, etc. for the selective culturing method of the present invention need only be selected as appropriate according to the target microorganism.

[2. Phosphite Dehydrogenase and a Phosphite Dehydrogenase Gene]

The selective culturing method of the present invention uses a microorganism into which a phosphite dehydrogenase gene has been introduced. As used herein, the term "microorganism into which a phosphite dehydrogenase gene has been introduced" encompasses a recombinant microorganism into which a phosphite dehydrogenase gene has been introduced. Since the selective culturing method of the present invention needs only use a microorganism into which a phosphite dehydrogenase gene has already been introduced, it does not particularly need to include a step (referred to as "gene introducing step") of introducing a phosphite dehydrogenase gene into a microorganism, but may include the gene introducing step.

The gene introducing step needs only include preparing an expression vector containing a phosphite dehydrogenase gene by a publicly-known method and introducing the expression vector into the target microorganism by a publicly-known method. Examples of the expression vector include plasmids such as pSTV28, pNSHA, pUC118, pET, and pGEX. The expression vector can be constructed by coupling a phosphite dehydrogenase gene under control of a promoter that functions in the target microorganism serving as a host. Further, in addition to the promoter, the expression vector may contain a sequence necessary for the expression of a phosphite dehydrogenase gene, an antibiotic-resistance gene (drug resistance gene), etc. Further, as will be mentioned later, the expression vector may contain a phosphite transporter gene.

Furthermore, the expression vector can contain a gene encoding a protein (target protein) that is to be produced in the target microorganism. In this case, it is preferable that the gene encoding the target protein be coupled under control of a promoter that functions in the target microorganism. This makes it possible to cause the target microorganism to produce a protein that the target microorganism does not produce by nature.

A preferred method for introducing a gene in the gene introducing step may be applied according to the type of target microorganism serving as a host. Appropriately applicable examples include electroporation, a calcium phosphate method, a liposome method, a DEAE dextran method, etc.

As above, the gene introducing step of the selective culturing method of the present invention is a step that can be easily executed on the basis of general common technical knowledge that a person skilled in the art possesses.

However, the selective culturing method of the present invention can increase the number of copies of a plasmid containing a phosphite dehydrogenase gene and, even after subculture, can stably maintain the number of copies of the plasmid of interest. That is, the foregoing configuration makes it possible to stably maintain a state where the number of copies of the plasmid is large. Therefore, the selective culturing method of the present invention makes it possible to more efficiently selectively culture the target microorganism. This was first found by the inventors of the present invention.

In the selective culturing method of the present invention, to "increase the number of copies of a plasmid containing a phosphite dehydrogenase gene" means that the number of copies of a plasmid containing a phosphite dehydrogenase gene is larger when the microorganism is cultured with phosphorous acid than when cultured on a culture medium containing phosphoric acid as a sole phosphorous source. Furthermore, the selective culturing method of the present invention can make the number of copies of a plasmid containing a phosphite dehydrogenase gene larger than in a case where the microorganism is cultured by a conventional selective culturing method using an antibiotic substance as a selective marker (i.e. a culturing method using a culture medium containing phosphoric acid as a sole phosphorous source and further containing an antibiotic substance).

Further, to "stably maintain the number of copies of the plasmid" means that for example, in a case where the microorganism is subcultured (e.g. a case where the microorganism is subcultured five, six, seven, eight, nine, ten or more times), 80% or more (more preferably 90% or more) of the number after primary culture of copies of the plasmid containing a phosphite dehydrogenase gene can be maintained.

In a case where an expression vector containing the phosphite dehydrogenase gene and the gene encoding the target protein has been introduced into the microorganism, the selective culturing method of the present invention makes it possible to highly express the gene encoding the target protein. This makes it possible to cause the target microorganism to stably produce the protein that the target microorganism does not produce by nature.

In a case where a plasmid containing a phosphite dehydrogenase gene is used an expression vector, the selective culturing method of the present invention makes it possible to retain the plasmid, for example, at 1.0 to 100 μg/mL/$OD_{600}$.

As used herein, the term "gene" is used interchangeably with "polynucleotide", "nucleic acid", or "nucleic acid molecule", and is intended to mean a nucleotide polymer.

A phosphite dehydrogenase protein (hereinafter denoted by "PtxD" as appropriate) encoded by a phosphite dehydrogenase gene (hereinafter denoted by "ptxD" as appropriate) that is used for the selective culturing method of the present invention is a protein that some bacteria possess but common plants do not possess by nature. As used herein, the wording "phosphite dehydrogenase" means a phosphite dehydrogenase protein unless otherwise noted.

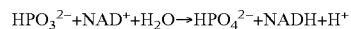

$$HPO_3^{2-} + NAD^+ + H_2O \rightarrow HPO_4^{2-} + NADH + H^+$$

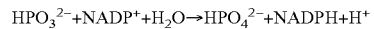

$$HPO_3^{2-} + NADP^+ + H_2O \rightarrow HPO_4^{2-} + NADPH + H^+$$

Since phosphorous acid has an extremely low oxidation-reduction potential and this reaction is a very big exergonic reaction and irreversibly progresses, a phosphite dehydrogenase has drawn attention industrially as a regenerating enzyme for NADH or NADPH.

Figure 6:
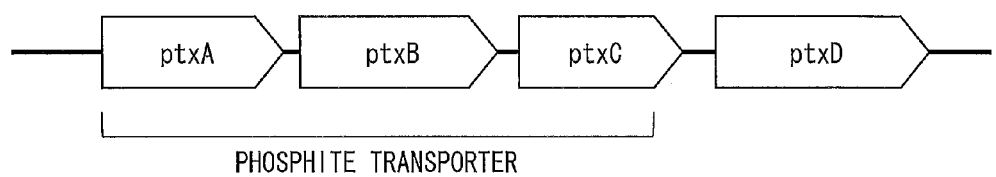

As mentioned earlier, the inventors of the present invention have so far isolated *Ralstonia* sp. strain 4506, which exhibits excellent growth on a phosphorous acid culture medium, in a soil enrichment culture system and obtained PtxD from strain 4506 (Refer to Hirota et al., *J. Biosci. Bioeng.*, Vol. 113, 445-450, 2012.). The inventors of the present invention demonstrated that PtxD derived from strain 4506 has the highest specific activity of all of the phosphite dehydrogenases ever cloned, and filed a patent application therefor (International Publication Number: WO/2012/147556). The phosphite dehydrogenase gene is known to form an operon structure with phosphite transporter genes (ptxA, ptxB, and ptxC) (See FIG. 6.). The phosphite transporter and the phosphite transporter genes will be described in the next section. As used herein, the wording "phosphite transporter" means a phosphite transporter protein unless otherwise noted.

As used herein, a phosphite dehydrogenase derived from strain 4506 and a gene encoding it are denoted by "RsPtxD" and "RsptxD", respectively. Further, a phosphite transporter (constituted by PtxA, PtxB, and PtxC) and a gene (ptxA, ptxB, ptxC) encoding it are denoted by "PtxABC" and "ptxABC", respectively. In particular, a phosphite transporter derived from strain 4506 and a gene encoding it are denoted by "RsPtxABC" and "RsptxABC", respectively. It should be noted that the wordings "ptxABCD" and "RsptxABCD" each mean a gene containing a phosphite transporter gene and a phosphite dehydrogenase gene.

A phosphite dehydrogenase that is used for the selective culturing method of the present invention is not particularly limited, provided it is an enzyme that functions in a microorganism into which it is introduced. Examples of phosphite dehydrogenases that can be used for the selective culturing method of the present invention include the phosphite dehydrogenase derived from strain 4506, a phosphite dehydrogenase derived from *Pseudomonas stutzeri* WM88 (Refer to WO 2010/058298 A2), phosphite dehydrogenases derived from *Desulfotignum phosphitoxidans, Dietzia cinnamea, Methylobacterium extorquens, Comamonas testosterone, Acidovorax ebreus, Cupriavidus metallidurans, Thioalkalivibrio* sp., *Klebsiella pneumoniae, Pseudomonas aeruginosa, Marinobacter algicola, Marinobacter aquaeolei, Shewanella putrefaciens, Prochlorococcus* sp., *Cyanothece* sp., *Trichodesmium erythraeum, Nostoc* sp., *Nodularia spumigena, Nostoc punctiforme, Gallionella capsiferriformans, Burkholderia vietnamiensis, Acinetobacter radioresistens, Herminiimonas arsenicoxydans, Alcaligenes faecalis, Oxalobacter formigenes*, etc. However, for high thermal stability, specific activity, etc. of enzyme, RsPtxD and RsptxD, which encodes RsPtxD, are suitably used.

RsptxD can be a polynucleotide encoding a protein of (a) or (b):

(a) a protein consisting of the amino acid sequence of SEQ ID NO: 1; and (b) a protein consisting of an amino acid with a deletion, substitution, or addition of one or several amino acids in the amino acid sequence of SEQ ID NO: 1 and having phosphite dehydrogenase activity.

RsPtxD is a phosphite dehydrogenase protein having advantages of (i) being able to be expressed in large quantities in soluble state in an *E. coli* host, (ii) having high thermal stability, and (iii) having activity that is hardly inhibited by any of various inhibitors (International Publication Number: WO/2012/147556).

Therefore, in a case where RsptxD is applied to the selective culturing method of the present invention, an expression level of a phosphite dehydrogenase protein in the host microorganism is high, so that it becomes easier to carry out the selective culture of the target microorganism. Further, in a case where RsptxD is applied to the selective culturing method of the present invention, thermal stability of enzyme is high, so that the selective culturing method can also be carried out on a microorganism that grows under high-temperature conditions. Further, in a case where RsptxD is applied to the selective culturing method of the present invention, the selective culturing method can also be carried out under conditions where various inhibitors are present in the culture medium.

The phosphite dehydrogenase gene needs only be one encoding a phosphite dehydrogenase and, without being limited to a single type of nucleotide sequence, can be substituted by another codon encoding the same amino acid.

As used herein, "an amino acid with a deletion, substitution, or addition of one or several amino acids" is not limited in terms of the position where such a deletion, substitution, or addition occurs. It should be noted here that "one or several amino acids" are not meant to be limited to any particular number of amino acids, but are preferably ten or less amino acids, more preferably eight or less amino acids, even more preferably six or less amino acids, even more preferably four or less amino acids, even more preferably two or less amino acids, most preferably one amino acid.

It is preferable that a substitution of an amino acid be a conservative substitution. The term "conservative substitution" refers to a substitution of a particular amino acid by another amino acid having a chemical property and/or a structure that is/are similar to that/those of the particular amino acid. Examples of the chemical property include a degree of hydrophobicity (hydrophobicity and hydrophilicity) and electric charge (neutrality, acidity, and basicity). Examples of the structure include an aromatic ring, an aliphatic hydrocarbon group, and a carboxyl group that are present as a side chain or a functional group of a side chain.

With use of such classification, a conservative substitution can be said to be a substitution between amino acids in the same group, and examples of conservative substitutions include a substitution between serine and threonine, a substitution between lysine and arginine, and a substitution between phenylalanine and tryptophan.

A phosphite dehydrogenase protein encoded by the phosphite dehydrogenase gene may be a protein (i) consisting of an amino acid sequence having a homology of 80% or higher, more preferably 85% or higher, more preferably 90% or higher, more preferably 95% or higher, most preferably 98% or higher, with the phosphite dehydrogenase and (ii) having phosphite dehydrogenase activity.

It should be noted that a homology of amino acid sequences can be found by a publicly-known method. Specifically, a homology can be calculated as the percentage (%) of identical amino acid sequences by performing a homology search of the amino acid sequence of SEQ ID NO: 1, for example, and a comparative amino acid sequence by using GENETYX-WIN (manufactured by Genetyx Corporation) according to the GENETYX-WIN manual.

Alternatively, RsptxD can be a polynucleotide of (c) or (d):

(c) a polynucleotide consisting of the nucleotide sequence of SEQ ID NO: 2; and (d) a polynucleotide that hybridizes under stringent conditions with a nucleotide sequence complementary to a polynucleotide consisting of the nucleotide sequence of SEQ ID NO: 2 and that encodes a phosphite dehydrogenase protein.

The polynucleotide consisting of the nucleotide sequence of SEQ ID NO: 2 is a polynucleotide encoding a protein consisting of the amino acid sequence of SEQ ID NO: 1.

As used herein, the term "stringent conditions" means overnight incubation at 42° C. in a hybridization solution (50% formamide, 5×SSC (150 mM NaCl, 15 mM trisodium citrate), 50 mM sodium phosphate (pH 7.6), 5× Denhardt's solution, 10% dextran sulfate, and 20 µg/mL denatured sheared salmon sperm DNA), followed by washing the filters in 0.1×SSC at about 65° C. High stringency wash conditions are adjusted appropriately in accordance with a polynucleotide to be hybridized. For example, in a case where DNA derived from a mammal is used, the filters are preferably washed in 0.5×SSC containing 0.1% SDS at 65° C. (preferably 15 min.×2 times). In a case where DNA derived from *E. coli* is used, the filters are preferably washed in 0.1×SSC containing 0.1% SDS at 68° C. (preferably 15 min.×2 times). In a case where RNA is used, the filters are preferably washed in 0.1×SSC containing 0.1% SDS at 68° C. (preferably 15 min.×2 times). In a case where an oligonucleotide is used, the filters are preferably washed in 0.1×SSC containing 0.1% SDS at a hybridization temperature (preferably 15 min.×2 times). The hybridization can be carried out in accordance with a well-known method described in Sambrook et al.: Molecular Cloning, A Laboratory Manual, 2d Ed., Cold Spring Harbor Laboratory (1989).

An additional nucleotide sequence can be coupled to the phosphite dehydrogenase gene. It should be noted that the additional nucleotide sequence may be coupled to the 5'- or 3'-end of the phosphite dehydrogenase gene, and is not limited in terms of the position to which it is coupled.

The additional nucleotide sequence is not limited in terms of its specific configuration, but can be a nucleotide sequence encoding a tag or the like (e.g. His tag, Myc tag, HA tag, GST protein, GFP, CFP, or YFP).

The foregoing description concerns "Phosphite Dehydrogenase Gene" but, as for the common items, can be incorporated as appropriate in the description of "Phosphite Transporter Gene" given in the next section.

[3. Phosphite Transporter and a Phosphite Transporter Gene]

The description given in the previous section demonstrated that the advantageous effects of the selective culturing method of the present invention are brought about by using a target microorganism into which at least a phosphite dehydrogenase has been introduced. However, in the selective culturing method of the present invention, there is a case where it is preferable that the target microorganism be one into which a phosphite dehydrogenase gene and a phosphite transporter gene have been introduced. In a case where the target microorganism has no (or low) capability to take up phosphorous acid, phosphorous acid serving as the sole phosphorous source in the culture medium cannot be efficiently taken up into the bacterial cells, with the result that the target microorganism may multiply slowly. In this case, the problem can be prevented in advance by using a target microorganism into which a phosphite dehydrogenase gene and a phosphite transporter gene have been introduced.

A phosphite transporter that can be used for the selective culturing method of the present invention is not particularly limited, provided it is one that functions in the target microorganism. Therefore, a publicly-known phosphite transporter can be used. Examples of phosphite transporters that can be used as appropriate include phosphite transporters derived from *Pseudomonas stutzeri, Desulfotignum phosphitoxidans, Dietzia cinnamea, Methylobacterium extorquens, Comamonas testosterone, Acidovorax ebreus, Cupriavidus metallidurans, Thioalkalivibrio* sp., *Klebsiella pneumoniae, Pseudomonas aeruginosa, Marinobacter algicola, Marinobacter aquaeolei, Shewanella putrefaciens, Prochlorococcus* sp., *Cyanothece* sp., *Trichodesmium erythraeum, Nostoc* sp., *Nodularia spumigena, Nostoc punctiforme, Gallionella capsiferriformans, Burkholderia vietnamiensis, Acinetobacter radioresistens, Herminiimonas arsenicoxydans, Alcaligenes faecalis, Oxalobacter formigenes*, etc. Further, phosphate transporters, phosphonate transporters, etc. that function as phosphite transporters can be used as appropriate.

As a phosphite transporter, the aforementioned phosphite transporter (RsPtxABC) derived from strain 4506 can be suitably used, although the present invention is not limited to this. The amino acid sequences of RsPtxA, RsPtxB, and RsPtxC are indicated by SEQ ID NO: 3, 4, and 5, respectively. It should be noted that since the phosphite transporter is constituted by the three units, namely RsPtxA, RsPtxB, and RsPtxC, RsptxA, RsptxB, and RsptxC need all be introduced into the target microorganism in order for the phosphite transporter to function as such.

RsptxA is a polynucleotide encoding (1) a protein consisting of the amino acid sequence of SEQ ID NO: 3 or (2) a protein consisting of an amino acid with a deletion, substitution, or addition of one or several amino acids in the amino acid sequence of SEQ ID NO: 3 and functioning as the phosphite transporter when associated with RsPtxB and RsPtxC.

Further, RsptxB is a polynucleotide encoding (3) a protein consisting of the amino acid sequence of SEQ ID NO: 4 or (4) a protein consisting of an amino acid with a deletion, substitution, or addition of one or several amino acids in the amino acid sequence of SEQ ID NO: 4 and functioning as the phosphite transporter when associated with RsPtxA and RsPtxC.

Further, RsptxC is a polynucleotide encoding (5) a protein consisting of the amino acid sequence of SEQ ID NO: 5 or (6) a protein consisting of an amino acid with a deletion, substitution, or addition of one or several amino acids in the amino acid sequence of SEQ ID NO: 5 and functioning as the phosphite transporter when associated with RsPtxA and RsPtxB.

Further, RsptxA can be expressed as (7) a polynucleotide including a polynucleotide consisting of the nucleotide sequence of SEQ ID NO: 6 or (8) a polynucleotide that hybridizes under stringent conditions with a nucleotide sequence complementary to a polynucleotide including a polynucleotide consisting of the nucleotide sequence of SEQ ID NO: 6.

Further, RsptxB can be expressed as (9) a polynucleotide including a polynucleotide consisting of the nucleotide sequence of SEQ ID NO: 7 or (10) a polynucleotide that hybridizes under stringent conditions with a nucleotide sequence complementary to a polynucleotide including a polynucleotide consisting of the nucleotide sequence of SEQ ID NO: 7.

Further, RsptxC can be expressed as (11) a polynucleotide including a polynucleotide consisting of the nucleotide sequence of SEQ ID NO: 8 or (12) a polynucleotide that hybridizes under stringent conditions with a nucleotide sequence complementary to a polynucleotide including a polynucleotide consisting of the nucleotide sequence of SEQ ID NO: 8.

It should be noted that genes encoding the three units may be introduced into the target microorganism by separate expression vectors, respectively, or may be introduced into the target microorganism by a single expression vector containing genes encoding the three units. Further, the genes encoding the three units may be introduced into the target microorganism by a different expression vector from the expression vector for the phosphite dehydrogenase gene or may be introduced into the target microorganism by the same expression vector as the expression vector for the phosphite dehydrogenase gene. In this case, RsptxABCD can for example be a polynucleotide of (i) or (j):

(i) a polynucleotide including a polynucleotide consisting of the nucleotide sequence of SEQ ID NO: 15; and (j) a polynucleotide that hybridizes under stringent conditions with a nucleotide sequence complementary to a polynucleotide including a polynucleotide consisting of the nucleotide sequence of SEQ ID NO: 15 and that encodes a phosphite transporter and a phosphite dehydrogenase.

As for those items which this section has in common with the previous section [2. Phosphite Dehydrogenase and a Phosphite Dehydrogenase Gene], the descriptions in the previous section can be incorporated as appropriate.

[4. NADP-utilizing Phosphite Dehydrogenase and an NADP-utilizing Phosphite Dehydrogenase Gene]

Although not particularly limited, an NADP-utilizing phosphite dehydrogenase can be used as appropriate in the selective culturing method of the present invention. Photosynthetic organisms including cyanobacteria are known to generally have high intracellular NADP concentrations, as Calvin cycle is used. Meanwhile, heterotrophic bacteria such as *E. coli* generally have high intracellular NAD concentrations.

RsptxD, which is derived from heterotrophic bacteria *Ralstonia* sp. strain 4506, was believed to have higher substrate specificity to NAD than to NADP. For this reason, it was believed that in a case where the target microorganism is a microorganism having a high intracellular NADP concentration, including photosynthetic microorganisms such as cyanobacteria, NADP cannot be efficiently utilized, with the result that phosphorous acid cannot be efficiently oxidized. That is, when the target microorganism is a microorganism having a high intracellular NADP concentration, such as cyanobacteria, it may be preferable to use an NADP-utilizing phosphite dehydrogenase having high substrate specificity to NADP.

As used herein, the term "NADP-utilizing phosphite dehydrogenase" means an enzyme variant modified to have higher substrate specificity to NADP than a wild-type phosphite dehydrogenase.

So far, a protein stereostructure of a dehydrogenase such as α-hydroxysteroid dehydrogenase has been shown, and it has been shown from the stereostructure that an acidic amino-acid residue (aspartic acid, glutamic acid) located posterior by about 18 amino-acid residues to the Rossman-fold domain to which NAD bind is responsible for the utilizability of NADP (Refer to Katzberg M., et al., *Int. J. Mol. Sci.*, Vol. 11, 1735-1758, 2010). Further, it has been revealed that the introduction of a positively-charged amino acid into a site around this acidic amino-acid residue by site-specific mutagenesis leads to a rise in utilizability of NADP.

As for a phosphite dehydrogenase (PtxD), Woodyer et al. successfully raised specificity to NADP as a result of replacing the 175th glutamic acid and the 176th alanine of a phosphite dehydrogenase derived from *Pseudomonas stutzeri* with alanine and arginine, respectively (Refer to Woodyer et al., *Biochemistry*, Vol. 42, 11604-11614, 2003.).

An NADP-utilizing phosphite dehydrogenase that can be used for the selective culturing method of the present invention may be subjected to amino acid substitution from the above point of view. Amino acid substitution can be carried out by a publicly-known method, and as such, does not particularly require a person skilled in the art to go through a trial and error process.

In the Examples below, an enzyme variant (RsPtxD D175A) obtained by replacing the 175th aspartic acid of RsPtxD with alanine, an enzyme variant (RsPtxD P176R) obtained by replacing the 176th proline of RsPtxD with arginine, and an enzyme variant (RsPtxD D175A/P176R) obtained by replacing the 175th aspartic acid of RsPtxD with alanine and replacing the 176th proline of RsPtxD with arginine were obtained. Each of the enzyme variants had higher substrate specificity to NADP than a wild-type enzyme.

The amino acid sequences of RsPtxD D175A, RsPtxD P176R, and RsPtxD D175A/P176R are indicated by SEQ ID NO: 9, 10, and 11, respectively. Further, the nucleotide sequences of RsptxD D175A, RsptxD P176R, RsptxD D175A/P176R are indicated by SEQ ID NO: 12, 13, and 14, respectively.

That is, an NADP-utilizing phosphite dehydrogenase gene that can be used for the selective culturing method of the present invention can be a polynucleotide encoding a protein of (e) or (f):

(e) a protein consisting of the amino acid sequence of SEQ ID NO: 9, 10, or 11; and (f) a protein consisting of an amino acid with a deletion, substitution, or addition of one or several amino acids in the amino acid sequence of SEQ ID NO: 9, 10, or 11 and having NADP-utilizing phosphite dehydrogenase activity.

Further, the NADP-utilizing phosphite dehydrogenase gene can be a polynucleotide of (g) or (h):

(g) a polynucleotide consisting of the nucleotide sequence of SEQ ID NO: 12, 13, or 14; and (h) a polynucleotide that hybridizes under stringent conditions with a nucleotide sequence complementary to a polynucleotide consisting of the nucleotide sequence of SEQ ID NO: 12, 13, or 14 and that encodes an NADP-utilizing phosphite dehydrogenase.

As for those items which this section has in common with the previous sections [2. Phosphite Dehydrogenase and a Phosphite Dehydrogenase Gene] and [3. Phosphite Transporter and a Phosphite Transporter Gene], the descriptions in the previous sections can be incorporated as appropriate.

The present invention can also be configured as follows:

That is, a method for selectively culturing a microorganism according to the present invention includes the step of culturing, in a culture medium containing phosphorous acid as a sole phosphorous source, a microorganism into which a phosphite dehydrogenase gene has been introduced.

The method for selectively culturing a microorganism according to the present invention may be configured to include the step of culturing, in a culture medium containing phosphorous acid as a sole phosphorous source and containing no antibiotic substance, a recombinant microorganism into which a phosphite dehydrogenase gene has been introduced.

The method for selectively culturing a microorganism according to the present invention may be configured such that the microorganism is selectively cultured over a long period of time both under sterile conditions and unsterile conditions.

A method for selectively culturing a microorganism according to the present invention includes the step of culturing, under unsterile conditions in a culture medium containing phosphorous acid as a sole phosphorous source, a microorganism into which a phosphite dehydrogenase gene has been introduced.

A phosphite dehydrogenase is a protein that only some bacteria possess, and is an enzyme that oxidizes phosphorous acid ($PO_3$) NAD-dependently and produces NADH and phosphoric acid. Phosphorus is a cell constituent such as a nucleic acid and a lipid, and is necessary for an in vivo intercellular messenger. For this reason, phosphorus is one of the elements essential to living organisms, and no living organism can grow without a phosphorous source. Moreover, microorganisms that have phosphite dehydrogenases and that can utilize phosphorous acid are limited to a small minority of bacteria. Therefore, in a culture medium containing phosphorous acid as a sole phosphorous source, the microorganism of interest into which a phosphite dehydrogenase gene has been introduced and the small minority of bacteria having phosphite dehydrogenase by nature can grow, but a large majority of unintended microorganisms having no phosphite dehydrogenases cannot grow. This makes it possible to prevent contamination with unintended microorganisms.

The method for selectively culturing a microorganism according to the present invention may be configured such that the microorganism has introduced thereinto a phosphite dehydrogenase gene and a phosphite transporter gene.

The method for selectively culturing a microorganism according to the present invention may be configured such that the unsterile conditions are conditions under which a culture apparatus and a culture medium have not been sterilized.

The method for selectively culturing a microorganism according to the present invention may be configured such that the culture medium is a culture medium containing no antibiotic substance.

The method for selectively culturing a microorganism according to the present invention may be configured such that the culture is performed in 10 L or more of a culture medium.

The method for selectively culturing a microorganism according to the present invention may be configured such that the culture is performed in an open system.

The method for selectively culturing a microorganism according to the present invention is preferably configured such that: the microorganism has introduced thereinto a plasmid containing the phosphite dehydrogenase gene; and the method makes it possible to increase the number of copies of the plasmid and, in a case where the microorganism is subcultured, stably maintain the number of copies of the plasmid.

The method for selectively culturing a microorganism according to the present invention may be configured such that the phosphite dehydrogenase gene is an NADP-utilizing phosphite dehydrogenase gene.

The method for selectively culturing a microorganism according to the present invention may be configured such that the phosphite dehydrogenase gene is a polynucleotide encoding a protein of (a) or (b):

(a) a protein consisting of the amino acid sequence of SEQ ID NO: 1; and (b) a protein consisting of an amino acid with a deletion, substitution, or addition of one or several amino acids in the amino acid sequence of SEQ ID NO: 1 and having phosphite dehydrogenase activity.

The method for selectively culturing a microorganism according to the present invention may be configured such that the phosphite dehydrogenase gene is a polynucleotide of (c) or (d):

(c) a polynucleotide consisting of the nucleotide sequence of SEQ ID NO: 2; and (d) a polynucleotide that hybridizes under stringent conditions with a nucleotide sequence complementary to a polynucleotide consisting of the nucleotide sequence of SEQ ID NO: 2 and that encodes a phosphite dehydrogenase protein.

The method for selectively culturing a microorganism according to the present invention may be configured such that: the phosphite transporter gene consists of polynucleotides encoding RsPtxA, RsPtxB, and RsPtxC, respectively, RsPtxA, RsPtxB, and RsPtxC constituting a phosphite transporter; RsPtxA is (1) a protein consisting of the amino acid sequence of SEQ ID NO: 3 or (2) a protein consisting of an amino acid with a deletion, substitution, or addition of one or several amino acids in the amino acid sequence of SEQ ID NO: 3 and functioning as the phosphite transporter when associated with RsPtxB and RsPtxC; RsPtxB is (3) a protein consisting of the amino acid sequence of SEQ ID NO: 4 or (4) a protein consisting of an amino acid with a deletion, substitution, or addition of one or several amino acids in the amino acid sequence of SEQ ID NO: 4 and functioning as the phosphite transporter when associated with RsPtxA and RsPtxC; and RsPtxC is (5) a protein consisting of the amino acid sequence of SEQ ID NO: 5 or (6) a protein consisting of an amino acid with a deletion, substitution, or addition of one or several amino acids in the amino acid sequence of SEQ ID NO: 5 and functioning as the phosphite transporter when associated with RsPtxA and RsPtxB.

The method for selectively culturing a microorganism according to the present invention may be configured such that: the phosphite transporter gene consists of polynucleotides encoding RsPtxA, RsPtxB, and RsPtxC, respectively, RsPtxA, RsPtxB, and RsPtxC constituting a phosphite transporter; the polynucleotide encoding RsPtxA is (7) a polynucleotide including a polynucleotide consisting of the nucleotide sequence of SEQ ID NO: 6 or (8) a polynucleotide that hybridizes under stringent conditions with a nucleotide sequence complementary to a polynucleotide including a polynucleotide consisting of the nucleotide sequence of SEQ ID NO: 6; the polynucleotide encoding RsPtxB is (9) a polynucleotide including a polynucleotide consisting of the nucleotide sequence of SEQ ID NO: 7 or (10) a polynucleotide that hybridizes under stringent conditions with a nucleotide sequence complementary to a polynucleotide including a polynucleotide consisting of the nucleotide sequence of SEQ ID NO: 7; and the polynucleotide encoding RsPtxC is (11) a polynucleotide including a polynucleotide consisting of the nucleotide sequence of SEQ ID NO: 8 or (12) a polynucleotide that hybridizes under stringent conditions with a nucleotide sequence complementary to a polynucleotide including a polynucleotide consisting of the nucleotide sequence of SEQ ID NO: 8.

The method for selectively culturing a microorganism according to the present invention may be configured such that the NADP-utilizing phosphite dehydrogenase gene is a polynucleotide encoding a protein of (e) or (f):

(e) a protein consisting of the amino acid sequence of SEQ ID NO: 9, 10, or 11; and (f) a protein consisting of an amino acid with a deletion, substitution, or addition of one or several amino acids in the amino acid sequence of SEQ ID NO: 9, 10, or 11 and having NADP-utilizing phosphite dehydrogenase activity.

The method for selectively culturing a microorganism according to the present invention may be configured such that the NADP-utilizing phosphite dehydrogenase gene is a polynucleotide of (g) or (h):

(g) a polynucleotide consisting of the nucleotide sequence of SEQ ID NO: 12, 13, or 14; and (h) a polynucleotide that hybridizes under stringent conditions with a nucleotide sequence complementary to a polynucleotide consisting of the nucleotide sequence of SEQ ID NO: 12, 13, or 14 and that encodes an NADP-utilizing phosphite dehydrogenase.

The method for selectively culturing a microorganism according to the present invention may be configured such that the microorganism has introduced thereinto a polynucleotide of (i) or (j):

(i) a polynucleotide including a polynucleotide consisting of the nucleotide sequence of SEQ ID NO: 15; and (j) a polynucleotide that hybridizes under stringent conditions with a nucleotide sequence complementary to a polynucleotide including a polynucleotide consisting of the nucleotide sequence of SEQ ID NO: 15 and that encodes a phosphite transporter and a phosphite dehydrogenase.

The method for selectively culturing a microorganism according to the present invention may be configured such that the microorganism is *Escherichia coli*.

The method for selectively culturing a microorganism according to the present invention may be configured such that the microorganism is yeast or mold.

It should be noted that cloning of phosphite dehydrogenase genes with bacteria such as *E. coli* has been practiced so far (e.g. see Non-patent Literature 2). The Applicant, too, found a phosphite dehydrogenase having high thermal stability and high specific activity and filed an international application therefor (International Publication Number: WO/2012/147556). In this application, too, transformants are cultured by introducing a phosphite dehydrogenase gene into *E. coli*. However, transformants have conventionally not been cultured on the basis of the technical idea that a microorganism is selectively cultured by using a phosphite dehydrogenase gene as a selective marker as in the present invention. This makes impossible to easily arrive at selectively culturing transformants as a target microorganism by inhibiting the growth of microorganisms other than the target microorganism in a culture medium containing phosphorous acid as a sole phosphorous source. Furthermore, since transformants have conventionally not been cultured on the basis of the technical idea that a microorganism is selectively cultured by using a phosphite dehydrogenase gene as a selective marker as in the present invention, transformants have not been cultured under unsterile conditions in a culture medium containing phosphorous acid as a sole phosphorous source. Further, it is not easy to arrive at culturing transformants under unsterile conditions in a culture medium containing phosphorous acid as a sole phosphorous source.

Furthermore, since an antibiotic-resistance gene has conventionally been used as a selective marker, an antibiotic substance is always contained in a culture medium. In this regard, the conventional culture of transformants cannot solve the problems to be solved by the present invention. On the other hand, the present invention can solve the problems caused by using an antibiotic substance, without making it necessary to cause an antibiotic substance to be contained in a culture medium.

EXAMPLES

[1. Cloning of RsptxABCD]

RsptxABCD containing a phosphite dehydrogenase gene: RsptxD and a phosphite transporter gene: RsptxABC of *Ralstonia* sp. strain 4506 (Refer to Hirota et al., *J. Biosci. Bioeng.*, Vol. 113, 445-450, 2012.) was cloned in the following manner.

With a chromosome of strain 4506 as a template, amplified DNA of approximately 3.6 kb was obtained by performing PCR with the following primers:
Primer Sequences:
ptxA(-186)fw: 5'-GGAATTCTAGCAGGCGTCTAT-ATTTGGCATAG-3' (SEQ ID NO: 16). Note "GGAATTC" at the 5'-end is a sequence added for cloning.
ptxD_rv: 5'-AAGGATCCCAGATCTATCACGCCGCCTT-TACTC-3' (SEQ ID NO: 17). Note "AAGGATCC" at the 5'-end is a sequence added for cloning.

The DNA fragment thus obtained was purified and cloned into a pGEM-Easy T-vector (Promega KK.). An EcoRI digestion product of the plasmid thus obtained was ligated to an EcoRI digestion product of pSTV28 (Takara Bio Inc.) and introduced into *E. coli* DH5α.

Figure 1:
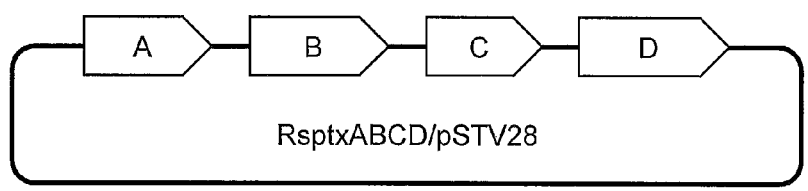
FIG. 1 is a schematic view of the structure of the plasmid vector RsptxABCD/pSTV28 used in the Examples.

Plasmids were obtained from transformants, and from among the plasmids thus obtained, a plasmid in which RsptxABCD had been inserted in the same orientation as the transcriptional orientation of lacZ was selected and named "RsptxABCD/pSTV28" (See FIG. 1.).

[2. Introduction of RsptxABCD into *E. Coli* and Growth on Phosphorous Acid Culture Medium]

RsptxABCD/pSTV28 was introduced into *E. coli* MT2012 (Refer to K. Motomura, et al., *FEMS Microbiol. Lett.*, 320, 25-32 (2011)) having complete absence of the capability to utilize phosphoric acid and phosphorous acid. Then, *E. coli* MT2012 was applied to a morpholinopropane-sulfonic acid plate culture medium containing 0.5 M of phosphorous acid: MOPS-Pt (0.5) (0.5 mM phosphite, 22.2 mM glucose, 40 mM potassium morpholinopropane sulfonate [pH 7.2], 50 mM NaCl, 9.52 mM $NH_4Cl$, 4 mM Tricine, 0.52 mM $MgCl_2$, 0.28 mM $K_2SO_4$, 0.01 mM $FeSO_4$, 0.0005 mM $CaCl_2$, 20 µM thiamine, 1.5% Agar), and was incubated at 37° C.

Figure 2:
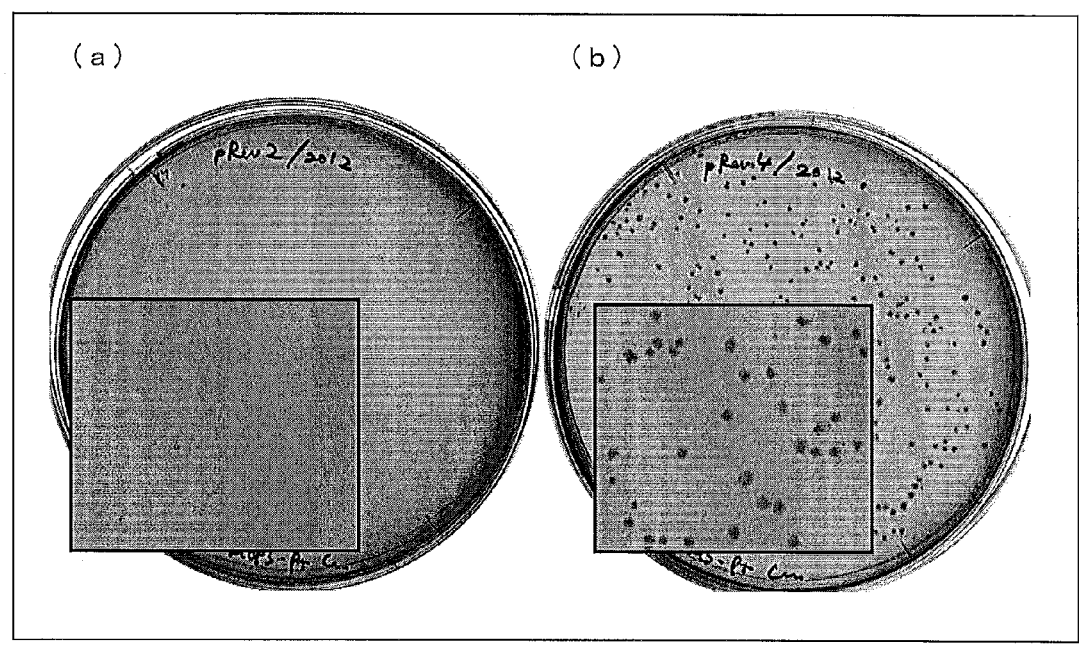

The results are shown in FIG. 2. (a) of FIG. 2 shows a result of *E. coli* MT2012 into which RsptxABCD/pSTV28 were not introduced, and (b) of FIG. 2 shows a result of *E. coli* MT2012 into which RsptxABCD/pSTV28 had been introduced. According to FIG. 2, only *E. coli* in which RsptxABCD was expressed could grow on a culture medium containing phosphorous acid as a sole phosphorous source. This shows that the introduction of RsptxABCD into *E. coli* makes it possible to selectively culture *E. coli*.

After 72 hours, a colony of transformants exhibiting a satisfactory growth was confirmed. A possible reason for this was that a long-term culture under limit-pressure conditions where phosphoric acid cannot be acquired induced self-mutation in a gene in a plasmid with the result that a clone having a RsptxABCD variant with higher compatibility appeared.

Accordingly, the plasmid of the clone having grown on MOPS-Pt (0.5) was obtained, and all DNA nucleotide sequences of the DNA fragment were determined, whereby it was confirmed that G (guanine) located upstream by eight bases of the start codon of RsptxA had mutated into A (adenine). Since this mutation is considered to be in a ribosome binding region, it was believed that this mutation caused the translation volume of RsptxABCD to be an appropriate volume with the result that compatibility with *E. coli* became so high that it became possible to efficiently use phosphorous acid. In the experiment that followed, the plasmid RsptxABCDmt/pSTV28 obtained from the Rsptx-ABCD variant was used.

[3. Introduction of RsptxABCD into Cyanobacteria *Synechococcus Elongates* PCC7942 and Growth on Phosphorous Acid Culture Medium]

Figure 3:
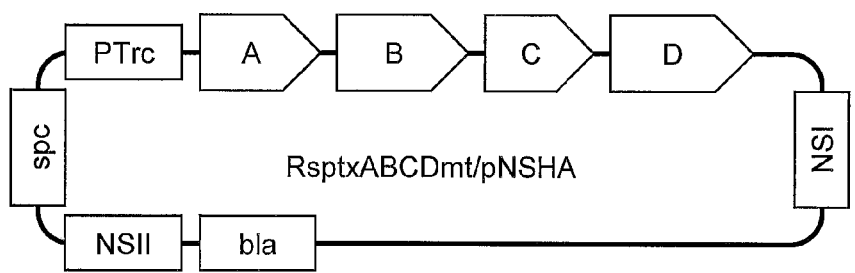

A DNA fragment (approximately 3.6 kb) obtained by EcoRI digestion of RsptxABCDmt/pSTV28 was introduced into an EcoRI site of a plasmid pNSHA (Refer to Watanabe et al., *Mol Microbiol.* 2012 February; 83(4): 856-65) for use in gene transfer to *S. elongates* PCC7942 (hereinafter referred to as "strain PCC7942"). A plasmid in which promoter control and a gene in the DNA fragment are identical in orientation was chosen as RsptxABCDmt/pN-SHA (See FIG. 3.).

With use of RsptxABCDmt/pNSHA, strain PCC7942 was transformed in the following manner. Strain PCC7942 was cultured in 10 mL of a BG-11 culture medium ($NaNO_3$: 1.5 g, $K_2HPO_4$: 30 mg, $MgSO_4 \cdot 7H_2O$: 75 mg, $CaCl_2 \cdot 2H_2O$: 36 mg, citric acid: 6 mg, $Na_2$.EDTA: 1 mg, $Na_2CO_3$: 20 mg, $H_3BO_3$: 2.86 mg, $MnCl_2 \cdot 4H_2O$: 1.81 mg, $ZnSO_4 \cdot 7H_2O$: 222 µg, $Na_2MoO_4 \cdot 2H_2O$: 0.39 mg, $CuSO_4 \cdot 5H_2O$: 79 µg, $Co(NO_2)_2 \cdot 6H_2O$: 49.4 µg, vitamin $B_{12}$: 1 µg, distilled water: 1 L). After $OD_{750}$ became about 0.7~1.0, the cells were harvested by centrifugalization (6,000 rpm, 5 minutes) and resuspended in 1.0 mL of the BG-11 culture medium. To 400 µL of the suspension, 5 µL (100 µg/mL) of the plasmid were added. The suspension and the plasmid were mixed together for 12 hours by a shaker in an incubator at 28° C. while being shielded from light by aluminum foil.

After that, the aluminum foil was removed, and the suspension and the plasmid were mixed together for another one hour. The bacterial mixture thus obtained was applied to a BG-11 plate culture medium containing spectinomycin (40 μL/mL), and was cultured in a plant incubator (Illuminance 2000 to 3000 Lux, Temperature: 28° C.). Colonies obtained approximately ten days after the start of culture were used as transformants in the analyses that followed.

The transformants thus obtained were cultured in a BG-11 culture medium. After that, the bacterial cells were deposited by centrifugalization (8,000 rpm, 5 minutes), and were resuspended in sterilized water. Phosphoric acid remaining in the bacterial suspension was removed by repeating this operation three times. After that, the bacterial cells were inoculated into a BG-11 culture medium containing 0.2 mM of phosphorous acid as a sole phosphorous source, and were incubated at 28° C. As a control, culture was performed with use of transformants obtained by introducing pNSHA into strain PCC7942.

Figure 4:
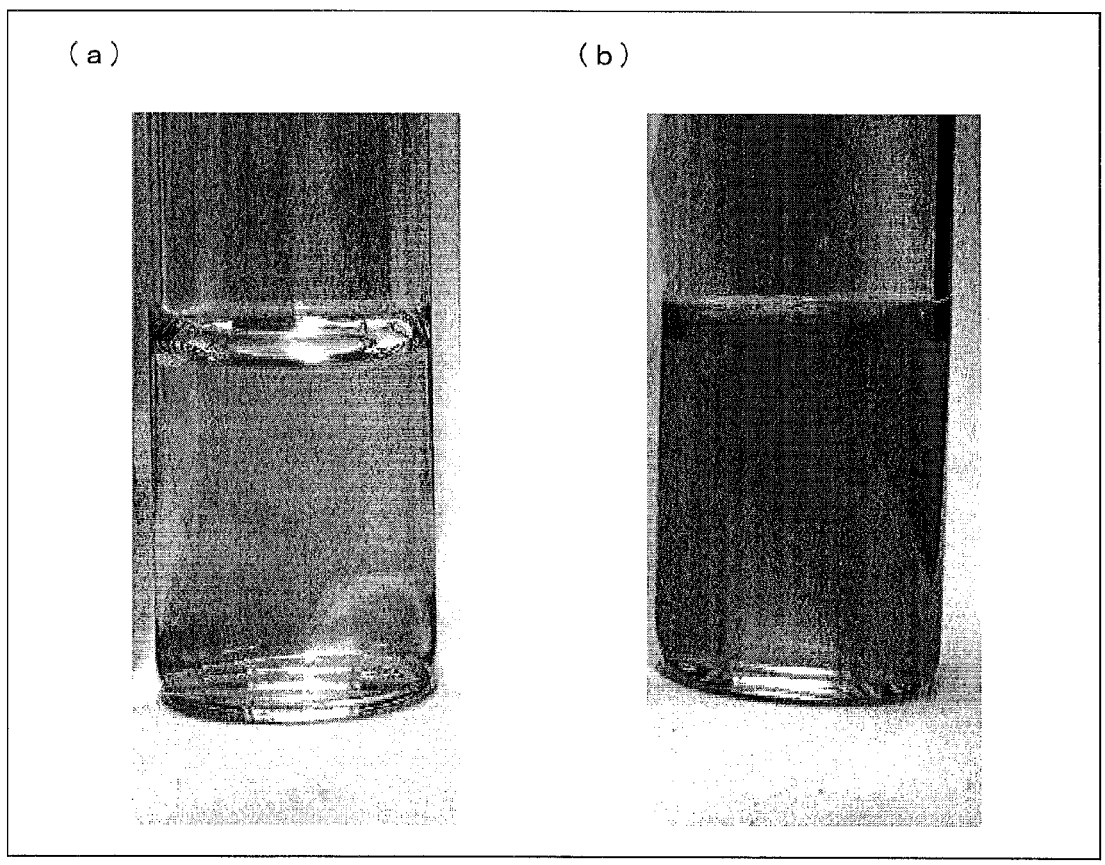

The results are shown in FIG. 4. (a) of FIG. 4 shows a result of transformants (controls) obtained by introducing pNSHA into strain PCC7942, and (b) of FIG. 4 shows a result of transformants obtained by introducing RsptxAB-CDmt/pNSHA into strain PCC7942. According to FIG. 4, only the transformants into which RsptxABCDmt/pNSHA had been introduced grew. That is, it can be said that the expression of RsptxABCDmt made the cyanobacteria able to utilize phosphorous acid. This shows that the introduction of RsptxABCDmt into cyanobacteria makes it possible to selectively culture the cyanobacteria.

[4. Alteration of RsPtxD to NADP-utilizing Type by Site-specific Introduction of Mutation]

A variant (RsPtxD D175A) obtained by replacing the 175th aspartic acid of RsPtxD with alanine, a variant (RsPtxD P176R) obtained by replacing the 176th proline of RsPtxD with arginine, and a variant (RsPtxD D175A/P176R) obtained by replacing the 175th aspartic acid of RsPtxD with alanine and replacing the 176th proline of RsPtxD with arginine were obtained. These variants were obtained in the following manner.

First, primers (RsPTXD-F and RsPTXD-R) for obtaining the whole-length sequence of ptxD were prepared. The following shows the nucleotide sequences of these primers:

```
                                   (SEQ ID NO: 18)
RsPTXD-F:  5'-CGGGATCCGATGAAGCCCAAAGTCGTCCTC-3'

(SEQ ID NO: 19)
RsPTXD-R:  5'-CGGAATTCGCCGCCTTTACTCCCGGATAC-3'
```

With the chromosome DNA of strain 4506 as a template, a DNA fragment of approximately 1 kb was amplified by performing PCR with RsPTXD-F and RsPTXD-R. By inserting the DNA fragment thus amplified into a plasmid pET21b (Novagen), RsptxD/pET21b was prepared.

Next, PCR was performed using the primers listed below and a Prime Star Mutagenesis Basal Kit (Takara Bio Inc.), with RsptxD/pET21b as a template. DNA was introduced into competent cells in accordance with the manual of the kit. From the colony thus obtained, a plasmid was obtained. It should be noted that the introduction of a mutation into an intended position was confirmed by a sequence analysis.

```
ptxD sdm_DM-fw:
                                   (SEQ ID NO: 20)
5'-TTGCGCACGTATTCCGCTCAATGCCGAA-3' ptxD sdm_DM-rv:
                                   (SEQ ID NO: 21)
5'-GGAATACGTGCGCAATACAAGAGATTCA-3' ptxD sdmP176R-fw:
                                   (SEQ ID NO: 22)
5'-TTGCGATCGTATTCCGCTCAATGCCGAA-3' ptxD sdmP176R-rv:
                                   (SEQ ID NO: 23)
5'-GGAATACGATCGCAATACAAGAGATTCA-3' ptxD sdmD175A-fw:
                                   (SEQ ID NO: 24)
5'-TTGCGCACCGATTCCGCTCAATGCCGAA-3' ptxD sdmD175A-rv:
                                   (SEQ ID NO: 25)
5'-GGAATCGGTGCGCAATACAAGAGATTCA-3'
```

The plasmid thus obtained was introduced into E. coli Rosetta 2 (Clontech), whereby a cellular rough extraction liquid containing a recombinant protein was obtained. The cellular rough extraction liquid was used to measure phosphite dehydrogenase activity with NAD and NADP as substrates. The phosphite dehydrogenase activity was measured in the following manner.

Each of the clones thus obtained was inoculated into a 4 mL of a 2×YT liquid medium, and was cultured overnight at 45° C. 1 mL of a culture solution thus obtained was charged into a 1.5-mL tube, and then the tube was centrifuged at 12000 rpm for 5 minutes. Then, a supernatant was discarded to obtain a pellet of bacterial cells.

In order to remove phosphoric acid derived from the culture medium, the pellet of the bacterial cells was suspended in 1 mL of an MOPS culture medium containing no phosphorous component (MOPS (0): 22.2 mM glucose, 40 mM potassium morpholinopropane sulfonate [pH 7.2], 50 mM NaCl, 9.52 mM $NH_4Cl$, 4 mM Tricine, 0.52 mM $MgCl_2$, 0.28 mM $K_2SO_4$, 0.01 mM $FeSO_4$, 0.0005 mM $CaCl_2$, 20 μM thiamine), and a suspension thus obtained was centrifuged at 12000 rpm for 5 minutes. Then, a supernatant was discarded to obtain a pellet of bacterial cells. This washing operation was repeated once to obtain a pellet of bacterial cells, which was then suspended in 1 mL of MOPS (0). Subsequently, 100 μL of a suspension thus obtained was inoculated on 10 mL of MOPS-Pt (0.5), and was cultured at 45° C.

When a value of $OD_{600}$ reached 1.5 to 2.0 after 24 to 72 hours of culture, a whole of the culture medium was transferred to a 50-mL tube, and then the tube was centrifuged at 6000 rpm for 10 minutes. After the centrifugation, a supernatant was discarded to obtain a pellet of bacterial cells.

The pellet of the bacterial cells was suspended in 10 mL of MOPS (0), and then subjected to ultrasonic disruption (Digital sonifier, BRANSON) for 10 minutes with a 20% output. The MOPS (0) having been subjected to the ultrasonic disruption was dispensed to an ultracentrifugation tube (Centrifuge Tubes, BECKMAN, 349622), and the ultracentrifugation tube was ultracentrifuged in an ultracentrifuge (Optima TM TLX Ultracentrifuge, BECKMAN COULTER) at 270,000×g and 4° C. for 45 minutes.

After the ultracentrifugation, a supernatant was collected to be used as a crude extract for measuring phosphite dehydrogenase activity. A total of 1000 μL of a reaction solution was prepared which contained the crude extract (protein amount: 10 μg), NAD or NADP (1 mM), phosphorous acid (1 mM), and a MOPS-KOH buffer (20 mM, pH 7.4). A temperature of the reaction solution was elevated to 45° C., so that a reaction was started. A sample was collected, each in an amount of 100 μL, at predetermined time intervals for a predetermined period of time (0 to 180 minutes), and absorbance (340 nm) of each sample was measured. Phosphite dehydrogenase activity was evaluated in terms of an amount of NADH (in the case of an NADP substrate, NADPH) generated by 1 mg of protein per unit time.

Figure 5:
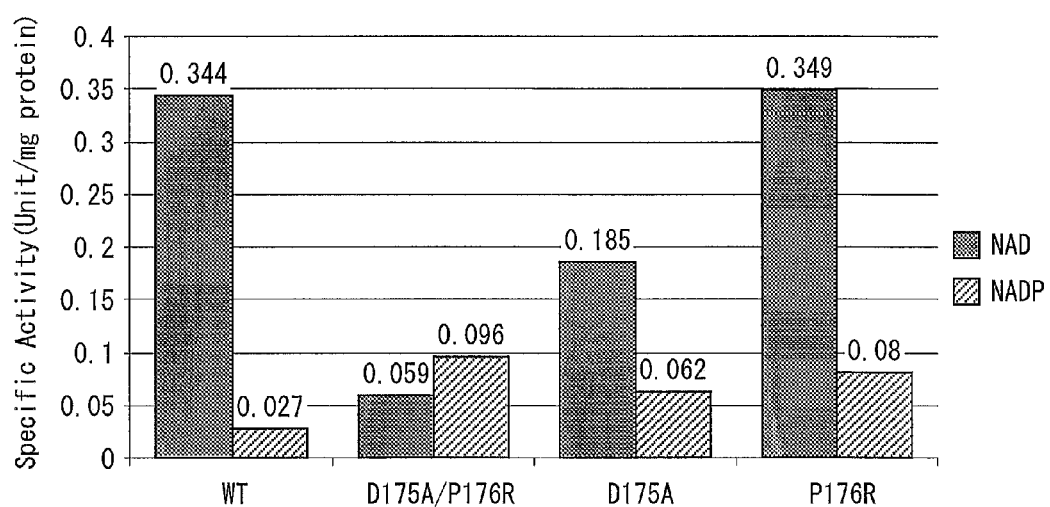

The results are shown in FIG. 5. In FIG. 5, the legend "WT" represents a result of unmutated wild-type RsPtxD, the legend "D175A/P176R" represents a result for RsPtxD D175A/P176R, the legend "D175A" represents a result for RsPtxD D175A, and the legend "P176R" represents a result for RsPtxD P176R.

Whereas RsPtxD exhibited overwhelmingly higher phosphite dehydrogenase activity in the case where NAD was used as a substrate than in the case where NADP was used as a substrate (NADP/NAD=0.0785), RsPtxD P176R exhibited higher phosphite dehydrogenase activity in the case where NADP was used as a substrate than did wild-type RsPtxD. As a result, in the case of RsPtxD P176R, NADP/NAD=0.23. RsPtxD D175A exhibited higher phosphite dehydrogenase activity in the case where NADP was used as a substrate than did wild-type RsPtxD, and exhibited lower phosphite dehydrogenase activity in the case where NAD was used as a substrate than did wild-type RsPtxD. As a result, in the case of RsPtxD D175A, NADP/NAD=0.34. Furthermore, RsPtxD D175A/P176R exhibited higher phosphite dehydrogenase activity in the case where NADP was used as a substrate than in the case where NAD was used as a substrate. As a result, in the case of RsPtxD D175A/P176R, NADP/NAD=1.63. That is, the phosphite dehydrogenase activity of RsPtxD D175A/P176R was 20.7 times higher than that of wild-type RsPtxD.

It was therefore confirmed that the site-specific introduction of mutation brought about an improvement in the NADP-utilizing capability of RsPtxD.

[5. Introduction of RsptxABCD into Wild-type Strain of *E. Coli* and Growth on Phosphorous Acid Culture Medium]

In section [2. Introduction of RsptxABCD into *E. coli* and Growth on Phosphorous Acid Culture Medium] above, *E. coli* MT2012 having complete absence of the capability to utilize phosphoric acid and phosphorous acid was used. In this section, however, an experiment was conducted using a wild-type strain of *E. coli* (*E. coli* K-12 strain MG1655: hereinafter referred to as "*E. coli* MG1655" (Blomfield I C, et al., *Mol. Microbiol.* 1991, June; 5 (6): 1439-45)) not deprived of the capability to utilize phosphoric acid and phosphorous acid.

Strains were prepared by introducing RsptxABCDmt/pSTV28 and pSTV28 into *E. coli* MG1655, respectively, and were each cultured all night long at 37° C. in 4 mL of an MOPS-Pt (0.5) liquid medium. Each of the bacterial culture solutions thus obtained was washed once with MOPS (0), was resuspended so that $OD_{600}$ became 1.0, and then was inoculated by 1% (v/v) into a 300-mL conical flask containing 60 mL of MOPS-Pt (0.5). Each of the culture solutions thus inoculated was cultured at 37° C. and had the value of $OD_{600}$ measured over time. Measurements thus obtained were plotted as a function of culture time, and the specific growth rate of bacterial cells was measured.

Figure 7:
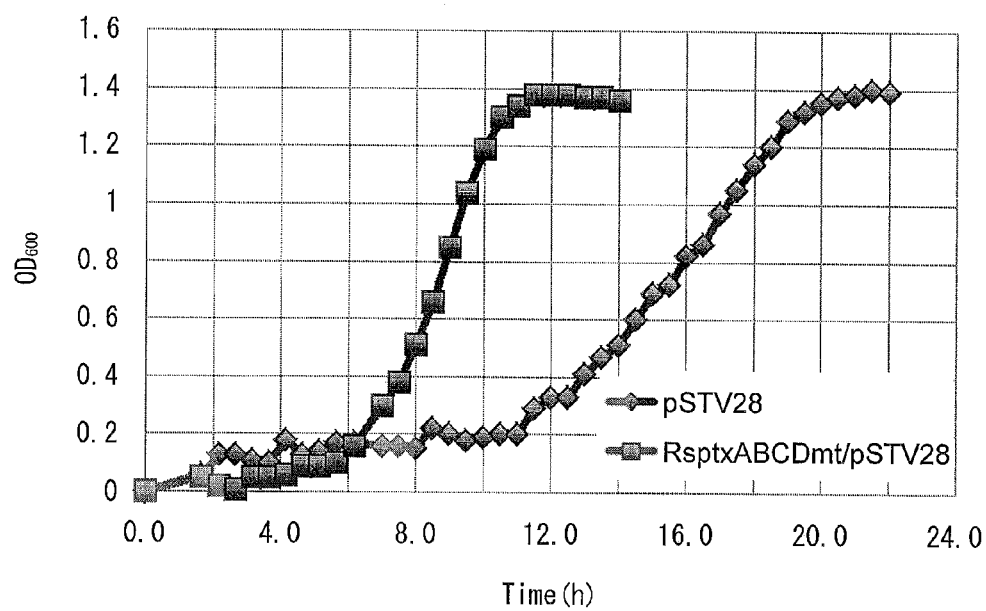

The results are shown in FIG. 7. FIG. 7 is a graph showing changes over time in $OD_{600}$ of transformants of *E. coli* MG1655 into which RsptxABCDmt/pSTV28 had been introduced and transformants of *E. coli* MG1655 into which only vector pSTV28 had been introduced.

According to FIG. 7, the specific growth rate of transformants of *E. coli* MG1655 into which RsptxABCDmt/pSTV28 had been introduced was twice or more times higher than that of transformants of *E. coli* MG1655 into which only vector pSTV28 had been introduced. It should be noted here that the specific growth rate of the transformants of *E. coli* MG1655 into which only pSTV28 had been introduced was 0.248 h$^{-1}$, and the specific growth rate of the transformants of *E. coli* MG1655 into which RsptxABCDmt/pSTV28 had been introduced was 0.524 h$^{-1}$. Furthermore, it was shown that the transformants of *E. coli* MG1655 into which only pSTV28 had been introduced requires almost twice as long a lag time (time required until growth starts) than the transformants of *E. coli* MG1655 into which RsptxABCDmt/pSTV28 had been introduced. For this reason, it can be predicted that if the two types of bacterial cells exist simultaneously, the culture medium will have run out of its nutrients by the time the transformants of *E. coli* MG1655 into which RsptxABCDmt/pSTV28 had been introduced finish growing, the transformants of *E. coli* MG1655 into which only pSTV28 had been introduced no longer grow. This means that the introduction of RsptxABCD was confirmed to also have an effect on wild-type strains of *E. coli*.

[6. Open-system Culture using an Unsterilized Culture Medium]

An experiment was conducted in the same manner as in section [5. Introduction of RsptxABCD into Wild-type Strain of *E. coli* and Growth on Phosphorous Acid Culture Medium] above, except (i) that culture was performed without sterilization treatment on an MOPS-Pt culture medium and on a conical flask and (ii) that a silicon stopper was not used during the culture, but the culture was performed in an open system.

For confirmation of the presence or absence of contamination at the end of the culture, 40 μL of a 2×10$^5$-fold diluted solution of the culture solution after 16 hours was spread onto a 2×YT plate containing chloramphenicol, and another 40 μL of the diluted solution was spread onto a 2×YT plate containing no chloramphenicol. These plates were cultured all night long at 37° C. The numbers of colonies that appeared on the plates were counted for comparison.

Figure 8:
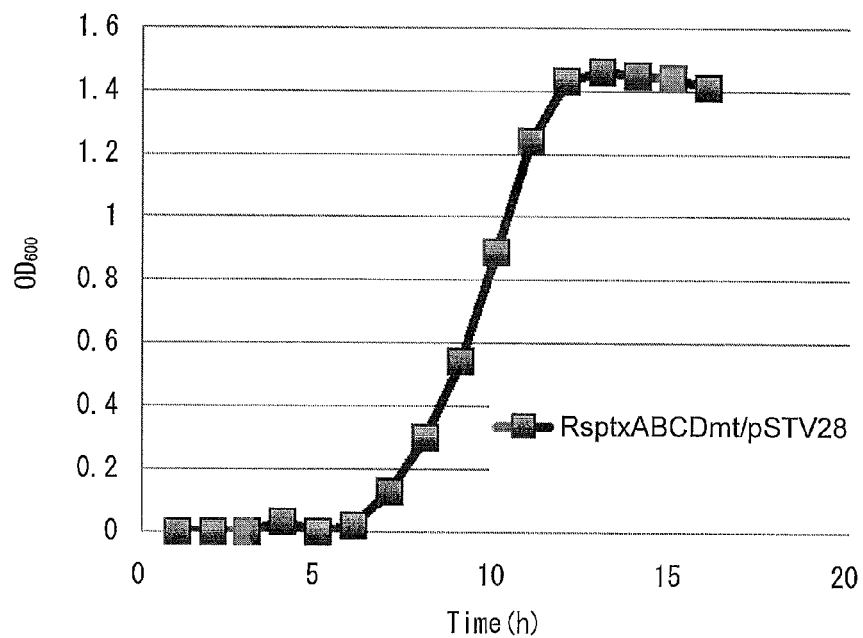

FIG. 8 is a graph showing a change over time in $OD_{600}$ of transformants of *E. coli* MG1655 into which RsptxABCDmt/pSTV28 has been introduced and which are cultured on an unsterilized culture medium and in an open system.

The growth rate (0.476 h$^{-1}$) and the final $OD_{600}$ (1.45) were both substantially equal to those obtained in the case shown in FIG. 7 where a sterilized culture medium was used. Further, no significant difference was found between the number of colonies in the culture medium containing no chloramphenicol (308±28 colonies/plate) and the number of colonies in the culture medium containing chloramphenicol (315±14 colonies/plate). In the culture medium containing chloramphenicol, transformants of *E. coli* MG1655 into which RsptxABCDmt/pSTV28 has been introduced can grow, but bacteria (unintended microorganisms) cannot grow. In the culture medium containing no chloramphenicol, both transformants of *E. coli* MG1655 into which RsptxABCDmt/pSTV28 has been introduced and bacteria can grow. It is presumable that if there is an increase in bacteria, the number of colonies in the culture medium containing no chloramphenicol will be ten or more times larger than the number of colonies in the culture medium containing chloramphenicol. This result means that contamination hardly occurs even in a case where culture is performed in an open system using an unsterilized culture medium.

[7. Stability of Plasmid Retention by Passage]

A subculture operation in which transformants of *E. coli* MG1655 into which RsptxABCDmt/pSTV28 had been introduced are cultured for approximately 12 hours in MOPS-Pt (0.5) and, after the growth, are inoculated again by 1% (v/v) into fresh MOPS-Pt (0.5) was repeated ten times.

Plasmid DNA was extracted from the obtained bacterial cells (equivalent amount of 1.0 mL at $OD_{600}=1.0$) by the alkali-SDS method, and was dissolved in 40 µL of sterilized water. 2 µL of the plasmid DNA solution was separated by agarose gel electrophoresis, and was stained with ethidium bromide for visualization.

Figure 9:
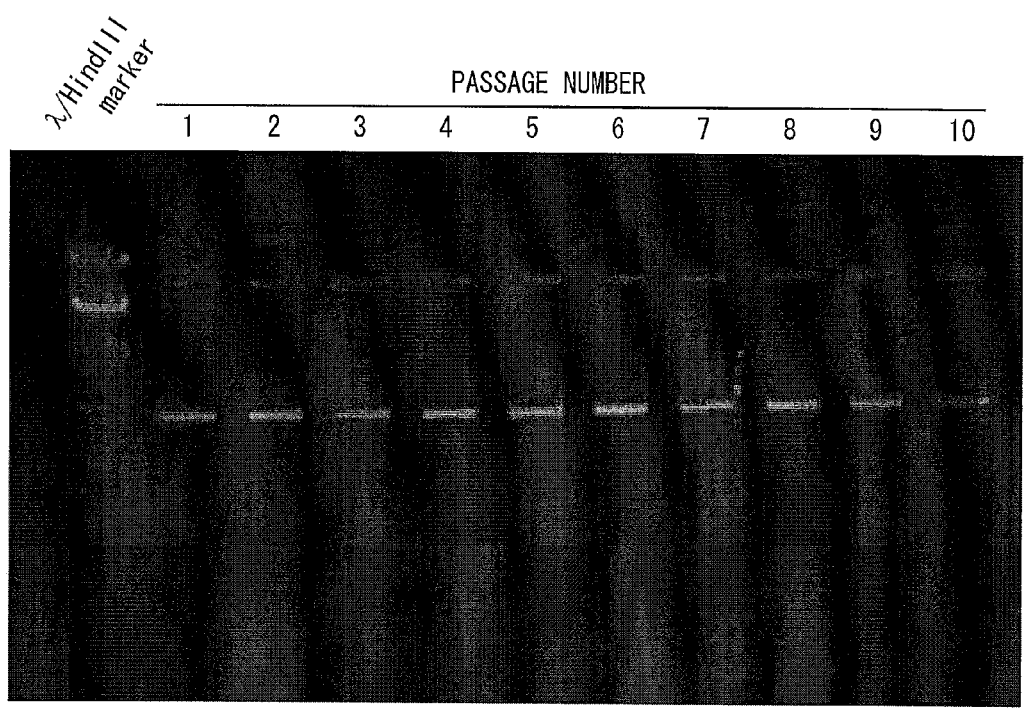

The agarose gel electrophoretic zymogram of that time is shown in FIG. 9. Subculture was performed ten times, but there was almost no change in concentration of plasmid DNA bands, so it was found that there was almost no change in amount of plasmid DNA in the bacterial cells. Therefore, it is conceivable that the plasmid DNA in the bacterial cells is stably retained. For this reason, it was confirmed that the selective culturing method of the present invention can be stably carried out.

[8. Stability of Plasmid Retention by Passage-2]

Figure 10:
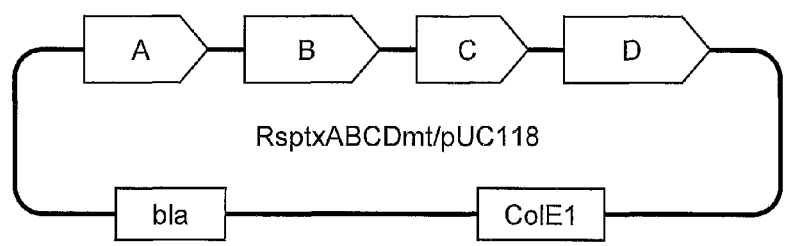

A DNA fragment (approximately 3.6 kb) obtained by EcoRI digestion of RsptxABCDmt/pSTV28 was introduced into an EcoRI site of pUC118 (Takara Bio Inc.). A plasmid in which promoter control and a gene in the DNA fragment are identical in orientation was chosen as RsptxABCDmt/pUC118 (See FIG. 10.).

RsptxABCDmt/pUC118 was introduced into *E. coli* MG1655, and *E. coli* MG1655 was applied onto a 2×YT plate (containing ampicillin), and was cultured overnight at 37° C. A single colony of transformants of *E. coli* MG1655 thus obtained was inoculated into a 2×YT liquid medium (containing 50 mg/L of ampicillin), and was cultured overnight at 37° C., whereby a preculture solution was prepared. 1.0 mL of the preculture solution was centrifuged to be separated into bacterial cells and a culture solution. In order to remove phosphoric acid derived from the culture medium, the pellet of the bacterial cells was resuspended in 1 mL of MOPS (0) containing no phosphorous component. 0.04 mL of the bacterial suspension was added to 4.0 mL of each of the following three MOPS culture media: an MOPS culture medium containing phosphoric acid (0.5 mM) as a sole phosphorous source (MOPS-Pi, Amp(−): 22.2 mM glucose, 40 mM potassium morpholinopropane sulfonate [pH 7.2], 50 mM NaCl, 9.52 mM $NH_4Cl$, 4 mM Tricine, 0.5 mM $K_2HPO_4$, 0.52 mM $MgCl_2$, 0.28 mM $K_2SO_4$, 0.01 mM $FeSO_4$, 0.0005 mM $CaCl_2$, 20 µM thiamine); an MOPS culture medium containing phosphoric acid (0.5 mM) as a sole phosphorous source and further containing ampicillin (MOPS-Pi, Amp(+): 22.2 mM glucose, 40 mM potassium morpholinopropane sulfonate [pH 7.2], 50 mM NaCl, 9.52 mM $NH_4Cl$, 4 mM Tricine, 0.5 mM $K_2HPO_4$, 0.52 mM $MgCl_2$, 0.28 mM $K_2SO_4$, 0.01 mM $FeSO_4$, 0.0005 mM $CaCl_2$, 20 µM thiamine, 50 mg/L ampicillin); and an MOPS culture medium containing phosphoric acid (0.5 mM) as a sole phosphorous source (MOPS-Pt (0.5): For the composition, see section [2. Introduction of RsptxABCD into *E. coli* and Growth on Phosphorous Acid Culture Medium] above).

A subculture operation in which the transformants of *E. coli* MG1655 were cultured overnight in the respective culture media and, after the growth, are inoculated again by 1% (v/v) into fresh media, respectively, was repeated five times.

Each time after primary culture and after second to sixth subcultures, plasmid DNA was extracted from the obtained bacterial cells (about $1 \times 10^8$ cells) by the alkali-SDS method, and was dissolved in 40 µL of sterilized water. 5 µL of the plasmid DNA solution was separated by agarose gel electrophoresis, and was stained with ethidium bromide for visualization.

Figure 11:
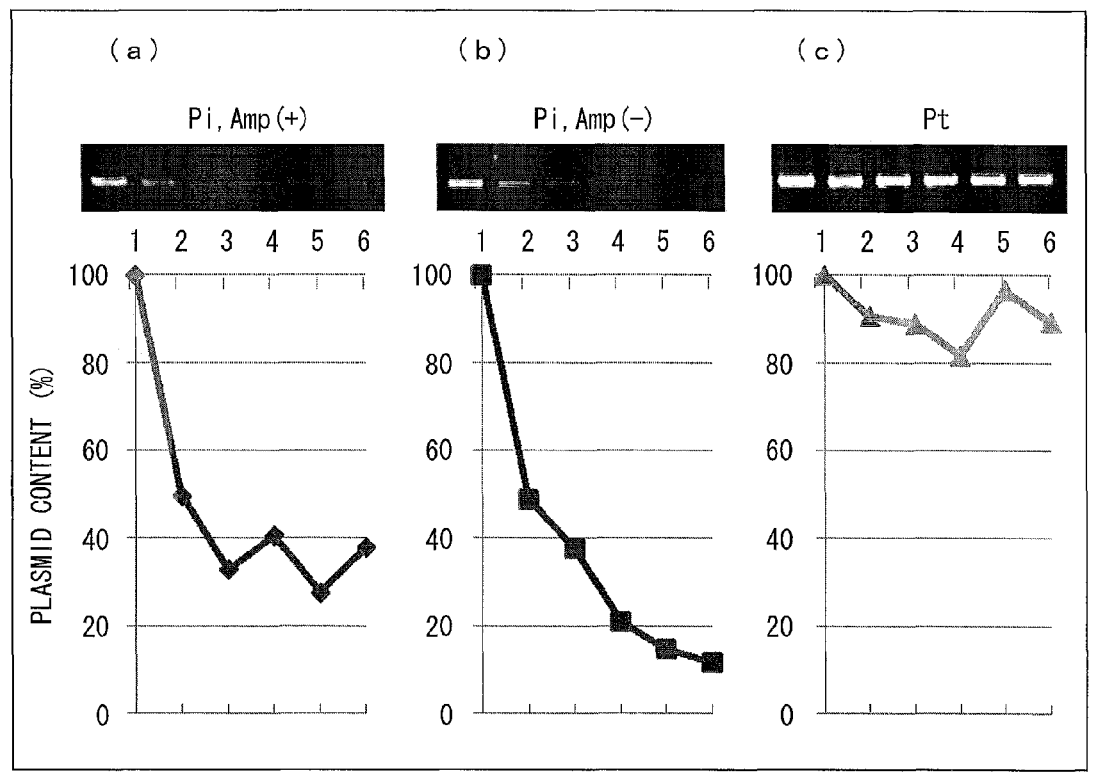

FIG. 11 is a set of photographic diagrams (a) to (c) showing a result of agarose gel electrophoresis performed on plasmid DNA prepared from transformants (after primary culture and after second to sixth subcultures) of *E. coli* MG1655 into which RsptxABCDmt/pUC118 have been introduced and graphs (a) to (c) showing changes in plasmid content of the transformants due to subculture. The horizontal axis of each graph represents passage number, and each band in the photographic diagrams corresponds to the passage number. That is, the leftmost band in the photographic diagrams is a band after primary culture. The graphs show changes based on the assumption that the plasmid content after primary culture is 100%. (a) of FIG. 11 shows a result of culturing the transformants on MOPS-Pi, Amp(+). (b) of FIG. 11 shows a result of culturing the transformants on MOPS-Pi, Amp(−). (c) of FIG. 11 shows a result of culturing the transformants on MOPS-Pt.

The bacterial cells cultured on the MOPS-Pi culture media showed decreased plasmid content as more and more subcultures are performed, regardless of whether or not ampicillin was contained. This is considered to be because the proportion of *E. coli* out of which plasmids dropped increased since an ampicillin-degrading enzyme (which is responsible for ampicillin resistance) degrades ampicillin contained in the culture medium. On the other hand, the bacterial cells cultured on the MOPS-Pt culture medium showed almost no change in concentration of bands of plasmid DNA, although subculture was performed six times. This shows that there was almost no change in amount of plasmid DNA in the bacterial cells as compared with the culture on the MOPS-Pi culture media.

Figure 12:
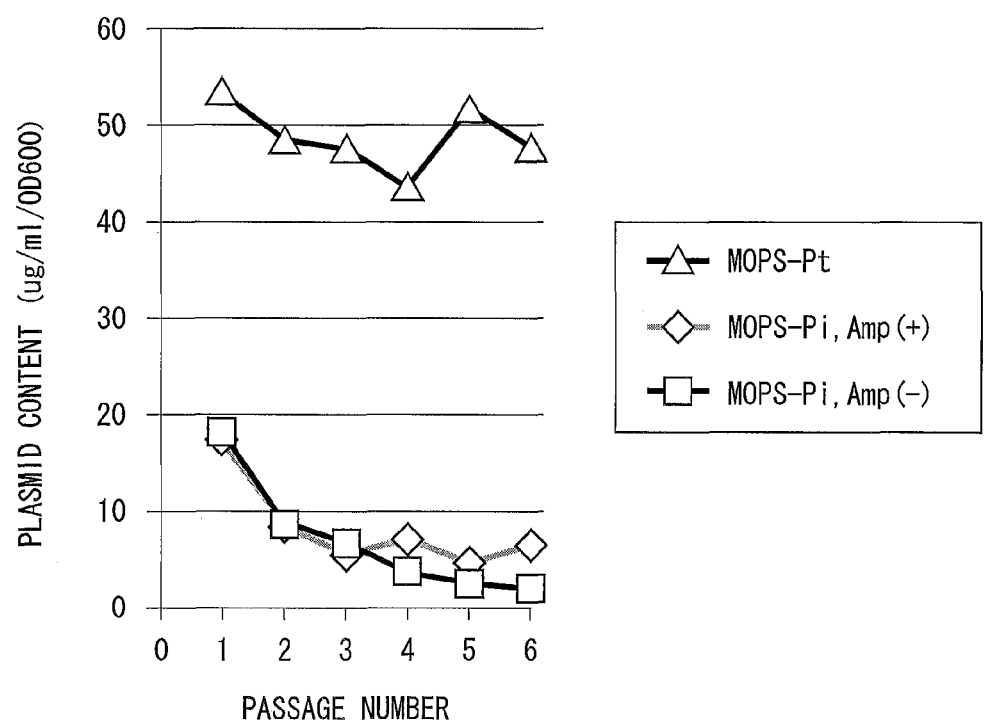

FIG. 12 is a graph showing the results in (a), (b), and (c) of FIG. 11 as changes in plasmid content (µg/mL/$OD_{600}$) of the transformants due to subculture. The plasmid DNA content was determined as follows: A plasmid DNA solution obtained was diluted as appropriate. The absorbance at 260 nm was measured by a spectrophotometer with a cell having an optical path length of 1.0 cm. The DNA concentration of the plasmid DNA solution as obtained by multiplying the obtained value by dilute strength and DNA concentration coefficient (50 µg/mL) was calculated. The plasmid content (µg/mL/$OD_{600}$) was a concentration of DNA plasmid extracted from bacterial cells equivalent to 1.0 mL of a culture solution having a bacterial concentration ($OD_{600}$) of 1.0.

FIG. 12 shows that the bacterial cells cultured on the MOPS-Pt culture medium not only show smaller changes in amount of plasmid DNA than those cultured on the MOPS-Pi culture medium, but also retain a larger number of copies of the plasmid. That is, it was confirmed that the selective culturing method of the present invention is also excellent in terms of making it possible to stably retain a large number of copies of the plasmid without using an antibiotic substance.

[9. Selective Culture of ptxD-introduced *E. Coli* in the Presence of a Competitive Strain]

Assuming a case where contamination has occurred, the growth of ptxD-introduced *E. coli* (hereinafter referred to also as "ptxD-introduced strain") in the presence of a competitive strain was examined. As the ptxD-introduced strain, ampicillin-resistant MG1655 was used, and as the competitive strain, kanamycin-resistant *E. coli* MG1655 (yjbB::Kmr) was used. The ptxD-introduced strain was obtained by the method described in section [8. Stability of Plasmid Retention by Passage-2].

The ptxD-introduced strain and the competitive strain were mixedly inoculated into MOPS culture media containing phosphorous acid (0.5 mM) as a sole phosphorous source (MOPS-Pt (0.5): For the composition, see section [2. Introduction of RsptxABCD into *E. coli* and Growth on Phosphorous Acid Culture Medium] above), and were cultured at 37° C. for 15 hours. The culture was performed by preparing MOPS-Pt (0.5) culture media into which the ptxD strain was inoculated together with the competitive strain in percentages of 10%, 20%, 30%, 40%, 50%, 60%, 70%, 80%, and 90% with respect to the total bacterial count at the time of mixed inoculation, respectively. In the following, the percentages of the ptxD-introduced strain and the competitive strain with respect to the total bacterial count are referred to simply as "percentage of the ptxD-introduced strain" and "percentage of the competitive strain", respectively. The total bacterial count in each of the MOPS-Pt (0.5) culture media was $4.0 \times 10^6$.

The cultures obtained from the respective MOPS-Pt (0.5) culture media were put on LB culture media containing ampicillin and LB culture media containing kanamycin, and were cultured at 37° C. for 10 hours. The bacterial counts of the ptxD-introduced strain and the competitive strain were determined from the number of colonies that appeared. That is, the bacterial counts of the ptxD-introduced strain were determined from the LB culture media containing ampicillin, and the bacterial counts of the competitive strain were determined from the LB culture media containing kanamycin. Assuming that A is the bacterial count (cfu) in an LB culture medium containing ampicillin and K is the bacterial count (cfu) in an LB culture medium containing kanamycin, the percentage D (%) of the ptxD-introduced strain at the end of culture is expressed as follows:

$$D = \{A/(A+K)\} \times 100$$

Figure 13:
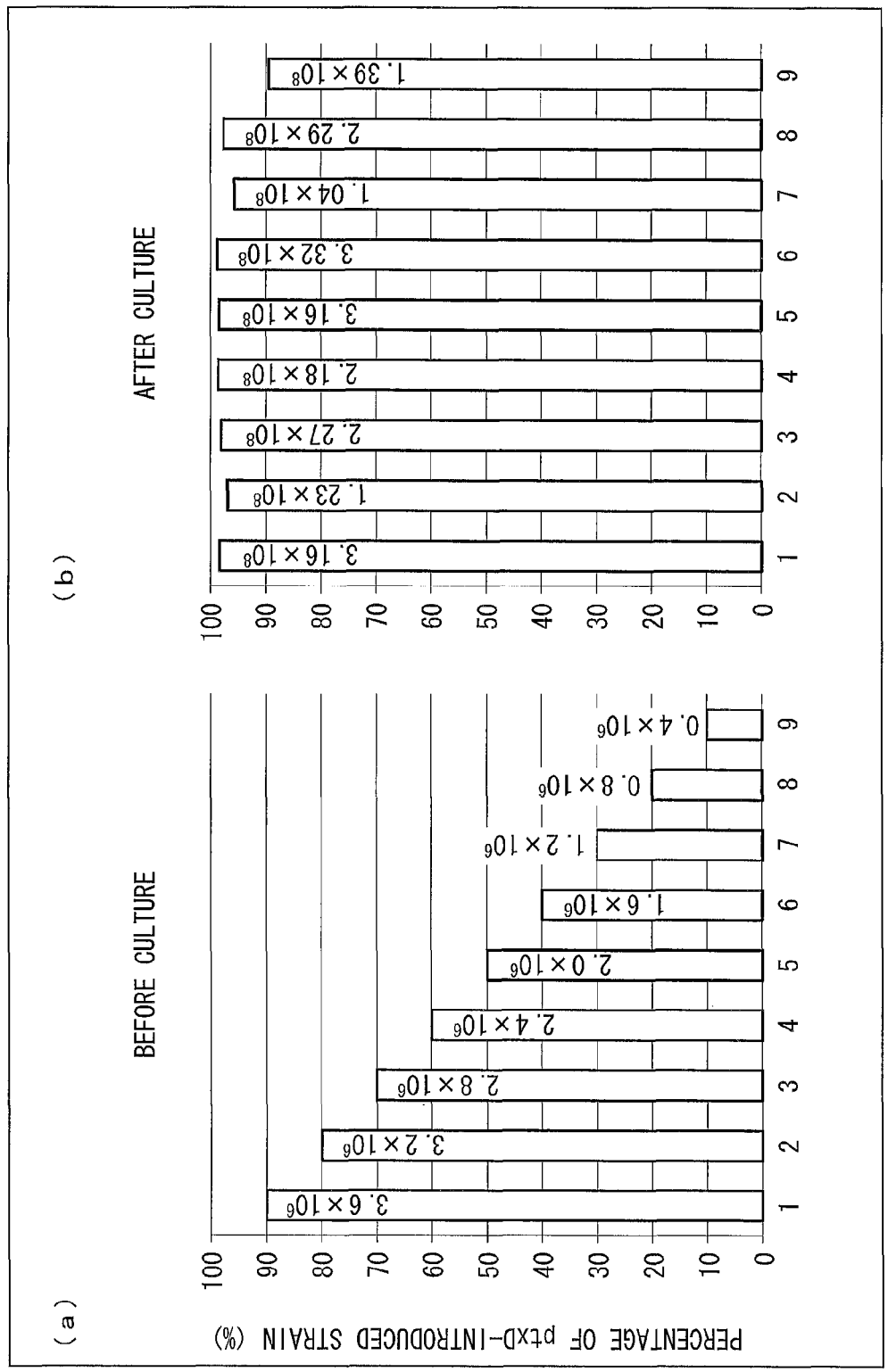

FIG. 13 is a set of diagrams (a) and (b) showing changes in the percentages of the ptxD-introduced strain between before culture and after culture. (a) of FIG. 13 shows the percentages of the ptxD-introduced strain before culture, (b) of FIG. 13 shows the percentages of the ptxD-introduced strain after culture. Numbers on each of the horizontal axis of FIG. 13 indicate correspondence between culture media, and indicate that data assigned the same number in (a) and (b) of FIG. 13 are derived from the same culture medium. Each of the bars is assigned a numerical value that indicates the cell count of the ptxD-introduced strain. In a case where the percentages of the ptxD-introduced strain before culture were 20 to 90%, the percentages of the ptxD-introduced strain after culture were 95% or higher. Further, even in a case where the percentage of the ptxD-introduced strain before culture was 10%, the percentage of the ptxD-introduced strain after culture reached about 90%. That is, it was confirmed that the selective culturing method of the present invention is also excellent in terms of making it possible to preferentially culture the ptxD-introduced strain even in the presence of a competitive strain due to contamination or the like.

[10. Determination of the Capability of Yeast to Utilize Phosphorous Acid]

The selective growth of ptxD introduced into a target yeast strain is based on the premise that the host does not have the capability to utilize phosphorous acid. Accordingly, whether fission yeast has the capability to utilize phosphorous acid was examined.

The strains used were *Schizosaccharomyces pombe* (*Sz. pombe*) strain L972 (h−) and *Schizosaccharomyces pombe* (*Sz. pombe*) strain L975 (h+) (both of which are wild-type strains). In preculture, these yeast strains were cultured at 30° C. for 24 hours with Yeast extract-Peptone-Dextrose (YPD) culture medium (1.0% yeast extract, 2.0% peptone, 2% glucose). 1 mL of each of the bacterial culture solutions thus obtained was transferred into a microtube, and bacterial cells were deposited by centrifugation (3,000×g, 3 minutes). After a supernatant had been removed from the microtube, the bacterial cells were suspended in 1 mL of sterilized water and centrifuged again to be deposited. This operation was repeated three times, and the bacterial cells were washed. After that, the concentration of the bacterial suspension was adjusted with sterilized water so that the bacterial concentration was 1.0 in terms of OD600 value.

40 μL of the bacterial suspension were inoculated into a culture medium with 4 mL of Edinburgh minimal medium (EMM2) minimal medium (Forsburg S. & Rhind N., Yeast, 23:173-183, 2006), and were cultured at 28° C. In determining the capability to utilize phosphorous acid, three types of the culture medium were prepared for use in testing, namely a culture medium (none) having no phosphorous source, a culture medium (Pi) containing phosphoric acid as a phosphorous source, and a culture medium (Pt) containing phosphorous acid as a phosphorous source. Each of the three types of culture medium was prepared in solid and liquid forms.

The following shows how the culture media were prepared. For the preparation of a solid medium with agar, agar subjected to washing operation for removal of minute amounts of phosphoric acid contained in agar was used. For example, 50 mL of a solid medium was prepared with agar obtained by repeating three times an operation of putting 1.2 g of purified agar powder and 50 mL of deionized water into a centrifuging tube, mixing them by overturning for 5 minutes, centrifuging the mixture at 1,500 rpm for 3 minutes to cause agar to be deposited, and discarding the supernatant. A phosphoric acid solution and a phosphorous acid solution were prepared at a concentration of 1 M with a pH of 7.0, and were disinfected by filtration. In all of the culture media prepared with EMM2 culture media, components excluding the phosphorous source were autoclaved. After that, the phosphoric acid solution or the phosphorous acid solution were added to the EMM2 culture media so that the final concentration was 15 mM, whereby the culture medium containing phosphoric acid as the phosphorous source and a culture medium containing phosphorous acid as a phosphorous source were prepared.

Figure 14:
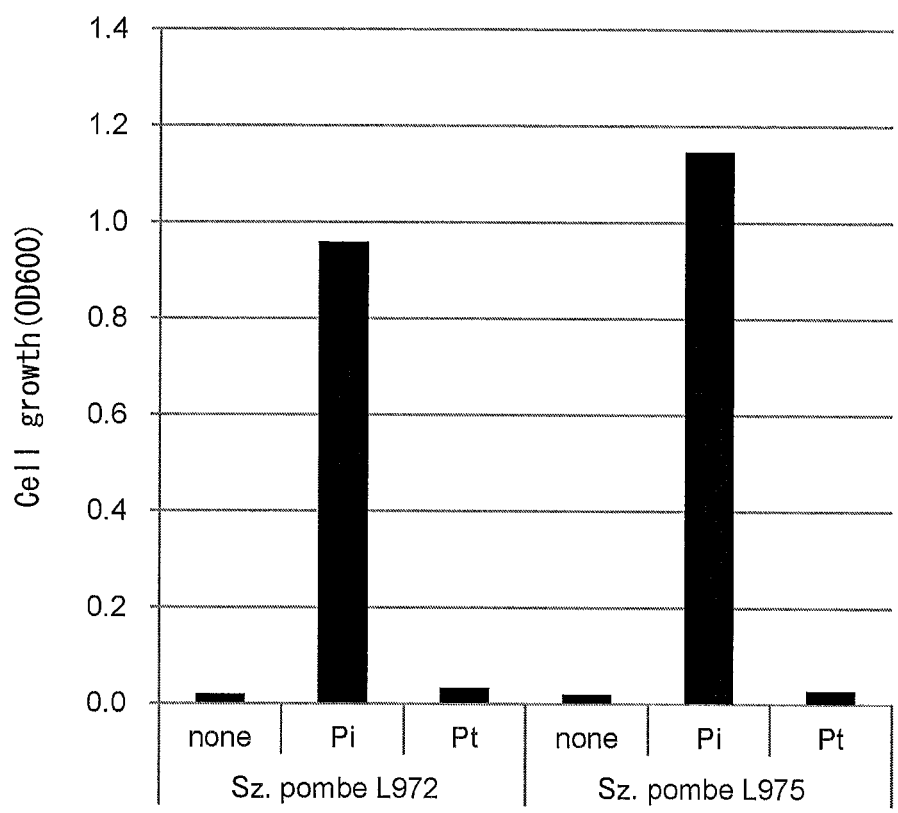

The results are shown in FIGS. 14 and 15. FIG. 14 is a graph showing results of culturing strains L972 and L975 of fission yeast (*Sz. pombe*) on liquid media for 40 hours, the legend "none" representing a result of culture on a culture medium having no phosphorous source, the legend "Pi" representing a result of culture on a culture medium containing phosphoric acid as a phosphorous source, the legend "Pt" representing a result of culture on a culture medium containing phosphorous acid as a phosphorous source. FIG. 15 is a set of photographic diagrams (a) and (b) showing results of culturing strains L972 and L975 of fission yeast on solid media for 4 days, the photographic diagram (a) showing a result of culture on a culture medium (Pi) containing phosphoric acid as a phosphorous source, the photographic diagram (b) showing a result of culture on a culture medium (Pt) containing phosphorous acid as a phosphorous source. Fission yeast exhibited growth on a minimal medium containing phosphoric acid as a phosphorous source, but did not grow on a culture medium containing phosphorous acid as a phosphorous source. Similar results were obtained from both the liquid and solid media. No extension of culture time brought about a difference in outcome. This made it clear that fission yeast cannot utilize phosphorous acid as a phosphorous source.

[11. Introduction of ptxD into Fission Yeast and Phosphorous Acid Dependent Growth]

As mentioned above, it is now clear that fission yeast cannot utilize phosphorous acid as a phosphorous source. Therefore, if it is possible to functionally express ptxD by introducing it into a yeast strain, it is possible to cause ptxD to grow by utilizing phosphorous acid as a sole phosphorous source. In the present experiment, two types of bacteria-derived ptxD genes were introduced into fission yeast, and whether phosphorous acid can be utilized was considered.

(11-1. Preparation of PtxD Expression Plasmids)

Expression plasmids were prepared with a pDUAL vector known as a protein expression system in *Sz. pombe* (Matsuyama A. et al, *Yeast*, 21: 1289-1305, 2004). This vector comes in three different types of plasmid, namely high (HFF1), middle (HFF41), and low (HFF81), depending on promoter strength, and the construction of expression strains with these plasmids was believe to bring about findings about a relationship between PtxD expression intensity and growth.

PtxD expression plasmids were prepared with In-Fusion HD Cloning System (Takara Bio Inc.). First, ptxD (RsptxD, SEQ ID NO: 2) derived from *Ralstonia* sp. strain 4506 was amplified by PCR using the primers listed below, with *Ralstonia* sp. strain 4506 chromosome DNA as a template.

```
pombe_RsptxD IF fw:
                                   (SEQ ID NO: 26)
5'-caccatcatcatatgAAGCCCAAAGTCGTCCTCAC-3' pombe_RsptxD IF rv:
                                   (SEQ ID NO: 27)
5'-atcatccttataatcTCACGCCGCCTTTACTCCCG-3'
```

Further, similarly, ptxD (PsptxD, SEQ ID NO: 28) derived from *Pseudomonas stutzeri* was amplified by PCR using the primers listed below, with *P. stutzeri* chromosome DNA as a template (the amino acid sequence of a protein encoded by the nucleotide sequence of SEQ ID NO: 28 is indicated by SEQ ID NO: 29).

```
pombe_PsptxD IF fw:
                                   (SEQ ID NO: 30)
5'-caccatcatcatatgCTGCCGAAACTCGTTATAAC-3' pombe_PsptxD IF rv:
                                   (SEQ ID NO: 31)
5'-atcatccttataatcTCAACATGCGGCAGGCTCGGC-3'
```

Lower-case portions of the sequences mean additional sequences of 15 bases that are needed in In-Fusion Cloning reaction.

Further, as vector DNA, PCR was performed using the primers listed below, with pDUAL-HFF1, pDUAL-HFF41, and pDUAL-HFF81 as templates. An amplified DNA fragment of approximately 7 kb was used as a linearized vector for the reaction.

```
pDUAL_rv:
                                   (SEQ ID NO: 32)
5'-CATATGATGATGGTGGTGATGCATAG-3' pDUAL_fw:
                                   (SEQ ID NO: 33)
5'-GATTATAAGGATGATGACGATAAAC-3'
```

The DNA fragment thus obtained was purified and reaction was performed according to the instructions of the kit. A target clone was obtained by transforming *E. coli* DH5a with the reaction product. The ptxD sequence of the plasmid thus obtained was determined by a DYEnamic ET Terminator (Applied Biosystems) for confirmation of correct introduction of the target DNA sequence. The specific method complied with the protocol attached to the DYEnamic ET Terminator. Through these operations, a total of six types of PtxD expression plasmid were constructed, namely RsPtxD/HFF1, RsPtxD/HFF41, RsPtxD/HFF81, PsPtxD/HFF1, PsPtxD/HFF41, and PsPtxD/HFF81.

(11-2. Introduction of PtxD Expression Plasmids (Chromosome Transfer Type))

The PtxD expression plasmids thus prepared were introduced into chromosomes of *Sz. pombe* by a lithium acetate method using linearized plasmids. This method allows a target gene to be inserted onto a genome by a single copy. This makes it possible to compare impacts of the intensities of the three types of promoter.

Specifically, transformation was performed according to the following procedure. First, the target strain, *Sz. pombe* strain 635 (leu1-32), was cultured all night long in 4 mL of a YE (5S) liquid medium (obtained by dissolving adenine sulfate, uracil, leucine, histidine-HCl, and lysine in a medium containing 3% glucose and 0.5% yeast extracts so that the final concentrations of adenine sulfate, uracil, leucine, histidine-HCl, and lysine were each 100 µg/mL), and a culture solution of about OD600=0.5 was centrifuged so that bacterial cells were deposited. A supernatant was removed with a pipette, and the cells were washed with sterilized water. The culture solution was centrifuged again. A supernatant was discarded, and the cells were suspended in 0.3 mL of a lithium acetate solution (0.1 M Lithium-acetate, TE (10 mM Tris-HCl, 1 mM EDTA) pH 7.5). The culture solution was centrifuged again. The lithium acetate solution was removed, and the cells were suspended in 0.3 mL of a lithium acetate solution. Into 100 µL of the cell suspension, a plasmid DNA solution (<10 µL, approximately 1 µg) linearized by treatment with restriction enzyme NotI was mixed together with 2 µL of Carrier DNA (salmon sperm DNA). The mixture stood still at room temperature for 10 minutes. After that, 260 µL of 50% PEG (polyethylene glycol (average MW 3350) 50% (w/v) in water) were added, and the mixture thus obtained stood still at room temperature for 60 minutes. After that, 43 µL of DMSO was added, and the mixture thus obtained was stirred well. After that, incubation was performed at 42° C. for 5 minutes. The cells were washed twice with sterilized water in the same manner as that described above, and were suspended in 0.3 mL of sterilized water. 0.1 mL of the cell suspension was put on an EMM2 solid medium (Leu⁻) containing phosphorous acid or phosphoric acid as a phosphorous source. The cells were cultured at 30° C. for about 3 to 5 days to give transformants.

(11-3. Growth of ptxD-introduced Sz. Pombe on a Phosphorous Acid Culture Medium)

The colony of transformants thus obtained was inoculated into a YPD culture medium, and were cultured all night long. By washing the culture solution in the same manner as in section [10. Determination of the Capability of Yeast to Utilize Phosphorous Acid], a bacterial suspension was prepared. 40 µL of the bacterial suspension were inoculated into an EMM2 culture medium (4 mL) containing phosphorous acid or phosphoric acid as a phosphorous source, and the bacteria were cultured at 28° C. The OD600 value was measured over time.

The results are shown in FIGS. 16 and 17. FIG. 16 is a set of photographic diagrams (a) and (b) showing results of culturing transformants of Sz. pombe on solid media. (a) of FIG. 16 shows a result of culture on a culture medium (Pi) containing phosphoric acid as a phosphorous source, and (b) of FIG. 16 shows a result of culture on a culture medium (Pt) containing phosphorous acid as a phosphorous source. FIG. 17 is a set of graphs showing results of culturing transformants of fission yeast on liquid media. (a) of FIG. 17 shows a result of culture on a culture medium (Pi) containing phosphoric acid as a phosphorous source, and (b) of FIG. 17 shows a result of culture on a culture medium (Pt) containing phosphorous acid as a phosphorous source. The legend "Rs-1" represents RsPtxD/HFF1-introduced strain. The legend "Rs-41" represents an RsPtxD/HFF41-introduced strain. The legend "Rs-81" represents an RsPtxD/HFF81-introduced strain. The legend "Ps-1" represents a PsPtxD/HFF1-introduced strain. The legend "Ps-41" represents a PsPtxD/HFF41-introduced strain. The legend "Ps-81" represents a PsPtxD/HFF81-introduced strain. The legend "Control" represents a pDUAL-HFF41-introduced strain.

Those strains of Sz. pombe which express RsPtxD and PsPtxD under control of an HFF1 promoter, respectively, exhibited growth after about 4 days of culture on a culture medium containing phosphorous acid as a phosphorous source ((b) of FIG. 16). On the other hand, the strain into which the control plasmid had been introduced exhibited no growth. Those constructs under control of HFF41 and HFF81, respectively, exhibited weak growth when cultured for an extended period of time. These results demonstrated that the expression of PtxD in fission yeast allows the fission yeast to grow on phosphorous acid as a phosphorous source.

In the case of liquid media, too, those strains of Sz. pombe which express RsPtxD and PsPtxD under control of an HFF1 promoter, respectively, exhibited satisfactory growth on a culture medium containing phosphorous acid as a phosphorous source ((b) of FIG. 17). The final OD was at a level that compared favorably with that attained when phosphoric acid was used. An expression system under HFF41 control exhibited growth, albeit inferior to the case under HFF1 control. The PtxD activity of the cell crude extract was measured by a measuring method described in [4. Alteration of RsPtxD to NADP-utilizing Type by Site-specific Introduction of Mutation], whereby it was found that there was a proportional relation between promoter intensity and PtxD activity. These results demonstrated that phosphorous acid dependent growth depends on the intensity of PtxD expression.

Since the characteristics of growth on liquid media were such that the same degree of growth was exhibited no matter whether RsPtxD or PsPtxD was used, there appears to be no great difference in function between them.

As described above, the introduction of ptxD allowed Sz. pombe to grow on phosphorous acid, which Sz. pombe cannot utilized by nature. That is, a possibility was indicated that PtxD can be used as a marker for Sz. pombe. Further, it became clear that the rate of phosphorous acid dependent growth depends on the intensity of PtxD expression. Furthermore, it became clear that both of the two types of PtxD (PtxD (RsPtxD) derived from Ralstonia sp. 4506 and PtxD (PsPtxD) derived from Pseudomonas sp.) bring about the same effect.

[12. Selective Culture of Fission Yeast Retaining ptxD-introduced Plasmid]

In a case where PtxD is used as a marker, a case is supposed where it is used by being introduced into a plasmid. Accordingly, whether a PtxD expression plasmid functionally acts when retained in a cell and whether a strain transformed by a PtxD expression plasmid can be selectively screened on a phosphorous acid minimal medium were examined.

The strain used was Sz. pombe KSP632 (ura4-D18). The plasmid used was RsPtxD/HFF1 prepared in section (11-1. Preparation of PtxD Expression Plasmids). As a control plasmid, pDUAL-HFF1 was used. Transformation of the strain by the plasmid was performed in the same manner as in (11-2. Introduction of PtxD Expression Plasmids (Chromosome Transfer Type)), except that use of restriction enzyme treatment and Carrier DNA was unnecessary. Bacterial solutions after transformation operations were each put on three types of EMM2 solid medium, namely a culture medium (none) having no phosphorous source, a culture medium (Pi) containing phosphoric acid as a phosphorous source, and a culture medium (Pt) containing phosphorous acid as a phosphorous source, and were cultured at 28° C. for 7 days.

The results are shown in FIG. 18. (a) of FIG. 18 is a photographic diagram showing results for transformants into which the control plasmid had been introduced, and (b) of FIG. 18 is a photographic diagram showing results of transformants into which the RsPtxD/HFF1 plasmid had been introduced. In each of the photographic diagrams (a) and (b), (i) shows a result of culture on a culture medium (none) having no phosphorous source, (ii) shows a result of culture on a culture medium (Pi) containing phosphoric acid as a phosphorous source, and (iii) shows a result of culture on a culture medium (Pt) containing phosphorous acid as a phosphorous source. Further, (iv), (v), and (vi) show enlarged views of (i), (ii), and (iii) respectively.

The fission yeast into which the control plasmid had been introduced and the fission yeast into which the RsPtxD/HFF1 plasmid had been introduced both formed colonies on EMM2 plates containing phosphoric acid as a phosphorous source ((ii) of (a) of FIG. 18 and (ii) of (b) of FIG. 18). From this, it was confirmed that the plasmids had been transformed into the target strains, respectively. However, while the strain into which the control plasmid had been introduced was not able to grow at all on a plate containing phosphoric acid as a phosphorous source, the strain into which RsptxD had been introduced formed a colony on a plate containing phosphoric acid as a phosphorous source ((iii) of (a) of FIG. 18 and (iii) of (b) of FIG. 18).

From this, it became clear that the introduction of ptxD makes it possible to easily discriminate between transformants on plates. Further, also in a case where RsPtxD/HFF41 was used, transformants were obtained (no data shown), albeit in a small number. This means that even in a case where a weak promoter is used, phosphorous acid dependent growth is possible, provided there are such a number of copies of ptxD that a sufficient level of protein expression can be ensured for exhibition of the capability to utilize phosphorous acid. These results show that ptxD can be utilized as a useful selective marker for yeast.

[13. Selective Culture of ptxD-introduced E. Coli in the Presence of a Competitive Strain-2]

Assuming a case where contamination has occurred, the growth of ptxD-introduced E. coli in the presence of a competitive strain was examined. As the ptxD-introduced strain, ampicillin-resistant MG1655 was used, and as the competitive strain, *Bacillus subtilis*, which does not utilize phosphorous acid, was used. The ptxD-introduced strain was obtained by the method described in section [8. Stability of Plasmid Retention by Passage-2].

The ptxD-introduced strain and the competitive strain were mixedly inoculated into MOPS culture media containing phosphorous acid (0.5 mM) as a sole phosphorous source (MOPS-Pt (0.5): For the composition, see section [2. Introduction of RsptxABCD into *E. coli* and Growth on Phosphorous Acid Culture Medium] above), and were cultured at 37° C. for 15 hours. The culture was performed by preparing MOPS-Pt (0.5) culture media into which the ptxD strain was inoculated together with *B. subtilis* in percentages of 2.9%, 13.4%, 24.6%, 42.4%, 55.8%, 66.2%, 74.6%, 81.5%, 87.3%, 92.2%, and 96.4% with respect to the total bacterial count at the time of mixed inoculation, respectively. In the following, the percentages of the ptxD-introduced strain and the competitive strain with respect to the total bacterial count are referred to simply as "percentage of the ptxD-introduced strain" and "percentage of the competitive strain", respectively. The total bacterial count in each of the MOPS-Pt (0.5) culture media was $1.4 \times 10^6$ to $3.7 \times 10^6$.

The cultures obtained from the respective MOPS-Pt (0.5) culture media were put on LB culture media containing ampicillin and normal LB culture media, and were cultured at 37° C. for 10 hours. The bacterial counts of the ptxD-introduced strain and the competitive strain were determined from the number of colonies that appeared. Since a colony of *B. subtilis* is clearly distinguishable in morphology from a colony of *E. coli*, measurements were performed by counting the number of colonies on the LB culture media. That is, the bacterial counts of the ptxD-introduced strain were determined from the LB culture media containing ampicillin, and the bacterial counts of the competitive strain were determined from the normal LB culture media. Assuming that A is the bacterial count (cfu) in an LB culture medium containing ampicillin and B is the bacterial count (cfu) of *B. subtilis* in a normal LB culture medium, the percentage D (%) of the ptxD-introduced strain at the end of culture is expressed as follows:

$$D=\{A/(A+B)\} \times 100$$

Table 1 shows changes in the bacterial counts and percentages of the ptxD-introduced strain and *B. subtilis* between before culture and after culture.

TABLE 1

| | | | Culture Samples | | | | | |
|---|---|---|---|---|---|---|---|---|
| | | | 1 | 2 | 3 | 4 | 5 | 6 |
| Initial bacterial quantity | Bacterial count | ptxD | $3.6 \times 10^6$ | $3.2 \times 10^6$ | $2.8 \times 10^6$ | $2.4 \times 10^6$ | $2.0 \times 10^6$ | $1.6 \times 10^6$ |
| | | *B subtilis* | $1.36 \times 10^5$ | $2.72 \times 10^5$ | $4.08 \times 10^5$ | $5.44 \times 10^5$ | $6.80 \times 10^5$ | $8.16 \times 10^5$ |
| | Ratio (%) | ptxD | 96.4 | 92.2 | 87.3 | 81.5 | 74.6 | 66.2 |
| | | *B subtilis* | 3.6 | 7.8 | 12.7 | 18.5 | 25.4 | 33.8 |
| Bacterial quantity after culture | Bacterial count | ptxD | $6.63 \times 10^8$ | $5.40 \times 10^8$ | $3.69 \times 10^8$ | $4.71 \times 10^8$ | $1.91 \times 10^8$ | $2.66 \times 10^8$ |
| | | *B subtilis* | $6.20 \times 10^4$ | $1.20 \times 10^5$ | $1.70 \times 10^5$ | $1.80 \times 10^5$ | $3.60 \times 10^5$ | $3.10 \times 10^5$ |
| | Ratio (%) | ptxD | 100.0 | 100.0 | 100.0 | 100.0 | 99.8 | 99.9 |
| | | *B subtilis* | 0.0 | 0.0 | 0.0 | 0.0 | 0.2 | 0.1 |

| | | | Culture Samples | | | | |
|---|---|---|---|---|---|---|---|
| | | | 7 | 8 | 9 | 10 | 11 |
| Initial bacterial quantity | Bacterial count | ptxD | $1.2 \times 10^6$ | $8.0 \times 10^5$ | $4.0 \times 10^5$ | $2.0 \times 10^5$ | $4.0 \times 10^4$ |
| | | *B subtilis* | $9.52 \times 10^5$ | $1.09 \times 10^6$ | $1.22 \times 10^6$ | $1.29 \times 10^6$ | $1.35 \times 10^6$ |
| | Ratio (%) | ptxD | 55.8 | 42.4 | 24.6 | 13.4 | 2.9 |
| | | *B subtilis* | 44.2 | 57.6 | 75.4 | 86.6 | 97.1 |
| Bacterial quantity after culture | Bacterial count | ptxD | $3.54 \times 10^8$ | $2.28 \times 10^8$ | $2.22 \times 10^8$ | $1.34 \times 10^8$ | $1.74 \times 10^8$ |
| | | *B subtilis* | $5.60 \times 10^5$ | $5.30 \times 10^5$ | $5.80 \times 10^5$ | $7.40 \times 10^5$ | $6.20 \times 10^5$ |
| | Ratio (%) | ptxD | 99.8 | 99.8 | 99.7 | 99.5 | 99.6 |
| | | *B subtilis* | 0.2 | 0.2 | 0.3 | 0.5 | 0.4 |

FIG. 19 is a set of diagrams (a) and (b) showing changes in the percentages of the ptxD-introduced strain between before culture and after culture. That is, FIG. 19 is a diagrammatic representation of the experimental results shown in Table 1. (a) of FIG. 19 shows the percentages of the ptxD-introduced strain before culture, (b) of FIG. 19 shows the percentages of the ptxD-introduced strain after culture. Numbers on each of the horizontal axis of FIG. 19 indicate correspondence between culture media, and indicate that data assigned the same number in Table 1 and (a) and (b) of FIG. 19 are derived from the same culture medium. Each of the bars is assigned a numerical value that indicates the cell count of the ptxD-introduced strain. In either condition, the percentage of the ptxD-introduced strain after culture reached 99% or higher. That is, it was confirmed that the method of the present invention for selectively culturing a ptxD-introduced strain can prevent the growth of other species of microorganism for a long time.

[14. Selective Culture of ptxD-introduced *E. Coli* in the Presence of a Competitive Strain-3]

Long-term selective culture was examined under the same conditions as those of No. 11 of Table 1 of section [13. Selective Culture of ptxD-introduced *E. coli* in the Presence of a Competitive Strain-2] above. That is, ptxD-introduced strain 3% and *B. subtilis* 97% (total bacterial count 1.5×10⁶) were inoculated together into an MOPS culture medium containing phosphorous acid (0.5 mM) as a sole phosphorous source (MOPS-Pt (0.5): For the composition, see section [2. Introduction of RsptxABCD into *E. coli* and Growth on Phosphorous Acid Culture Medium] above), and were cultured at 37° C. for 0 hour, 24 hours, 48 hours, or 72 hours. The bacterial count was measured by the same method as that described in section [13. Selective Culture of ptxD-introduced *E. coli* in the Presence of a Competitive Strain-2] above.

The results are shown in Table 2.

TABLE 2

| Culture time | 0 h | 24 h | 48 h | 72 h |
| --- | --- | --- | --- | --- |
| ptxD-introduced strain | $4.73 \times 10^4$ | $2.08 \times 10^8$ | $2.01 \times 10^8$ | $2.00 \times 10^8$ |
| *B. subtilis* | $2.13 \times 10^6$ | $1.34 \times 10^6$ | $8.47 \times 10^5$ | $1.19 \times 10^6$ |
| Total bacterial count | $2.18 \times 10^6$ | $2.09 \times 10^8$ | $2.02 \times 10^8$ | $2.01 \times 10^8$ |

Further, FIG. 20 is a diagrammatic representation of the experimental results shown in Table 2. It was confirmed by the experimental results that even in the case of long-term selective culture under conditions where a competitive strain having no capability to utilize phosphorous acid is present in 30 or more times as high a percentage, the competitive strain does not grow but only the ptxD-introduced strain selectively grow.

The present invention is not limited to the description of the embodiments above, but may be altered by a skilled person within the scope of the claims. An embodiment and/or example based on a proper combination of technical means disclosed in different embodiments and/or examples is encompassed in the technical scope of the present invention.

INDUSTRIAL APPLICABILITY

The present invention is widely applicable to the field of production of substances using microorganisms, such as the production of biofuels.

The invention claimed is:

1. A method for selectively culturing a recombinant microorganism, the method comprising the step of culturing, in a culture medium containing phosphorous acid as a sole phosphorous source and containing no antibiotic substance, a recombinant microorganism transformed with a plasmid comprising a phosphite dehydrogenase gene,
   wherein the culturing is for 15 hours or longer under both sterile conditions and unsterile conditions,
   wherein the recombinant microorganism is further transformed with a phosphite transporter gene,
      wherein the phosphite transporter gene consists of polynucleotides encoding RsPtxA, RsPtxB, and RsPtxC, respectively, RsPtxA, RsPtxB, and RsPtxC constituting polypeptides of a phosphite transporter;
      RsPtxA is a protein consisting of the amino acid sequence of SEQ ID NO: 3 or a protein consisting of the amino acid of SEQ ID NO: 3 with a deletion, substitution, or addition of ten or less amino acids in the amino acid sequence of SEQ ID NO: 3 and functioning as the phosphite transporter when associated with RsPtxB and RsPtxC;
      RsPtxB is a protein consisting of the amino acid sequence of SEQ ID NO: 4 or a protein consisting of the amino acid of SEQ ID NO: 4 with a deletion, substitution, or addition of ten or less amino acids in the amino acid sequence of SEQ ID NO: 4 and functioning as the phosphite transporter when associated with RsPtxA and RsPtxC; and
      RsPtxC is a protein consisting of the amino acid sequence of SEQ ID NO: 5 or a protein consisting of the amino acid of SEQ ID NO: 5 with a deletion, substitution, or addition of ten or less amino acids in the amino acid sequence of SEQ ID NO: 5 and functioning as the phosphite transporter when associated with RsPtxA and RsPtxB,
      wherein the phosphite transporter gene used to transform the microorganism comprises a ribosome binding region upstream of said polynucleotide encoding RsPtxA, wherein said ribosome binding region is a Ralstonia sp. strain 4506 ribosome binding region that is upstream of RsPtxA gene in the chromosome of Ralstonia sp. strain 4506, and wherein guanine (G) located eight nucleotides upstream of the start codon of the RsPtxA gene of Ralstonia sp. strain 4506 is replaced with adenine (A) in said ribosome binding region.

2. The method as set forth in claim 1, wherein the unsterile conditions are conditions under which a culture apparatus and a culture medium have not been sterilized.

3. The method as set forth in claim 1, wherein the culturing is performed in 10 L or more of a culture medium.

4. The method as set forth in claim 1, wherein the culturing is performed in an open system.

5. The method as set forth in claim 1, further comprising the step of increasing the number of copies of the plasmid in the recombinant microorganism.

6. The method as set forth in claim 1, wherein the phosphite dehydrogenase gene is an NADP-utilizing phosphite dehydrogenase gene.

7. The method as set forth in claim 1, wherein the phosphite dehydrogenase gene is a polynucleotide encoding a protein of (a) or (b):
   (a) a protein consisting of the amino acid sequence of SEQ ID NO: 1; and (b) a protein consisting of the amino acid sequence of SEQ ID NO: 1 with a deletion, substitution, or addition of ten or less amino acids in the amino acid sequence of SEQ ID NO: 1 and having phosphite dehydrogenase activity.

8. The method as set forth in claim 1, wherein the phosphite dehydrogenase gene is a polynucleotide consisting of the nucleotide sequence of SEQ ID NO: 2.

9. The method as set forth in claim 1, wherein:
the polynucleotide encoding RsPtxA is a polynucleotide comprising the nucleotide sequence of SEQ ID NO: 6;

the polynucleotide encoding RsPtxB is a polynucleotide comprising the nucleotide sequence of SEQ ID NO: 7; and the polynucleotide encoding RsPtxC is a polynucleotide comprising the nucleotide sequence of SEQ ID NO: 8.

10. The method as set forth in claim 6, wherein the NADP-utilizing phosphite dehydrogenase gene is a polynucleotide encoding a protein of (a) or (b):

(a) a protein consisting of the amino acid sequence of SEQ ID NO: 9, 10, or 11; and (b) a protein consisting of the amino acid sequence of SEQ ID NO: 9, 10, or 11 with a deletion, substitution, or addition of ten or less amino acids in the amino acid sequence of SEQ ID NO: 9, 10, or 11 and having NADP-utilizing phosphite dehydrogenase activity.

11. The method as set forth in claim 6, wherein the NADP-utilizing phosphite dehydrogenase gene is a polynucleotide consisting of the nucleotide sequence of SEQ ID NO: 12, 13, or 14.

12. The method as set forth in claim 1, wherein the microorganism is further transformed with a polynucleotide comprising the nucleotide sequence of SEQ ID NO: 15.

13. The method as set forth in claim 1, wherein the microorganism is *Escherichia coli.*

14. The method as set forth in claim 1, wherein the microorganism is yeast or mold.

15. The method as set forth in claim 1, wherein the microorganism is algae.

* * * * *